United States Patent
Bourke, Jr. et al.

(10) Patent No.: US 10,232,190 B2
(45) Date of Patent: Mar. 19, 2019

(54) PHOSPHORS AND SCINTILLATORS FOR LIGHT STIMULATION WITHIN A MEDIUM

(71) Applicants: IMMUNOLIGHT, LLC., Detroit, MI (US); DUKE UNIVERSITY, Durham, NC (US)

(72) Inventors: Frederic A. Bourke, Jr., Aspen, CO (US); Harold Walder, Oak Island, NC (US); Zakaryae Fathi, Raleigh, NC (US); Michael J. Therien, Durham, NC (US); Mark W. Dewhirst, Chapel Hill, NC (US); Ian N. Stanton, Durham, NC (US); Jennifer Ann Ayres, Raleigh, NC (US); Diane Renee Fels, Cincinnati, OH (US); Joseph A. Herbert, Richmond, VA (US)

(73) Assignees: IMMUNOLIGHT, LLC., Detroit, MI (US); DUKE UNIVERSITY, Durham, NC (US)

( * ) Notice: Subject to any disclaimer, the term of this patent is extended or adjusted under 35 U.S.C. 154(b) by 0 days.

(21) Appl. No.: 15/649,917

(22) Filed: Jul. 14, 2017

(65) Prior Publication Data
US 2017/0319868 A1 Nov. 9, 2017

Related U.S. Application Data

(62) Division of application No. 14/131,564, filed as application No. PCT/US2012/045930 on Jul. 9, 2012.

(60) Provisional application No. 61/505,849, filed on Jul. 8, 2011.

(51) Int. Cl.
*A61N 5/06* (2006.01)
*A61K 41/00* (2006.01)
*A61N 5/10* (2006.01)

(52) U.S. Cl.
CPC .......... *A61N 5/062* (2013.01); *A61K 41/0085* (2013.01); *A61N 5/1077* (2013.01); *A61N 5/0622* (2013.01); *A61N 2005/0661* (2013.01); *A61N 2005/1091* (2013.01); *A61N 2005/1098* (2013.01)

(58) Field of Classification Search
CPC .... A61N 5/1077; A61N 5/0622; A61N 5/062; A61N 2005/1066; A61N 2005/1098; A61N 2005/1091
See application file for complete search history.

(56) References Cited

U.S. PATENT DOCUMENTS

| | | | |
|---|---|---|---|
| 6,200,748 B1 | 3/2001 | Smith et al. | |
| 6,504,899 B2 | 1/2003 | Pugachev et al. | |
| 6,645,464 B1 | 11/2003 | Hainfeld | |
| 9,358,292 B2 * | 6/2016 | Bourke, Jr. ............ | A61K 47/02 |
| 2004/0181114 A1 | 9/2004 | Hainfeld et al. | |
| 2004/0198857 A1 * | 10/2004 | Dejneka .................. | G03F 7/029 522/2 |
| 2005/0020869 A1 | 1/2005 | Hainfeld et al. | |
| 2005/0256360 A1 | 11/2005 | Hainfeld et al. | |
| 2007/0140428 A1 | 6/2007 | Toth | |
| 2007/0217996 A1 * | 9/2007 | Levy .................. | A61K 41/0038 424/1.33 |
| 2008/0063142 A1 | 3/2008 | Weil | |
| 2009/0186060 A1 | 7/2009 | Hainfeld et al. | |
| 2010/0003316 A1 | 1/2010 | Vo Dinh et al. | |
| 2011/0117202 A1 | 5/2011 | Bourke, Jr. et al. | |
| 2011/0263920 A1 | 10/2011 | Bourke, Jr. et al. | |
| 2014/0343479 A1 | 11/2014 | Bourke et al. | |

FOREIGN PATENT DOCUMENTS

| | | |
|---|---|---|
| WO | WO 2004/112590 A2 | 12/2004 |
| WO | WO 2004/112590 A3 | 12/2004 |
| WO | WO 2005/030267 A1 | 4/2005 |
| WO | WO 2010/009106 A1 | 1/2010 |

OTHER PUBLICATIONS

International Search Report dated Nov. 6, 2012 in PCT/US12/045930 Filed Jul. 9, 2012.
Extended European Search Report dated Apr. 22, 2015 in Patent Application No. 12810688.7.

* cited by examiner

*Primary Examiner* — Sanza L. McClendon
(74) *Attorney, Agent, or Firm* — Oblon, McClelland, Maier & Neustadt, L.L.P.

(57) ABSTRACT

A system and method for light stimulation within a medium. The system has a reduced-voltage x-ray source configured to generate x-rays from a peak applied cathode voltage at or below 105 kVp, and a plurality of energy-emitting particles in the medium which, upon radiation from the x-ray source, radiate at a first lower energy than the x-ray source to interact with at least one photoactivatable agent in the medium. The method introduces the plurality of energy-emitting particles into the medium, radiates the energy-emitting particles in the medium with x-rays generated from a peak applied cathode voltage at or below 105 kVp; and emits a lower energy than the x-ray source to interact with the medium or with at least one photoactivatable agent in the medium.

50 Claims, 43 Drawing Sheets

1. Incubate w/ psoralen
2. Expose to energy source (UVA, Xray + NP)

→ Crosslinked DNA

→ ss DNA

3. Denaturing conditions (ie. heat, formamide)
4. Agarose Gel

Experimental conditions for the effect of temperature and distance from the X-Ray source

| Phosphor | 320 kvp, 10mA | |
|---|---|---|
| | Distance from the source (cm) | Temperature (C) |
| S1 | 26.5 | 15C |
| S2 | 26.5 | 21C |
| S3 | 26.5 | 33C |
| S4 | 35 | 25C |
| S5 | 40.5 | 25C |
| S6 | 0.1 | 25C |

◯ ds signal    ◯ ss signal

Experimental conditions for testing the effect of total delivered energy (some conditions had constant power and some conditions had constant flux)

| [Phosphor] | Constant Power | | | | | | Constant Flux / Different kVP | | | | | |
| --- | --- | --- | --- | --- | --- | --- | --- | --- | --- | --- | --- | --- |
| | 10 mA | | 20 mA | | 30 mA | | 30 mA | | 30 mA | | 30 mA | |
| | 320 kvp | | 160 kvp | | 105 kvp | | 105 kvp | | 80 kvp | | 40 kvp | |
| | 2 min | 6 min | 2 min | 6 min | 2 min | 6 min | 2 min | 6 min | 2 min | 6 min | 2 min | 6 min |
| S1 | X | | | | | | | | | | | |
| S2 | | X | | | | | | | | | | |
| S3 | | | X | | | | | | | | | |
| S4 | | | | X | | | | | | | | |
| S5 | | | | | X | | X | | | | | |
| S6 | | | | | | X | | X | | | | |
| S7 | | | | | | | | | X | | | |
| S8 | | | | | | | | | | X | | |
| S9 | | | | | | | | | | | X | |
| S10 | | | | | | | | | | | | X |
| S11 * | | | | | X | | | | | | | |
| S12 * | | | | | | X | | | | | | |

The luminosity results from the dsDNA and the ssDNA.
The higher the number the higher brightness

|     | ds DNA | ss DNA |
|-----|--------|--------|
| S1  | 2      | 0      |
| S2  | 0      | 1      |
| S3  | 2      | 0      |
| S4  | 0      | 3      |
| S5  | 1      | 1      |
| S6  | 0      | 4      |
| S7  | 3      | 0      |
| S8  | 0      | 4      |
| S9  | 3      | 0      |
| S10 | 1      | 1      |
| S11 | 1      | 1      |
| S12 | 0      | 4      |

| Power Condition | Time (sec) | kV | m-A | Total Energy (joules) |
|---|---|---|---|---|
| S1 | 120 | 320 | 10 | 384,000 |
| S2 | 360 | 320 | 10 | 1,152,000 |
| S3 | 120 | 160 | 20 | 384,000 |
| S4 | 360 | 160 | 20 | 1,152,000 |
| S5 | 120 | 105 | 30 | 378,000 |
| S6 | 360 | 105 | 30 | 1,134,000 |
| S7 | 120 | 80 | 30 | 288,000 |
| S8 | 360 | 80 | 30 | 864,000 |
| S9 | 120 | 40 | 30 | 144,000 |
| S10 | 360 | 40 | 30 | 432,000 |
| S11 * | 120 | 160 | 20 | 384,000 |
| S12 * | 360 | 160 | 20 | 1,152,000 |

Experimental conditions for testing the effect of phosphor concentration variation.

| [Phosphor] | Samples | Constant flux different KVP 30 mA | | | |
|---|---|---|---|---|---|
| | | 80 kvp 2 min | 40 kvp 2 min | 20 kvp 2 min | 10 kvp * 2 min |
| 0.1mg/ml | S1 | ▓ | | | |
| | S2 | | ▓ | | |
| | S3 | | | ▓ | |
| | S4 | | | | ▓ |
| repeat | S5 | | | | |
| | S6 | | | | |
| 0.15mg/ml | S7 | ▓ | | | |
| | S8 | | ▓ | | |
| | S9 | | | ▓ | |
| | S10 | | | | ▓ |
| 0.18mg/ml | S11 | | ▓ | | |
| | S12 | | | ▓ | |
| | S13 | | | | ▓ |
| | S14 ** | 2nd | | 1st | |
| | S15 | | | | |
| | S16 *** | 1st | | 2nd | |
| repeat | S17 | | | | |

Various colors can be used to optimize the X-ray irradiation treatment. For example the application of photo-catalytic energy can be done in conjunction with energy able to induce conformational changes in certain reactive site.

Figure 12B

| The visible Spectrum | | |
|---|---|---|
| Color | Frequency | Wavelength |
| violet | 668–789 THz | 380–450 nm |
| blue | 631–668 THz | 450–475 nm |
| cyan | 606–630 THz | 476–495 nm |
| green | 526–606 THz | 495–570 nm |
| yellow | 508–526 THz | 570–590 nm |
| orange | 484–508 THz | 590–620 nm |
| red | 400–484 THz | 620–750 nm |

Figure 12C

X-Ray Phosphors

| # | Phosphor | Emission Spectrum | X-Ray Absorption | | | Microstructure | | Hygroscopic |
|---|---|---|---|---|---|---|---|---|
| | | Peak Emission (nm) | Emiss Eff (%) | Eff (Z) | K-edge (keV) | Specific Gravity | Crystal Structure | |
| 1 | BaFCl:Eu2+ | 380 | 13 | 49.3 | 37.38 | 4.7 | Tetragonal | N |
| 2 | BaSO4-:Eu2+ | 390 | 6 | 45.5 | 37.38 | 4.5 | Rhombic | N |
| 3 | LaOBr:Tm3+ | 360, 460 | 14 | 49.3 | 38.92 | 6.3 | Tetragonal | N |
| 4 | YTaO4 | 337 | | 59.8 | 67.42 | 7.5 | Monolithic | N |
| 5 | YTaO4:Nb (*) | 410 | 11 | 59.8 | 67.42 | 7.5 | Monolithic | N |
| 6 | CaWO4 | 420 | 5 | 61.8 | 69.48 | 6.1 | Tetragonal | N |
| 7 | LaOBr:Tb3+ | 420 | 20 | 49.3 | 38.92 | 6.3 | Tetragonal | N |
| 8 | Y2O2S:Tb3+ | 420 | 18 | 34.9 | 17.04 | 4.9 | Hexgonal | N |
| 9 | ZnS:Ag | 450 | 17 | 26.7 | 9.66 | 3.9 | Hexgonal | N |
| 10 | (Zn,Cd)S:Ag | 530 | 19 | 38.4 | 9.66/26.7 | 4.8 | Hexgonal | N |
| 11 | Gd2O2S:Tb3+ | 545 | 13 | 59.5 | 50.22 | 7.3 | Hexgonal | N |
| 12 | La2O2S:Tb3+ | 545 | 12.5 | 52.6 | 38.92 | 6.5 | Hexgonal | N |

Phosphors for Mixing

| Item # | Phosphor | Emission Spectrum | | | X-Ray Absorption | | | Hygroscopic |
|---|---|---|---|---|---|---|---|---|
| | Color | Peak Emission (nm) | Emiss Eff (%) | Eff (Z) | K-edge (keV) | Specific Gravity | Crystal Structure | |
| 24 | Zn3(PO4)2:Tl+ | 310 | | | | | | N |
| 33 | BaF2 | 310 | | | | | | Slightly |
| 30 | CsI | 315 | | | | | | N |
| 23 | Ca3(PO4)2:Tl+ | 330 | | | | | | N |
| 4 | YTaO4 | 337 | | 59.8 | 67.42 | 7.5 | Monolithic | N |
| 38 | CsI:Na | 338 | | | | | | Y |
| 14 | BaSi2O5:Pb2+ | 350 | | | | | | N |
| 27 | Borosilicate | 350 | | | | | | N |
| 34 | LaCl3(Ce) | 350 | | | | | | Y |
| 16 | SrB4O7F:Eu2+ | 360 | | | | | | N |
| 20 | RbBr:Tl+ | 360 | | | | | | ? |
| 15 | (Ba, Sr, Mg)3Si2O7:Pb2+ | 370 | | | | | | N |
| 17 | YAlO3:Ce3+ | 370 | | | | | | N |
| 37 | BC-422 | 370 | | | | | | Organic | ? |
| 1 | BaFCl:Eu2+ | 380 | 13 | 49.3 | 37.38 | 4.7 | Tetragonal | N |
| 2 | BaSO4:Eu2+ | 390 | 6 | 45.5 | 37.38 | 4.5 | Rhombic | N |
| 19 | BaFBr:Eu2+ | 390 | | | | | | ? |
| 36 | BC-420 | 391 | | | | | Organic | ? |
| 35 | BC-414 | 392 | | | | | Organic | ? |
| 25 | SrMgP2O7:Eu2+ | 394 | | | | | | N |
| 18 | BaBr2:Eu2+ | 400 | | | | | | N |
| 22 | (Sr, Ba)Al2Si2O8:Eu2+ | 400 | | | | | | N |
| 5 | YTaO4:Nb (?) | 410 | 11 | 59.8 | 67.42 | 7.5 | Monolithic | N |
| 21 | Y2SiO5:Ce3+ | 410 | | | | | | N |
| 6 | CaWO4 | 420 | 5 | 61.8 | 69.48 | 6.1 | Tetragonal | N |
| 7 | LaOBr:Tb3+ | 420 | 20 | 49.3 | 38.92 | 6.3 | Tetragonal | N |
| 8 | Y2O2S:Tb3+ | 420 | 18 | 34.9 | 17.04 | 4.9 | Hexgonal | N |
| 13 | Lu2SiO5:Ce3+ | 420 | | | | | | N |
| 26 | Lu1.8 Y0.2SiO5:Ce | 420 | | | | | | N |
| 9 | ZnS:Ag | 450 | 17 | 26.7 | 9.66 | 3.9 | Hexgonal | N |
| 29 | CdWO4 | 475 | | | | | | Slightly |
| 28 | Bi4Ge3O12 (BGO) | 480 | | | | | | N |
| 10 | (Zn,Cd)S:Ag | 530 | 19 | 38.4 | 9.66/26.7 | 4.8 | Hexgonal | N |
| 11 | Gd2O2S:Tb3+ | 545 | 13 | 59.5 | 50.22 | 7.3 | Hexgonal | N |
| 12 | La2O2S:Tb3+ | 545 | 12.5 | 52.6 | 38.92 | 6.5 | Hexgonal | N |
| 31 | Y3Al5O12 (Ce) | 550 | | | | | | N |
| 3 | LaOBr:Tm3+ | 360, 460 | 14 | 49.3 | 38.92 | 6.3 | Tetragonal | N |
| 32 | CaF2(Eu) | 435/300 | | | | | | N |

Figure 13J-C
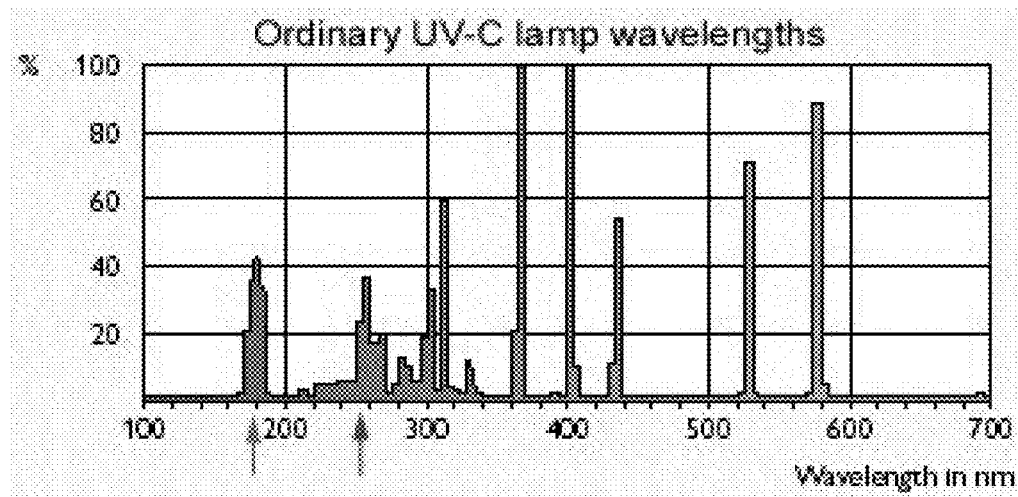
Figure 13K
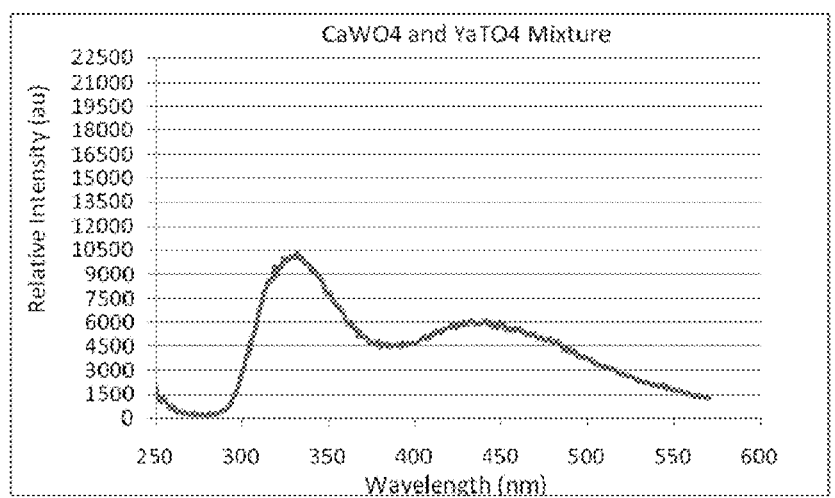

Figure 15A

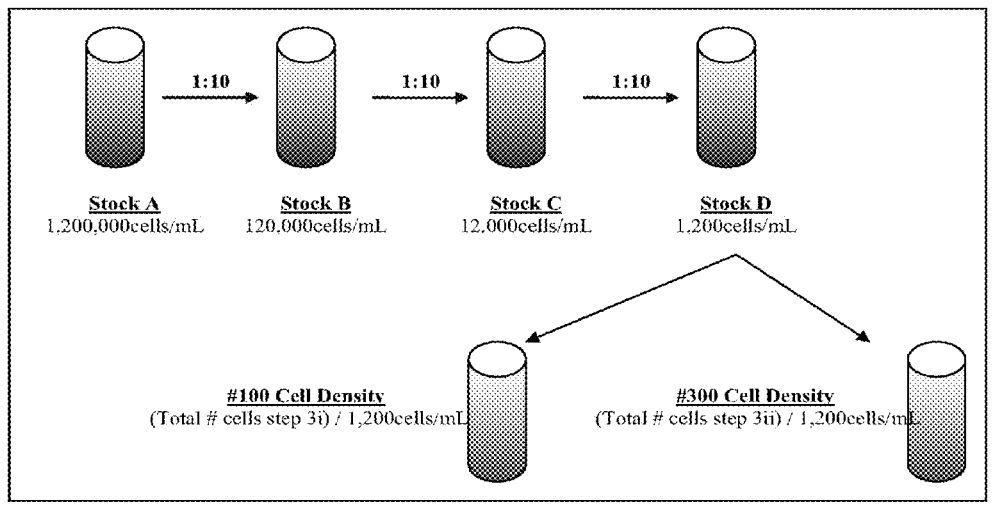

Figure 15B

| Code | Phosphor Material | Emission Spectrum | X-Ray Absorption | | | Denisty g/cc | Xtal | Hygroscopic |
|---|---|---|---|---|---|---|---|---|
| | Color | Peak Emission (nm) | Emiss Eff (%) | Eff (Z) | K-edge (keV) | Specific Gravity | Crystal Structure | |
| BP1 | CaWO4:Pb | 425 | | | | | | N |
| BP2 | Y2SiO5:Ce | 410 | | | | | | N |
| BP3-C | YTaO4 | 337 | 10 | 59.8 | 67.42 | 7.5 | Monolithic | N |
| BP3-C | YTaO4 | 337 | 10 | 59.8 | 67.42 | 7.5 | Monolithic | N |
| BP4 | BASF-1 | 460 | | | | | | |
| BP5 | BASF-2 | 490 | | | | | | |
| BP6 | YTaO4:Nb (*) | 410 | 11 | 59.8 | 67.42 | 7.5 | Monolithic | N |
| BP6-C | YTaO4:Nb (*) | | | | | | | |
| BP7-C | LaOBr:Tm3+ (coated) | 360, 460 | 14 | 49.3 | 38.92 | 6.3 | Tetragonal | N |
| BP8-C | LaF3:Ce | 280 | | | | | | |
| BP9 | Y2O3 | 365 | | | | | | |
| BP-10 | BaSO4-:Eu2+ (coated) | 390 | 6 | 45.5 | 37.38 | 4.5 | Rhombic | N |
| BP10-C | BaSO4-:Eu2+ (coated) | 390 | 6 | 45.5 | 37.38 | 4.5 | Rhombic | N |

A container including a solution containing nano-particles

Disposing of the nano particles from the container onto a rotating wafer surface Wafer drying producing a nano particle dispersion across the surface of the wafer Wafer with nano particle dispersion is taken to a physical vapor deposition system Wafer with nano particle dispersion is lowered onto for example a biased and heated stage of a physical vapor deposition system for applying a coating to a top half of the nano particles Mass transport and necking between particles

B

PHOSPHORS AND SCINTILLATORS FOR LIGHT STIMULATION WITHIN A MEDIUM

CROSS REFERENCE TO RELATED APPLICATIONS

This application is a Divisional of U.S. Ser. No. 14/131,564, filed Jul. 11, 2014, pending, which was a 371 national stage application of PCT application PCT/US12/045930, filed Jul. 9, 2012, and claims priority to U.S. Ser. No. 61/505,849 filed Jul. 8, 2011, the entire contents of each of which is incorporated herein by reference. This application is also related to Provisional Application Ser. No. 60/954,263, filed Aug. 6, 2007, and 61/030,437, filed Feb. 21, 2008, and U.S. application Ser. No. 12/059,484, filed Mar. 31, 2008, the contents of which are hereby incorporated herein by reference. This application is also related to U.S. application Ser. No. 11/935,655, filed Nov. 6, 2007; and Provisional Application Ser. No. 61/042,561, filed Apr. 4, 2008; 61/035,559, filed Mar. 11, 2008, and 61/080,140, filed Jul. 11, 2008, the entire contents of which are hereby incorporated herein by reference. This application is related to U.S. patent application Ser. No. 12/401,478 filed Mar. 10, 2009, the entire contents of which are hereby incorporated herein by reference. This application is related to U.S. patent application Ser. No. 11/935,655, filed Nov. 6, 2007, and Ser. No. 12/059,484, filed Mar. 31, 2008; U.S. patent application Ser. No. 12/389,946, filed Feb. 20, 2009; U.S. patent application Ser. No. 12/417,779, filed Apr. 3, 2009, the entire disclosures of which are hereby incorporated by reference. This application is related to U.S. provisional patent application 61/161,328, filed Mar. 18, 2009, the entire disclosure of which are hereby incorporated by reference. This application is related to U.S. provisional patent application Ser. No. 12/417,779, filed Apr. 3, 2009, the entire disclosure of which is hereby incorporated by reference. This application is related to PCT application PCT/US2009/050514, filed Jul. 14, 2009, the entire disclosure of which are hereby incorporated by reference. This application is related to U.S. patent application Ser. No. 12/725,108, filed Mar. 16, 2010, the entire disclosure of which is hereby incorporated by reference.

This application is related to U.S. patent application Ser. No. 12/764,184, filed Apr. 21, 2010, the entire disclosure of which is hereby incorporated by reference. This application is related to U.S. provisional patent application 61/443,019, filed Feb. 15, 2011, the entire disclosure of which is hereby incorporated by reference.

BACKGROUND OF THE INVENTION

Field of Invention

The invention pertains to phosphorescing, fluorescing and scintillating materials and methods of use for increasing the effectiveness and/or the efficiency of light emission in a subject or medium being treated by X-ray radiation or a particle beam. The invention also pertains to methods and structures for assembling nano-particles to increase their net light output under excitation.

Discussion of the Background

Light modulation from a deeply penetrating radiation like X-ray to a photo-catalytic radiation like UV, opens the possibility for activating bio-therapeutic agents of various kinds within mammalian bodies. Other possibilities include the activation of photo-catalysts in mediums for cross-linking reactions in polymeric chains and polymer based adhesives. These examples are but two examples of a number of possibilities that can be more generally described as the use of a conversion material to convert an initiating radiation that is deeply penetrating to another useful radiation possessing the capability of promoting photo-based chemical reactions. The photo-chemistry is driven inside mediums of far ranging kinds including organic, inorganic or composited from organic and inorganic materials.

The photo-activation with no line of site required can be done in-vivo and ex-vivo such as those carried out in cell cultures. In turn, the photo activation of select bio-therapeutic agent, and conceivably more than one agent at a time, can lead to the onset of a desirable chemical reaction, or a cascade of reactions, that in turn lead to a beneficial therapeutic outcome. As an example, the binding of psoralen to DNA through the formation of monoadducts is well known to engender an immune response if done properly. An in-depth treatise of the subject is available in the open literature. Psoralen under the correct photo-catalytic light gains the aptitude to bind to DNA. Psoralen has been reported to react to other sites that have a suitable reactivity including and not limited to cell walls. If this reaction is of the correct kind, as is the case for psoralen-DNA monoadducts formation, the binding leads to a programmable cell death referred to as Apoptosis. Such programmable cell death, if accomplished over a sufficiently large cell population, can signal the body to mount an immune response enabling target specific cell kill throughout the body. Such immune response is of the upmost importance for various medical treatments including cancer cure.

The cascade of events described above has at its source the modulation of electromagnetic energy from the X-ray to the UV energy using phosphors in the presence of bio-therapeutic agents; these methods and the like, have been thoroughly described in various patents and patent applications such as those listed in the cross-reference section above.

In particular, in U.S. Ser. No. 11/935,655, entitled "METHODS AND SYSTEMS FOR TREATING CELL PROLIFERATION DISORDERS," the use of a phosphorescent emitting source was described with the advantage of phosphorescent emitting molecules or other source may be electroactivated or photoactivated prior to insertion into the tumor either by systemic administration or direct insertion into the region of the tumor. Phosphorescent materials have longer relaxation times than fluorescent materials. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

In particular, in U.S. Ser. No. 12/401,478, entitled "PLASMONIC ASSISTED SYSTEMS AND METHODS FOR INTERIOR ENERGY-ACTIVATION FROM AN EXTERIOR SOURCE," the use of phosphorescent materials as energy modulation agents was described. The '478 application details a number of modulation agents some having a very short energy retention time (on the order of fs-ns, e.g. fluorescent molecules) whereas others having a very long half-life (on the order of seconds to hours, e.g. luminescent inorganic molecules or phosphorescent molecules). Specific types of energy modulation agents described in the '478 application included $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er3^+$; ZnS:$Mn^{2+}$; ZnS:Mn,$Er^{3+}$.

SUMMARY OF THE INVENTION

In one embodiment, there is provided a system for light stimulation within a medium. The system has a reduced-voltage x-ray source configured to generate x-rays from a peak applied cathode voltage at or below 105 kVp, and a first plurality of energy-emitting particles in the medium which, upon radiation from the x-ray source, radiate at a first lower energy than the x-ray source to interact with the medium or with at least one photoactivatable agent in the medium.

In one embodiment, there is provided a method for light stimulation within a medium. The method includes introducing a first plurality of energy-emitting particles into the medium, radiating the first plurality of energy-emitting particles in the medium with x-rays generated from a peak applied cathode voltage at or below 105 kVp, and emitting a first lower energy than the x-ray source to interact with the medium or with at least one photoactivatable agent in the medium.

In one embodiment, there is provided a system for modulating biological activity within a medium. The system includes a reduced-voltage x-ray source configured to generate x-rays from a peak applied cathode voltage at or below 105 kVp, and a plurality of energy-emitting particles in the medium which, upon radiation from the x-ray source, radiate at a lower energy than the x-ray source to alter the biological activity of the medium.

In one embodiment, there is provided a method for modulating biological activity within a medium. The method includes introducing a plurality of energy-emitting particles into the medium, radiating the plurality of energy-emitting particles in the medium with x-rays generated from a peak applied cathode voltage at or below 105 kVp, and emitting a first lower energy than the x-ray source to alter the biological activity of the medium.

In one embodiment, there is provided a system for light stimulation within a medium. The system includes an initiation source configured to radiate an initiation energy, a first plurality of energy-emitting particles in the medium which (upon radiation from the initiation source) radiate at a first lower energy than the initiation source to interact with at least one photoactivatable agent in the medium, and a second plurality of energy-emitting particles in the medium which (upon radiation from the initiation source) radiate at a second lower energy than the initiation source to interact with at least one photoactivatable agent in the medium. A combination of emission from the first and second plurality of energy-emitting particles produces a spectrum for illumination of the at least one photoactivatable agent in the medium. The spectrum has a wavelength distribution simulating at least a part of an absorption spectrum of the at least one photoactivatable agent.

In one embodiment, there is provided a method for light stimulation within a medium. The method includes introducing a first plurality of energy-emitting particles into the medium, introducing a second plurality of energy-emitting particles into the medium, radiating the first and second plurality of energy-emitting particles in the medium with an initiation energy, emitting from the first and second plurality of energy-emitting particles a first lower energy than the initiation energy and a second lower energy than the initiation energy to interact with at least one photoactivatable agent in the medium. A combination of emission from the first and second plurality of energy-emitting particles produces a spectrum for illumination of the at least one photoactivatable agent in the medium. The spectrum has a wavelength distribution simulating at least a part of an absorption spectrum of the at least one photoactivatable agent.

In one embodiment, there is provided a system for light stimulation within a medium. The system includes a first plurality of light-emitting particles which upon encountering an initiating excitation of light energy or particle beam energy radiate a first output energy having photocatalysis potential to activate photoactivatable agents in the medium, and a second plurality of light-emitting particles which upon encountering the initiating excitation of light energy or particle beam energy radiate a second output energy complementary to the first output. A combination of energy emission from the first and second plurality of energy emitting particles produces a combined energy capable of activating chemical agents inside the medium.

In one embodiment, there is provided a method for light stimulation within a medium. The method includes introducing a first plurality of light-emitting particles into the medium, introducing a second plurality of light-emitting particles into the medium, exposing the first plurality of light-emitting particles to an initiating excitation of light energy or particle beam energy to produce from the first plurality of light-emitting particles a first output energy having photocatalysis potential to activate at least one photoactivatable agent in the medium, and exposing the second plurality of light-emitting particles to an initiating excitation of light energy or particle beam energy to produce from the second plurality of light-emitting particles a second output energy complementary to the first output. A combination of energy emission from the first and second plurality of energy emitting particles produces a combined energy capable of activating chemical agents inside the medium.

In one embodiment, there is provided a system for light stimulation within a medium. The system has a first plurality of light-emitting particles which upon encountering an appropriate initiating excitation of light energy or particle beam energy radiate an output energy having photocatalysis potential to activate photoactivatable agents with minimized impact on the medium. The system further has a second plurality of light-emitting particles which upon encountering the same initiating excitation of light energy or particle beam energy radiate an output energy complementary to the output of the first set of particles.

In one embodiment, there is provided a system for light stimulation within a medium. The system has an x-ray source positioned at a distance from the medium and configured to generate radiation within an energy band bounded by a lower energy threshold capable of inducing desirable reactions and an upper energy threshold leading to denaturization of the medium. The system has an x-ray source control device configured to 1) calculate an x-ray exposure condition including the distance and the above-noted energy band and 2) operate the x-ray source within the x-ray exposure condition. The system has a plurality of energy-emitting particles in the medium which, upon radiation from the x-ray source with energy above the lower energy threshold, radiate at a first lower energy than the x-ray source to interact with the medium or with at least one photoactivatable agent in the medium.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 11A-2 is a schematic of the combination of X-Ray and a microwave guide allowing the simultaneous use of X-Ray energy and microwave energy to interact with a target or reactive site;

FIG. 12B is Table 6 depicting the color spectrum;

FIG. 12C is Table 7 depicting the properties of various x-ray phosphors;

FIG. 13J-A is a schematic of the spectral output of a $YTaO_4$ phosphor chemistry capable of emission in the UVA and $CaWO_4$ capable of emitting in the UVA and in the visible;

FIG. 13J-B is Table 8 depicting properties of various phosphors for mixing;

FIG. 13J-C is a schematic depicting a typical spectrum from a commercial UV light source which has been used to activate psoralens;

FIG. 13K is a schematic of the emission spectra under X-Ray excitation for a powder mixture of CaWO and $YTaO_4$;

FIG. 15A is a schematic depiction of a dilution process for cell assay analysis;

FIG. 15B is Table 9 depicting properties of various phosphors and the names of various phosphors;

DETAILED DESCRIPTION OF THE INVENTION

Figure 1A:
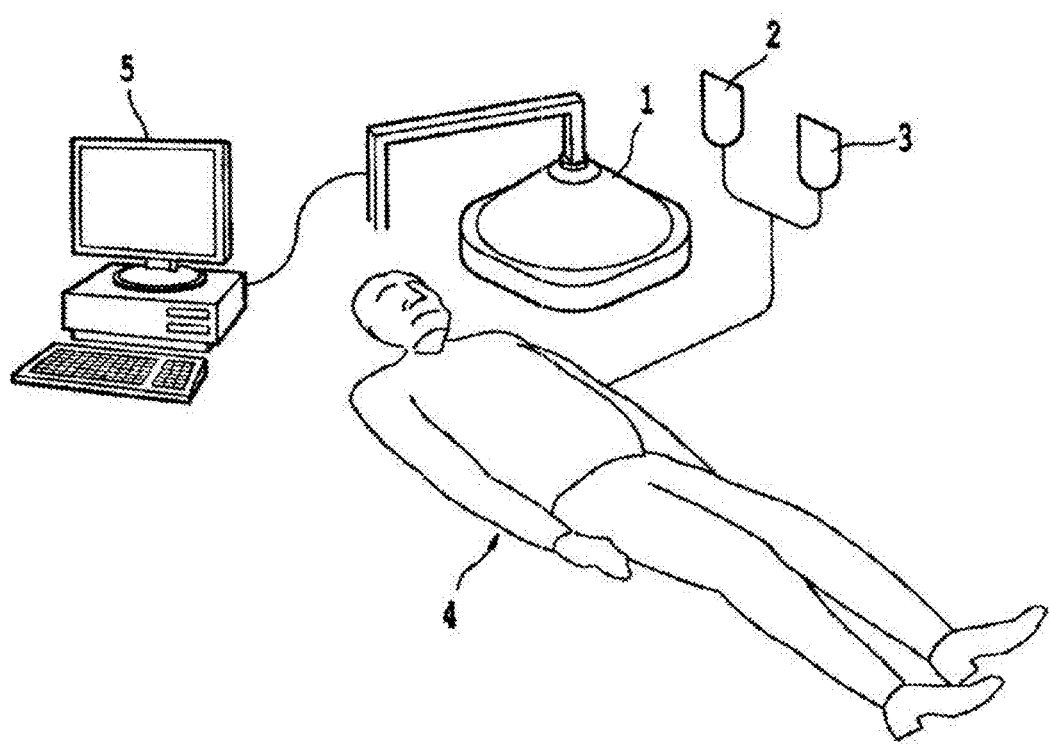
FIG. 1A is a schematic illustration of a system according to one exemplary embodiment of the invention.

Reference will now be made in detail to the present preferred embodiment of the invention, an example of which is illustrated in the accompanying drawings (including color drawings), in which like reference characters refer to corresponding elements.

FIG. 1A illustrates a system according to one exemplary embodiment of the present invention. Referring to FIG. 1A, an exemplary system according to one embodiment of the present invention may have an initiation energy source 1 directed at the subject 4. An activatable pharmaceutical agent 2 and an energy modulation agent 3 can be administered to the subject 4. The initiation energy source may additionally be controlled by a computer system 5 that is capable of directing the delivery of the initiation energy (e.g., x-rays).

In further embodiments, dose calculation and robotic manipulation devices may also be included in the system to adjust the distance between the initiation energy source 1 and the the subject 4 and/or to adjust the energy and/or dose (e.g., kVp or filtering) of the initiation energy source such that the x-rays incident on the target site are within an energy band bounded by a lower energy threshold capable of inducing desirable reactions and an upper energy threshold leading to denaturization of the medium. Results described below show the criticality of the range of X-Ray kVp. Further refinements in the x-ray energy and dose can be had by adjusting the distance to the subject 5 or the intervening materials between the target site and the initiation energy source 1.

In yet another embodiment, there is also provided a computer implemented system for designing and selecting suitable combinations of initiation energy source, energy transfer agent, and activatable pharmaceutical agent, comprising:

a central processing unit (CPU) having a storage medium on which is provided:

a database of excitable compounds;

a first computation module for identifying and designing an excitable compound (e.g., a photoactivatable drug) that is capable of binding with a target cellular structure or component; and a second computation module predicting the absorption energy of the excitable compound, wherein the system, upon selection of a target cellular structure or component, computes an excitable compound that is capable of interacting with the target structure.

The computer-implemented system according to one embodiment of the present invention may have a central processing unit (CPU) connected to a memory unit, configured such that the CPU is capable of processing user inputs and selecting a combination of initiation source (or initiation energies or distances), activatable pharmaceutical agent, and energy transfer agents for use in a method of the present invention.

The computer-implemented system according to one embodiment of the present invention includes (or is programmed to act as) an x-ray source control device configured to calculate an x-ray exposure condition including a distance between the initiation energy source 1 and the subject 4 and the energy band bounded by the above-noted lower energy threshold capable of inducing desirable reactions and the above-noted upper energy threshold leading to denaturization of the medium. The x-ray source control device operates the x-ray source (the initiation energy source 1) within the x-ray exposure condition to provide a requisite energy and/or dose of x-rays to the subject or a target site of the subject.

Light intensity plays a substantial role in photo-catalysis. The more light intensity that is available, the higher the chance of activating reactions that are suitable for photo-activation. Conversely, the lower the intensity, the lesser the chance of activating chemical reactions. In other words, usually, the photonic flux at a sufficient intensity (number of photons per unit time) is necessary to trigger reactions.

Besides light intensity, a minimum level of spectral matching between the radiation(s) emanating from the conversion media and the radiation that can be absorbed by the photo-catalyst being targeted is desired. In other words, the emitted radiation has to be suitable to the absorption of the chemical species under consideration.

The effect of psoralen on crosslinking DNA was used to determine the effectiveness of light modulating particles (phosphors, scintillators and combinations thereof) under X-Ray irradiation. Of particular interest were the crosslinking signals associated with DNA and in particular having a minimize effect of denaturing DNA while maximizing the density of desirable crosslinks such as those needed to engender an immune response.

Figures 1B, 1C:
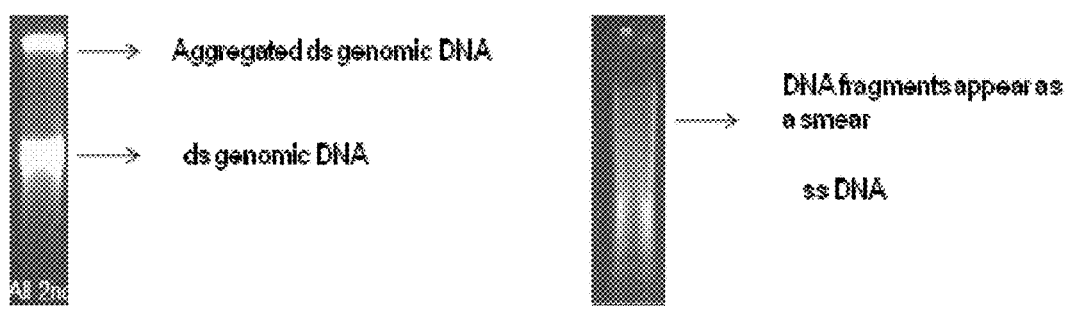
FIG. 1B is a graphical representation of DNA gel products in particular a-aggregated ds genomic DNA and ds genomic DNA.
FIG. 1C is a graphical representation of DNA gel products in particular b-DNA fragments and ssDNA.

Gel electrophoresis is method for qualitatively analyzing DNA crosslinking. If no denaturing conditions are applied, then an observable pattern consisting of an aggregation of double stranded genomic DNA (or ds genomic DNA) are present as illustrated in FIG. 1B. On the other hand, if denaturing conditions are applied, then an observable signal represented by a smear pattern is observed since a distribution of species are present, not just a single stranded DNAs illustrated in FIG. 1C.

DNA was incubated with psoralen then exposed to X-Ray energy in the presence of nano particles and a biotherapeutic agent. Denaturing conditions were then applied in the form of heat, formamide. Agarose gel having an electric field gradient was used to force DNA to travel through its pores by a diffusion process. The signals resulting from the ds DNA and ss DNA are then recorded using the fluorescent dye technique described above (as illustrated in FIG. 2). The intensity of the gel is directly related to the mass loading.

A DNA crosslinking test plan for using X-Ray radiation as the initiating crosslinking radiation. The experimental space was mapped out, and variables were altered as part of the experimental plan. Surprising results were observed in that more ssDNA was generated at higher X-Ray intensity. The solutions were prepared using a Total volume per glass vial (2 mL DNA solution+AMT or phosphors). Dissolved stock lyophilized DNA (2 mg) in 20 mL of 1×PBS. The drug concentrations of AMT was kept at a fixed concentration of 0.1 ΦM. The phosphors were added to the solution as follows: 0.1 mg/mL final concentration in DNA. This was obtained by creating a suspension of 1 mg/mL BP7c suspension in PBS, adding 200 ΦL suspension to vial of 2 mL DNA+TMPS solution and finally adding 200 ΦL suspension to vial of 2 mL DNA+AMT solution. After treatment, all the vials were transferred to ice, covered from the light, and stored in cold room on wet ice prior to the gel electrophoresis measurements.

Figures 3A, 3B:
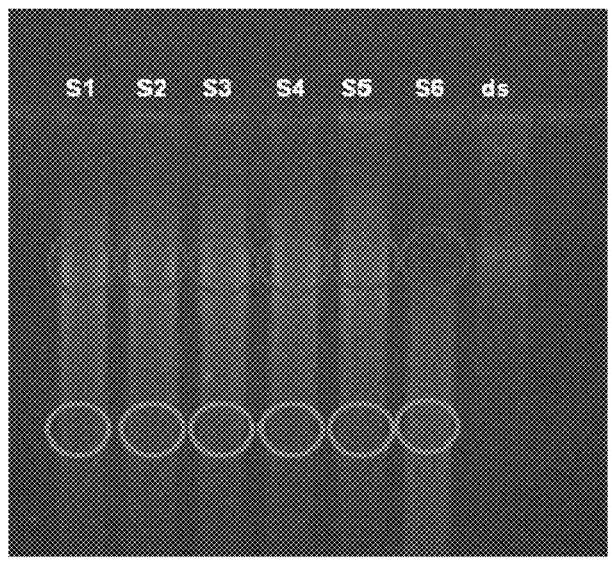
FIG. 3A is a schematic depicting gel electrophoresis results post DNA crosslinking attempt using temperature and distance from the source as variables.
FIG. 3B is Table 1 depicting experimental conditions for the effect of temperature and distance from the X-Ray source.

FIG. 3A shows the gel electrophoresis results post DNA crosslinking attempts under X-Ray radiation and using temperature and distance from the source as variables. The experimental conditions are provided in Table 1 shown in FIG. 3B.

All the experiments were conducted using a constant source voltage and amperage. Sample S6 in FIG. 3 had the most energy input from the irradiator. As shown in FIG. 3A, sample condition S6 revealed that more X-Ray intensity yielded more ssDNA than other conditions of lesser energy inputs. Production of ssDNA is the less desirable result. As noted above, the generation of more ssDNA at higher X-Ray intensity was the unexpected result.

Figures 4A, 4B:
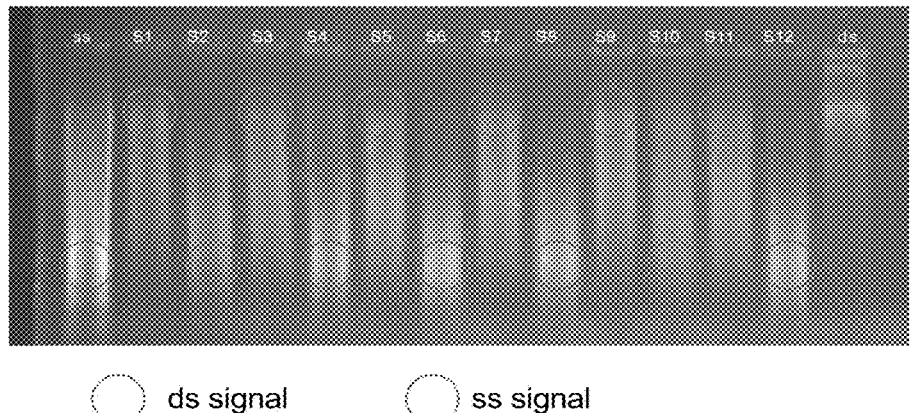
FIG. 4A is a schematic depicting gel electrophoresis results post a DNA crosslinking attempt using various experimental conditions having the total delivered energy as a variable.
FIG. 4B is Table 2 depicting experimental conditions for testing the effect of total delivered energy (some conditions had constant power and some conditions had constant flux)

FIG. 4A illustrates the results from gel electrophoresis post DNA crosslinking attempts using various experimental conditions. FIG. 4B shows Table 2 providing the experimental conditions for testing the effect of total delivered energy (some conditions had constant power and some conditions had constant flux).

The total delivered energy was an experimentally designed variable. The power was maintained constant by varying kVp (peak voltage on the x-ray cathode) and filament current accordingly. The impact of a constant flux was tested. For each of these conditions, time was fixed in two major intervals: e.g., a two minutes duration or a six minute duration. As shown in FIG. 4A, all the two minute runs (regardless of the flux and kVp conditions) showed a strong ds DNA signal. On the other hand, all the six minute runs (regardless of the flux and kVp conditions) showed a strong ss-DNA signal. In effect the total energy delivered to the system makes a substantial difference in the formation of ss-DNA versus ds-DNA. Though the DNA crosslinking test is qualitative rather than quantitative, the exhibited trend is clear and unambiguous. More energy leads to the formation of smaller molecular weight species from the original DNA.

A visual ranking of brightness from the electrophoresis technique was adopted to rank the various conditions. The results are tabulated in Table 3 shown in FIG. 4C.

Figures 4C, 5A:
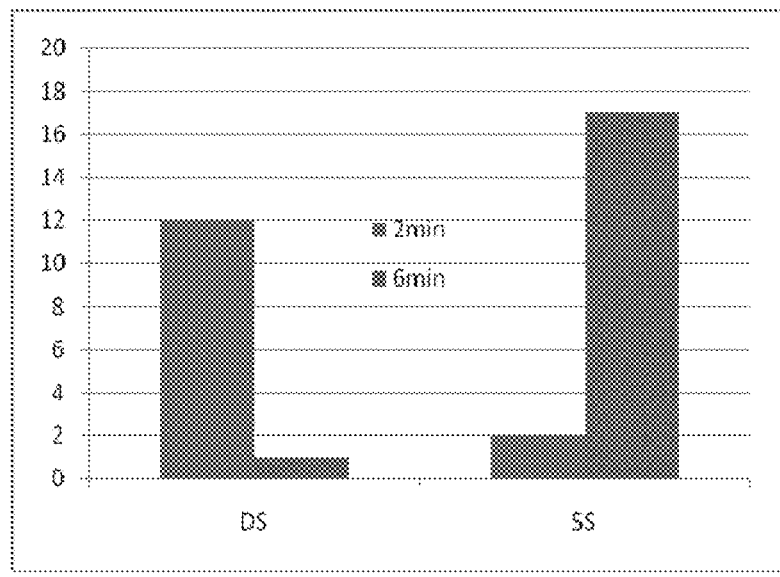
FIG. 4C is Table 3 depicting the luminosity results from the ds DNA and the ss DNA (with the higher the number the higher brightness)
FIG. 5A is a depiction of the sum of all the brightness results from two minute and six minute X-Ray irradiation treatments.

The sum total of all the brightness results in the "ds" column and the sum total of all the brightness in the "ss" column are plotted in FIG. 5A for the two duration periods applied during the test. Clearly, the two minute duration X-ray irradiation treatments lead to more ds-DNA, and the six minute duration X-ray irradiation treatments lead to more ss-DNA.

Figures 5B, 6A:
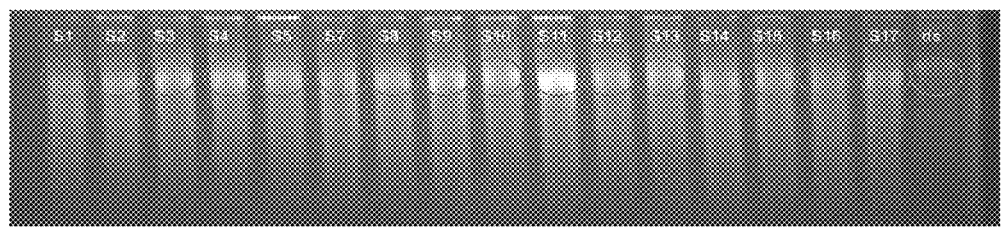
FIG. 5B is Table 4 depicting the total energy delivered per experimental condition.
FIG. 6A is a schematic depicting gel electrophoresis results post a DNA crosslinking attempt using varying phosphor concentrations at kVp values at or below 80 kVp, with all conditions yielding a ds-DNA signal.

The total energy delivered during the X-Ray treatments was calculated by integrating the power delivery over the time period by multiplying the voltage and the amperage, as illustrated in Table 4 shown in FIG. 5B.

In order to test the impact of phosphor loading, a series of phosphor loadings were prepared for testing. The X-ray treatment was kept at two minutes for the conditions in this experiment (for the sake of confirming the repeatability of the fact that the lower level of energy delivery leads to ds-DNA signal). The phosphor concentration was varied from 0.1 mg/ml to 0.15 mg/ml and 0.18 mg/ml.

Figures 6B, 7:
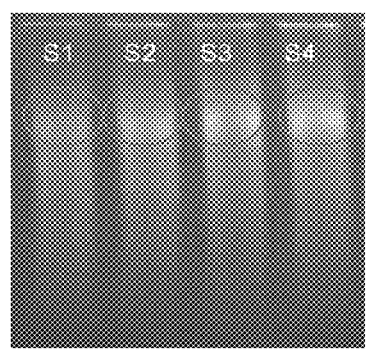
FIG. 6B is Table 5 depicting experimental conditions for testing the effect of phosphor concentration variation.
FIG. 7 is a schematic depicting gel electrophoresis results post a DNA crosslinking attempt using kVp levels of 80 kVp for S1, 40 kVp for S2, 20 kVp for S3, and 10 kVp for S4.

FIG. 6A illustrates the results from gel electrophoresis post DNA crosslinking attempts using varying phosphor concentrations at kVp values at or below 80 kVp. As illustrated in FIG. 6, the ds-DNA signal can be observed across the entire series of samples treated according to the experimental conditions in Table 5 (shown in FIG. 6B). This reinforces the need to use lower incident energy levels to avoid generating ssDNA.

Furthermore as illustrated in FIG. 7, going to lower kVp values during the irradiation treatment can further be demonstrated in this subgroup from Table 5.

Sample S4 treated using 10 kVp exhibits a relatively stronger ds-DNA signal than S1 which was treated using 80 kVp. The lower the kVp results in stronger observable ds-DNA signal for the phosphor in 0.1 mg/mL final concentration in DNA. The comparison of S1, S2, S3 and S4 conditions further reinforces that lower kVp values are helpful to the crosslinking process.

As illustrated in FIG. 7, the condition that lead to most crosslinking was sample S11. The phosphor in this case is 0.18 mg/mL final concentration in DNA and crosslinks best at 40 kVp. Besides the positive results at 80 kVp and below, positive results at 105 kVp have been obtained.

Figure 8:
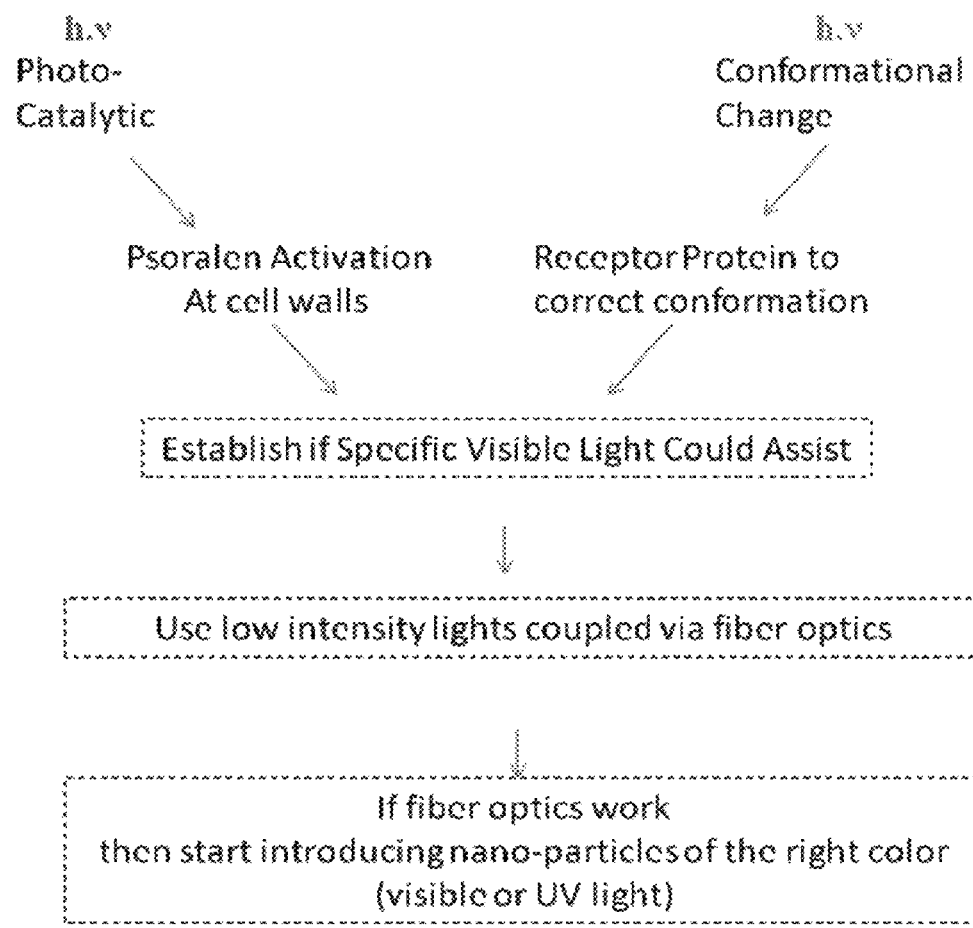
FIG. 8 is a schematic illustration of how photo-catalytic light works cooperatively with non ionizing radiation to potentiate the activation of bio-therapeutics.
Figure 9:
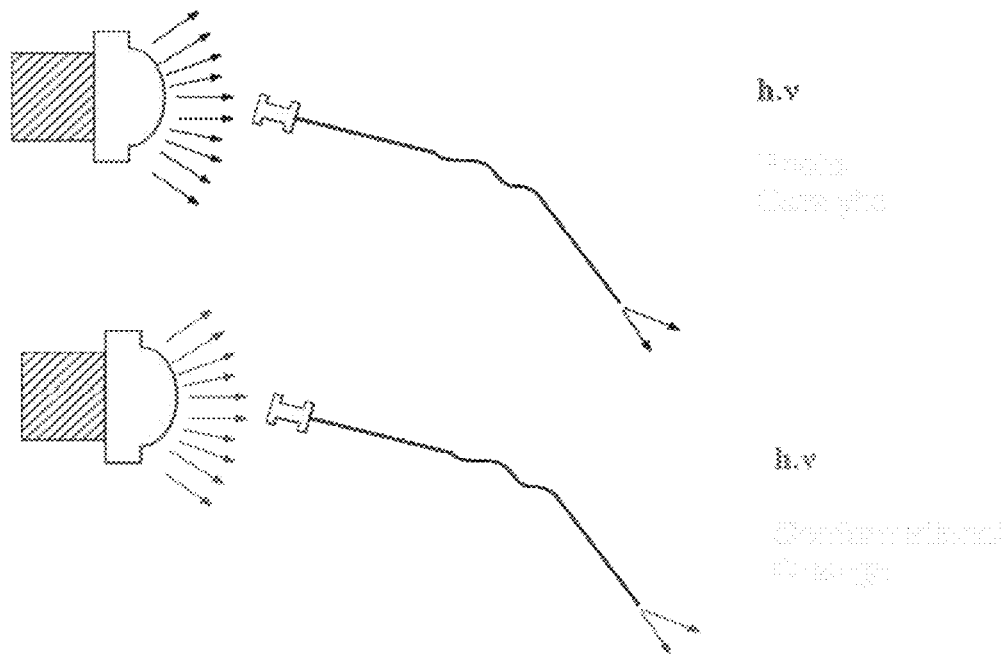
FIG. 9 is a schematic of a test set up devised to channel an external radiation source into the x-ray radiation system.
Figure 10:
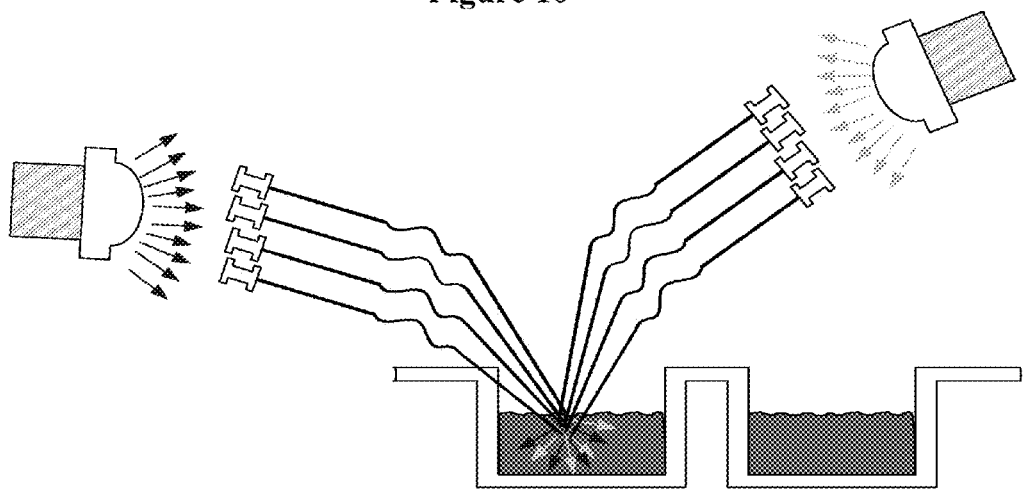
FIG. 10 is a schematic of a weakly coupled fiber bundle for combining different wavelengths of ionizing and non ionizing radiation.

A non-limiting illustration of how photo-catalytic light can work cooperatively with non ionizing radiation to potentiate the activation of bio-therapeutics is provided in FIG. 8. A test set up was devised to permit channeling of external radiation source into the x-ray radiation system as illustrated in FIG. 9. The weekly coupled fibers coupled red light and while light, UV light, and LASER light (from outside the irradiator) to the inside of the irradiator where the X-Ray energy was turned on. FIG. 10 provides an illustration of the weakly coupled fiber permitting different wavelengths of ionizing and non-ionizing radiation to be applied in conjunction with X-Ray. While the sample depicted in FIG. 10 is inside a petri dish, the concept relates to any sample regardless of the environment where the activation occurs.

Figure 2:
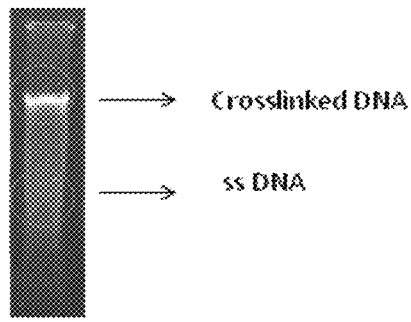
FIG. 2 is a schematic depicting the signals associated with crosslinked DNA and the signal associated with single strand DNA (represented by the smear pattern)
Figures 1, 11A:
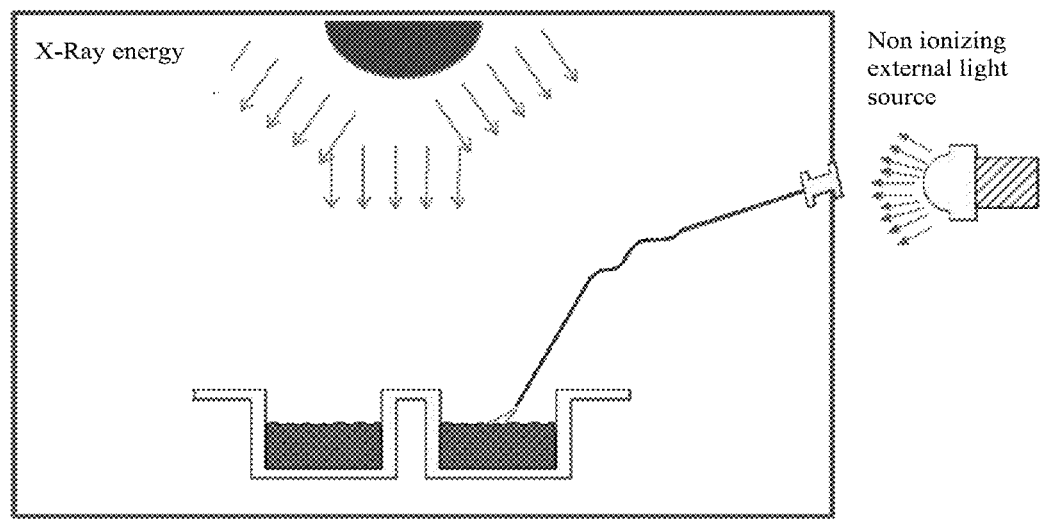
FIG. 11A-1 is a schematic of the combination of X-Ray and a fiber optic for simultaneous use of X-Ray energy with external light sources having potentiating effects.
Figures 2, 11A:
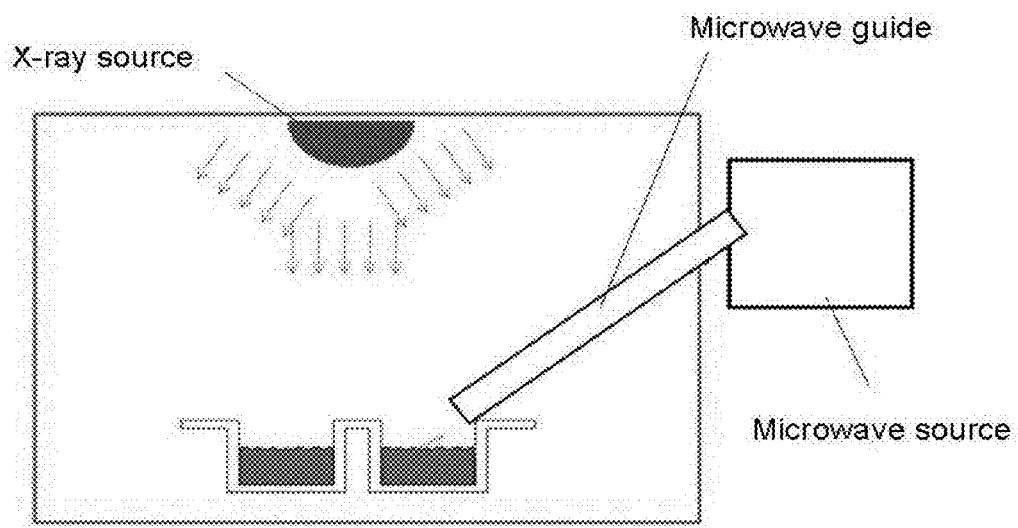

In one embodiment of this invention, various colors can be used to optimize an X-ray irradiation treatment. For example, the application of photo-catalytic energy can be done in conjunction with energy able to induce conformational changes in certain reactive site (i.e., a target site). FIG. 11A-1 illustrates the combination of X-Ray and a fiber optic allowing the simultaneous use of X-Ray energy with external light sources having potentiating effects. FIG. 11A-2 illustrates the combination of X-Ray and a microwave guide allowing the simultaneous use of X-Ray energy and microwave energy to interact with a target or reactive site.

Accordingly, as noted above, in one embodiment of this invention, there is provided a system or method for light stimulation within a medium. The system has a reduced-voltage x-ray source configured to generate x-rays from a peak applied cathode voltage at or below 105 kVp, and a first plurality of energy-emitting particles in the medium which, upon radiation from the x-ray source, radiate at a first lower energy than the x-ray source to interact with photoactivatable agent(s) in the medium. The method accordingly introduces a first plurality of energy-emitting particles into the medium, radiates the first plurality of energy-emitting particles in the medium with x-rays generated from a peak applied cathode voltage at or below 105 kVp, and emits a first lower energy than the x-ray source to interact with photoactivatable agent(s) in the medium. In various aspects to the invention the peak applied cathode voltage is at or below 120 kVp, is at or below 105 kVp, is at or below 70 kVp, is at or below 60 kVp, is at or below 50 kVp, is at or below 40 kVp, is at or below 30 kVp, or is at or below 20 kVp, or is at or below 10 kVp or is at or below 5 kVp. In one aspect of the invention, the distance to the target is utilized to also alter the effect of varying the incident energy of the X-rays incident on the medium. The distance can be set to a value of less than 5 mm, less than 10 mm, less than 15 mm, or less than 20 mm. In other embodiments, the x-ray source can be positioned farther away from the target being irradiated.

"kVp" is peak accelerating voltage applied in an X-ray tube between the cathode and anode. The term and its definition derive from the fact that in some systems the accelerating potential is not constant, but varies over time (i.e., have a voltage ripple). The kVp (in units of kilovolts) is the kinetic energy (in keV) of the most energetic electrons arriving at the anode, and also the energy of the most energetic X-ray photon produced by bremsstrahlung.

The efficiency of X-ray production by bremsstrahlung increases with increasing kVp, and so therefore does X-ray tube output. If the kVp (in kilovolts) is higher than the binding energy of an electron shell of the X-ray tube target material, it is possible for the electron to ionize that shell and for characteristic radiation to be produced.

For any given kVp, the X-ray spectrum contains a spread of energies, the highest of which is proportional to the kVp. However, the number of photons in lower energy ranges is greater than at the very highest energies, and the average energy of the X-ray beam is lower than the kVp. Nonetheless, the average energy increases with increasing kVp and the beam becomes more penetrating.

Figure 11B:
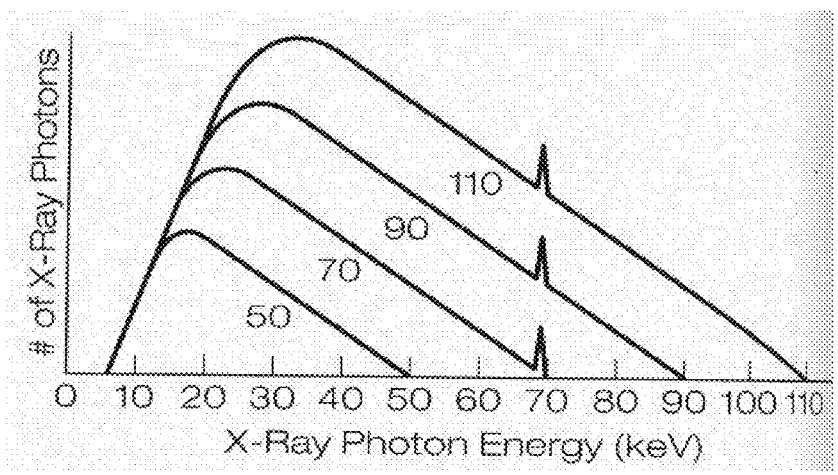
FIG. 11B is a schematic of x-ray spectra for various kVp.

FIG. 11B depicts the energy distribution of x-rays as a function of kVp. It shows a progressive reduction in the peak x-ray energy and a reduction in the number of x-rays as kVp is reduced. Accordingly, the computer system 5 shown in FIG. 1 (or another x-ray source controller) controlling the initiation energy source can control the kVp setting to change the dose and average x-ray energies incident on a target of subject 4. While the x-ray energy used in the experimental results below were obtained without an aluminum filter on the x-ray source, an aluminum or other filter can be used to truncate a portion of the x-ray spectrum and selectively provide different x-ray doses and x-ray energies to the target.

Figure 12A:
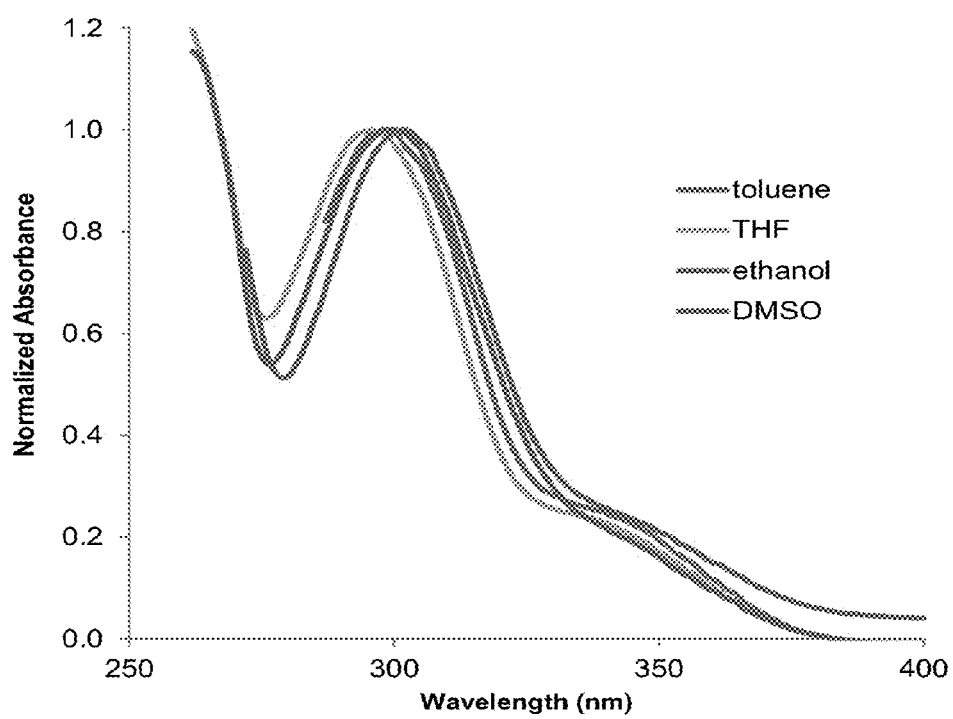
FIG. 12A is a schematic of the absorption of psoralen measured in different solvents and over a broad range extending from the UVB, the UVAnd part of the visible.

Regardless of method of treatment, psoralen is of interest for many of the biological applications of this invention. The absorption of psoralen was measured in different solvents including toluene, tetrahydrofuran (THF), ethanol, and dimethyl sulfoxide (DMSO). The UV-Vis absorption spectra is provided in FIG. 12A. In particular, FIG. 12A shows the absorption spectrum of psoralen measured in different solvents and over a broad range extending from the UVB, the UVAnd part of the visible.

The UV light emitted inside a cell or inside an organ depends on the inherent light conversion capability of the utilized particle and on the number of particles residing close to the point of measurement. The higher the number of particles the higher the net intensity according to the superposition principles applicable to light in particular and to electromagnetic waves in general. The nano-particle conversion material can be selected to have a high probability of interaction with X-ray and strong emission in UV range with as much intensity as possible. Alternatively, the nano-particle conversion material can be a scintillator selected to have a high probability of interaction with an ionizing particle and strong emission in UV range with as much intensity as possible. A scintillator is a material which exhibits luminescence when excited by ionizing radiation, such as for example an incoming particle (electron or ion), absorb its energy and reemit the absorbed energy in the form of light.

Some phosphors can be doped with ionic species such that the material formed can exhibit fluorescence and phosphorescence at the same time. The materials can be formed in single crystal or poly-crystalline forms, in powders or monoliths.

However, once the conversion material selection is done, further improvement of intensity solely depends on the size, the number and the distribution of the nano-particles that are close to target or to the measurement point. The delivery of particles inside an organ can be gated by the organ's vasculature. The delivery of particles inside a cell can also be gated by the ion channels residing in the cell walls. Organs can accept larger particles than cells since the openings gated by the organ's vasculature is much larger than ion channels in the cell walls.

One embodiment of this invention deals with the delivery of phosphors or scintillators or a combination thereof having particle sizes below 40 nm and that can pass through the ion channels of cells. Once inside the cell, the phosphors of this invention are trapped in sufficient concentration. The entrapment of the phosphors of this invention can be facilitated by the combination of applying a magnetic coating to the particles and using magnetic fields that are imposed externally to a given mammalian body (or external to an artificial medium). In addition to entrapment of phosphors or scintillators or a combination thereof inside cells or organs, the phosphors of this invention can be made to assemble in patterns that increase their net UV light output under X-Ray excitation.

In one embodiment, there is provided a system for light stimulation within a medium. The system has a first plurality of light-emitting particles which upon encountering an appropriate initiating excitation of light energy or particle beam energy radiate an output energy having photocatalysis potential to activate photoactivatable agents with minimized impact on the medium. The system further has a second plurality of light-emitting particles which upon encountering the same appropriate initiating excitation of light energy or particle beam energy radiate an output energy complementary to the output of the first set of particles A combination of energy emission from the first and second plurality of energy emitting particles produces a combined energy capable of activating chemical agents inside the medium more effectively than the first set of particles alone. The two sets of particles are interoperably complimentary to one another. The energy outputs can be of different natures. The first set of particles can output light energy and the second set of particles can output chemical energy.

The energy spectrum of the first set of particles has an energy distribution having a peak position in common with a peak in an absorption spectrum of the photoactivatable agent(s) and having a bandwidth overlapping the absorption spectrum of the photoactivatable chemical agents. The second energy potentiates the photoactivation by predisposing reactive sites to the photoactivatable chemical agent(s). The second energy can also be a light energy of different spectrum or a chemical energy resulting in the favorable alteration of the reaction potential of select reactive sites. For instance, light can cause excitation of photosensitizers, in the presence of oxygen, to produce various toxic species, such as singlet oxygen and hydroxyl radicals. Meanwhile, microwave and RF energy leads to dipolar alignment of molecular species having an asymmetrical charge distribution over their length.

More specific methods by which chemical pathways of photoactivatable chemistries can be altered is described below in at least the photo-treatment section and the photobiomodulation section.

Accordingly, in one embodiment of the invention, there is provided a method for light stimulation within a medium. The method includes introducing a first plurality of light-emitting particles into the medium, introducing a second plurality of light-emitting particles into the medium, exposing the first plurality of light-emitting particles to an initiating excitation of light energy or particle beam energy to produce from the first plurality of light-emitting particles a first output energy having photocatalysis potential to activate photoactivatable agents in the medium, and exposing the second plurality of light-emitting particles to an initiating excitation of light energy or particle beam energy to produce from the second plurality of light-emitting particles a second output energy complementary to the first output. A combination of energy emission from the first and second plurality of energy emitting particles produces a combined energy capable of activating chemical agents inside the medium.

One attribute of this invention is to provide phosphor materials capable of specific light outputs under X-Ray excitation in the absence of line-of-sight access to the external energy source.

A further attribute of this invention is to provide a set of phosphor or scintillator particles or a combination thereof that has a combined light output spectrum closely matching the absorption of a photoactivatable agent.

Another attribute of this invention is to provide phosphor or scintillator particles or a combination thereof capable of being oriented under an applied magnetic field.

Another attribute of this invention is to provide phosphor or scintillator particles or a combination thereof capable of being oriented under an applied electric field.

Another attribute of this invention is to provide self assembly of nanoparticles under an applied magnetic or electric field. In this attribute, the assembly of phosphor or scintillator or a combination thereof particles can form simple geometrical patterns such as dendrites, spherical clusters and rings.

Another attribute of this invention is to provide a method by which a set amount of phosphor or scintillator particles or a combination thereof yield more intensity at a targeted site than would occur the same amount of randomly distributed phosphor particles.

Another attribute of this invention is to provide a method by which two or more phosphors or scintillators or a combination thereof each emitting an intrinsic spectral signature, can be mixed or alloyed to form a particle mixture yielding a specific emission spectral signature.

Another attribute of this invention is to provide a method by which a particle mixture has a specific spectral signature matching a specific absorption of a photoactivatable agent, e.g., a photo-catalyst agent or bio therapeutic agent.

Another attribute of this invention is to provide a method by which a particle mixture has a specific spectral signature to activate two photo catalysts or two bio-therapeutic agents.

Another attribute of this invention is to provide a method by which a particle mixture acts as the carrier for the photo-catalyst of a bio-therapeutic agent.

Another attribute of this invention is to provide a method by which phosphor or scintillator particles or a combination thereof can be made to emit a single specific wavelength to actuate specific biological functions or can be used to assist or block intracellular communication.

Another attribute of this invention is to provide a method by which phosphor particles or scintillator particles of a sufficiently small size are delivered to an organ, to a cell, or to an inside of the cell nucleus and then are trapped inside the target using magnetic fields.

The phosphors or scintillator particles of this invention can be synthesized from known material chemistries that possess the capability of fluorescence (caused by the instantaneous decay of electrons from a high energetic state to a lower one) or phosphorescence (delayed decay of electrons from a high energetic state). A comprehensive set of chemistries is provided.

The phosphors or scintillator particles of this invention can be further prepared using additive processes (i.e.; coatings) to gain the self assembly capability inside cells when exposed to electrical field or magnetic fields stimulation. Externally imposed electrical field or magnetic fields can be applied in a cyclic manner of specific frequencies and magnitudes that promote the assembly into patterned configurations.

Besides phosphors and scintillator particles, this invention can also use other light emitting particles such as fluorescent particles and up-converting particles. In those cases, the techniques described here for improving the efficiency of delivering light to a target or for spectrally matching the emitted light to a photoactivatable substance still apply. Various fluorescent particles and up-converting particles are described in the related applications listed above. Moreover, the light emitters of the invention can utilize plasmonic metallic shell structures to increase the efficiency of absorption and light emission, as described in the related applications listed above.

Some of the materials of interest include phosphors such as YTaO4, YVO$_4$, YNbO$_4$ and CaWO$_4$. Each of these lattice structures is an effective X-Ray absorber and a strong UV emitter. The absorption spectra exhibit strong and broad bands in the UV. The transition involved in these lattices is typically the result of a charge transfer from the oxygen to the d0 ion. An electron can be excited from a non-bonding orbital on the oxygen to an anti-bonding orbital (d on the metal ion). Another lattice structure of interest is Y$_2$O$_3$. All of these materials have been doped using ionic species to create color centers. Y$_2$O$_3$ can be doped with Gd and YTaO$_4$ can be doped with Nb. The specific influence of the host lattice on the luminescent center is different for different materials. This is not surprising since the direct surrounding of the luminescent center is changed. The influence of the lattice on optical centers is relatively well known for some materials such as YF$_3$:E$^{3+}$ and Y$_2$O$_3$3:Eu$^{3+}$.

One of the first factors is covalency. A high covalency translates to reduced interactions between electrons since they spread out over wider orbitals. Electronic transitions between energy levels are set by the difference in these energy levels which are in turn gated by electronic interactions. The difference in energy levels is lower for increasing covalency. Another factor for the influence of the lattice on the optical properties of an ion is the crystal field. Certain optical transitions are determined by the strength of the crystal field. This explains why Cr$_2$O$_3$ is green but Al$_2$O$_3$:Cr$^{3+}$ is red even though both materials have the same crystalline structure. The Cr$^{3+}$ ions occupy the smaller Al$^{3+}$ sites and as a result feel a stronger crystal filed in Al$_2$O$_3$ than in Cr$_2$O$_3$. The synthesis of the materials influences the emission of the color centers. The defects as well as the particle size and particle size distribution all play a role.

Controllable and repeatable processes that can be utilized to produce nano-particles, and use thereof, have emerged as an area of science and engineering of considerable interest in recent years. The use of electric or magnetic field-assisted transport offers an approach for manipulating millimeter, micrometer and nanometer particles in a repeatable and controllable manner. The use of such electric fields is generally referred to as dielectro-phoresis (DEP).

The application of a field gradient gives rise to translation and orientation of particles exhibiting dipolar characteristics. The net asymmetrical distribution of charge along the dimension of a particle dictates the magnitude of the resultant dipole which has units of unit charge per unit length or Coulomb/meter. The same is true for magnetic fields as well as electric fields. In magnetic fields, this effect is characterized by the susceptibility of the material forming the particle. The net magnetization per unit length will define the strength of the magnetic dipole.

Phosphor or scintillator particles, such as those made of oxide materials, do not have a net dielectric dipole or magnetic dipole. However, according to one embodiment of the invention, phosphor or scintillator particles can be made to act in a dipolar fashion.

Phosphor selection criterions for this invention are based on peak intensity of the emission, peak position with UV of the emission, the need to have a workable phosphor with minimal storage requirements, handling and packaging, the ability of the phosphor to couple to X-Ray energy, the control over its particle size and particle size distribution; and, finally their surface chemistry.

In one embodiment of the invention, the peak emission target is between 310 nm and 800 nm or simply the UVA spectrum. It is desirable to have the maximum conversion of X-ray intensity into UVA intensity and visible light (see Table 6 in FIG. 12B).

This conversion can be characterized in various interrelated terms. Sometimes the conversion is referred to as the quantum yield or probability of interaction between X-ray and phosphors. These interrelated terms include the coupling efficiency, emission effectiveness or the Effective-Z between the X-ray and the phosphor. A list of some of the X-ray phosphors emitting in the VIS range is reported in Table 7 in FIG. 12C.

Alternatively, as noted above, a variety of scintillator materials can also be used including organic scintillators, plastic scintillators, and inorganic crystals.

Organic scintillators are usually aromatic hydrocarbon compounds which contain benzene ring structures interlinked in various ways. Their luminescence typically decays within a few nanoseconds. Some organic scintillators are pure crystals. The most common types are anthracene (C$_{14}$H$_{10}$, decay time≈30 ns), stilbene (C$_{14}$H$_{12}$, few ns decay time), and naphthalene (C$_{10}$H$_8$, few ns decay time). These organic crystal scintillators are very durable, but their response is anisotropic. Anthracene has the highest light output of all organic scintillators Plastic scintillators are solutions of organic scintillators in a solvent which is subsequently polymerized to form a solid. Some of the common solutes are p-Terphenyl, PBD, b-PBD, PBO, POPOP. The most widely used plastic solvents are polyvinyltoluene and polystyrene. Plastics scintillators give a fast signal (a few ns) and a high light output. The number of emitted scintillation photons is best described by the convolution of an exponential decay and a Gaussian (rather than the exponential decay alone).

Plastics by their nature can very easily be shaped and machined to the forms (cylinders, rods, flat sheets, fibers, microspheres and thin films) and are relatively inexpensive. Plastics scintillators, while generally resistant, can be scratched and attacked by organic solvents (e.g. acetone). Also, bodily acids can cause cracking over time. Nonetheless, in one embodiment of the invention, plastic sheet scintillators can be inserted around or near a tumor site to provide light emission upon exposure to an electron beam.

Inorganic scintillator crystals include materials such as tungstates and alkali metal halides, often with a small amount of activator impurity. The most widely used inorganic scintillator crystal is NaI(Tl) (sodium iodide doped with thallium). Other inorganic alkali halide crystals are: CsI(Tl), CsI(Na), CsI(pure), CsF, KI(Tl), Li(Eu). Some non-alkali crystals include: $BaF_2$, $CaF_2(Eu)$, ZnS(Ag), $CaWO_4$, $CdWO_4$, YAG(Ce) ($Y_3Al_5O_{12}(Ce)$), BGO bismuth germanate, GSO, LSO, $LaCl_3(Ce)$, $LaBr_3(Ce)$.

A disadvantage of some inorganic crystals, e.g., NaI, is their hygroscopicity, a property which requires them typically to be housed in an air-tight enclosure to protect them from moisture. CsI(Tl) and $BaF_2$ are only slightly hygroscopic and do not usually need protection. CsF, NaI(Tl), $LaC_{13}(Ce)$, $LaBr_3(Ce)$ are hygroscopic, while BGO, $CaF_2$(Eu), LYSO, and YAG(Ce) are not. The hygroscopic inorganic crystals for application in this invention would typically be encapsulated with a silica or plastic.

Like the phosphors above, scintillators each show typical emission peaks. $BaF_2$ or barium fluoride is reported to emit in the UV band (220 nm) and at longer wavelengths (310 nm) and has a 630 ns decay time. $BaF_2$ is not hygroscopic. CaF has a reported emission at 390 nm. $CaF_2(Eu)$ or calcium fluoride doped with europium is not hygroscopic, has a 940 ns decay time, and has been reported to have an emission centered at 435 nm. BGO or bismuth germanate has a higher stopping power, but a lower optical yield than NaI(Tl). BGO has emission centered at 480 nm. $CdWO_4$ or cadmium tungstate has a relatively high light output (about ⅓ of that of NaI(Tl)). $CdWO_4$ has been reported to have an emission centered at 475 nm. $CaWO_4$ or calcium tungstate has been reported to have emission at centered at 420 nm. CsI(Tl) or cesium iodide doped with thallium crystals have been reported as one of the brightest scintillators. The maximum wavelength of light emission is centered at 550 nm. CsI(Tl) is only slightly hygroscopic. CsI(Na) or cesium iodide doped with sodium is less bright than CsI(Tl), but comparable in light output to NaI(Tl). The wavelength of maximum emission is at 420 nm. CsI(Na) is hygroscopic. CsI undoped cesium iodide emits predominantly at 315 nm, and is only slightly hygroscopic. The light output is relatively low. $LaBr_3(Ce)$ (or lanthanum bromide doped with cerium is an alternative to NaI(Tl). $LaBr_3(Ce)$ has been reported to have emission at centered at 370 nm. It is hygroscopic. $LaCl_3(Ce)$ (or lanthanum chloride doped with cerium) is an alternative to $LaBr_3(Ce)$. It is hygroscopic. It has been reported to have emissions centered at 350 and 390 nm.

U.S. Pat. No. 7,084,403 (the entire contents of which are incorporated herein by reference) shows a variety of emission from lanthanum halides. FIG. 14B (reproduced from '403 patent) is a schematic of emission spectra under X-ray excitation for different lanthanum halide scintillators.

$PbWO_4$ or lead tungstate has a high stopping power. It has emission at 420 nm. $LuI_3$ or lutetium iodide has emission at 420 nm. LSO or lutetium oxyorthosilicate ($Lu_2SiO_5$) has emission around 420 nm. GSO or gadolinium oxyorthosilicate ($Gd_2SiO_5$) has emission around 430 nm. However, as reported by Mao et al., in "Emission Spectra of LSO and LYSO Crystals Excited by UV Light, X-Ray and (-ray," in IEEE TRANSACTIONS ON NUCLEAR SCIENCE, VOL. 55, NO. 3, June 2008, the emission spectrum shifts depending on the source of excitation. Accordingly, in one embodiment of this invention, the choice of excitation source can be used to peak match to a particular photoactivatable substance such as to match the peak in the psoralen absorption.

LYSO ($Lu_{1.8}Y_{0.2}SiO_5(Ce)$) has a broad emission around 425 nm. LYSO is non-hygroscopic. NaI(Tl) or sodium iodide doped with thallium. NaI(Tl) is the most widely used scintillator material. It has an emission around 410 nm. NaI(Tl) is hygroscopic. YAG(Ce) or yttrium aluminum garnet: YAG(Ce) is non-hygroscopic. The wavelength of maximum emission is around 550 nm. Its light output is about ⅓ of that of NaI(Tl). ZnS(Ag) or zinc sulfide has emission at 450 nm. $ZnWO_4$ or zinc tungstate has a peak emission at 480 nm (with emission range between 380-660 nm).

In one embodiment of the present invention, mixtures of these scintillators can provide a spectral output for photoactivation of photoactivatable agent(s) such as psoralen. In one embodiment of the invention, the amounts of each particular scintillator mixed into the composition is a weighted sum where the product of the emission intensity of each scintillator and the weight composition percentage provides at each emission wavelength a predetermined component of a spectral emission band. In one embodiment of the invention, light from the composition of scintillators simulates at least a part of an absorption spectrum of the photoactivatable agents. For example, a wavelength distribution of the light from the composition of scintillators can have a peak position in common with one of the peaks in the absorption spectra of the psoralens in different media. Further, the wavelength distribution of the light from the composition of scintillators can simulate an absorption edge of the absorption spectrum of the photoactivatable agents, such as for example the absorption edge to the higher wavelength side of the peaks. Further, the wavelength distribution of the light from the composition of scintillators can overlap the absorption spectrum of the photoactivatable agents in part or in whole as if a replicating the absorption spectra.

UVA/UVB Emissions:

In some applications, the desirable incident or initiation energy is different than X-ray (such as EUV) while the desirable down-converted output intensity remains in the UVAnd the visible. In other applications, the desirable incident or initiation energy is X-ray but the desirable down-converted energy output of the phosphor is in the UVB. Yet, in other cases, the desirable incident or initiation energy is X-ray but the desirable down-converted energy output of the phosphor is in the UVAnd the UVB or the UV and the visible.

According to one embodiment of the invention, phosphors were selected to work with excitation sources including X-Ray, Extreme UV and e-beam. Within the X-ray regime, the selected phosphors can couple to a flux of X-ray photons emanating from commercially available equipment sources used for therapeutic tumor treatments, medical imaging and semiconductor inspection.

Figure 13A:
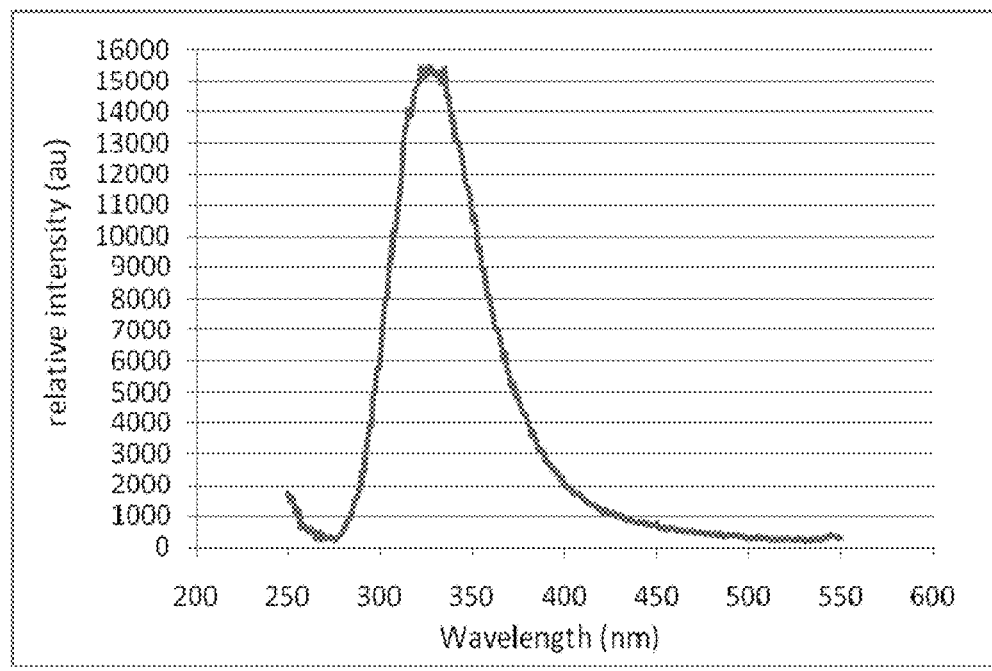
FIG. 13A is a schematic of the spectral emission of $YTaO_4$ (reported to have a peak emission at 337 nm under X-Ray excitation) showing emission at 327 nm.
Figure 13B:
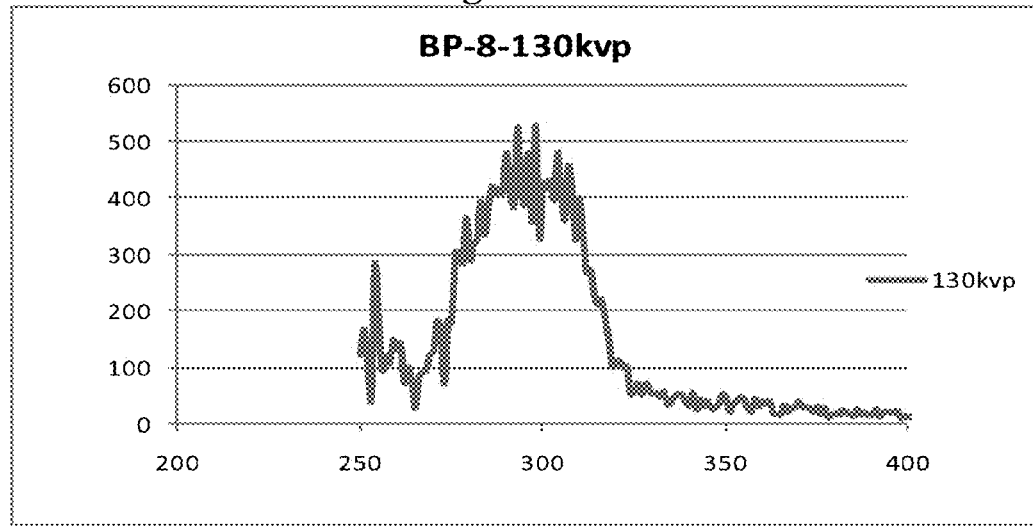
FIG. 13B is a schematic of the spectral emission of $LaF_3$:Ce (reported to have a peak emission at 337 nm under X-Ray excitation) showing emission at 300 nm.

One example of a material that emits in the UVA regime is provided in FIG. 13A. The X-ray system used to carry out the excitation was the Faxitron X-Ray System. (Faxitron X-Ray LLC, 575 Bond St. Lincolnshire, Ill. 60069 USA). FIG. 13B is a schematic of emission from $YTaO_4$ reported to have a peak emission at 337 nm under X-Ray excitation. However, here, emission at 327 nm was observed.

Figure 13C:
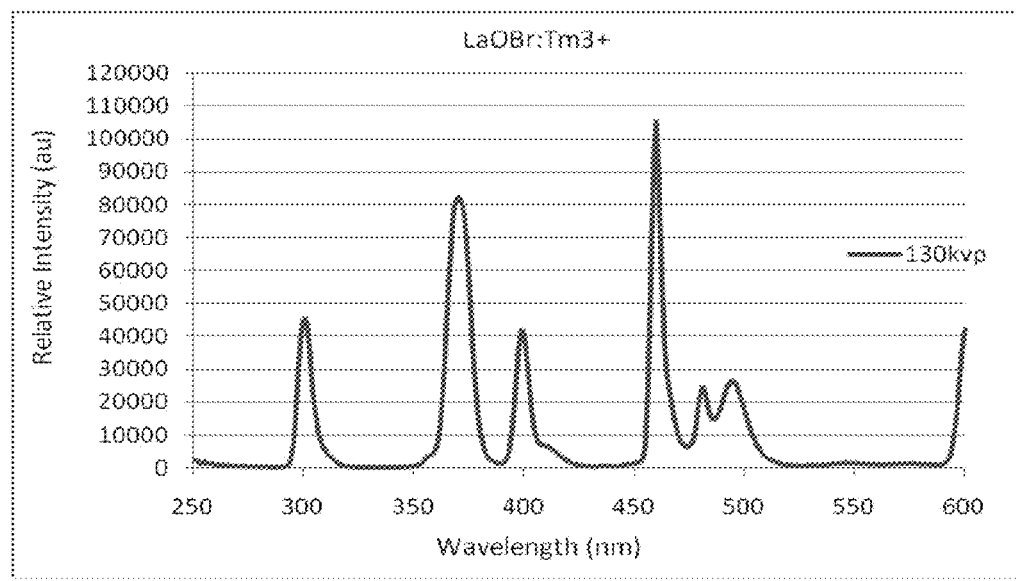
FIG. 13C is a schematic of the spectral emission of LaOBr:$Tm_3^+$ coated with silica suitable for a phosphor chemistry capable of emission in the UVB, UVA and the visible light regions.

One example of a material having an output in the UVB is provided in FIG. 13C. FIG. 13C is a schematic of emission from LaOBr:Tm$_3^+$ reported to have a peak emission at 280 nm under X-Ray excitation. However, emission at 300 nm was observed in work by the inventors.

Figure 13D:
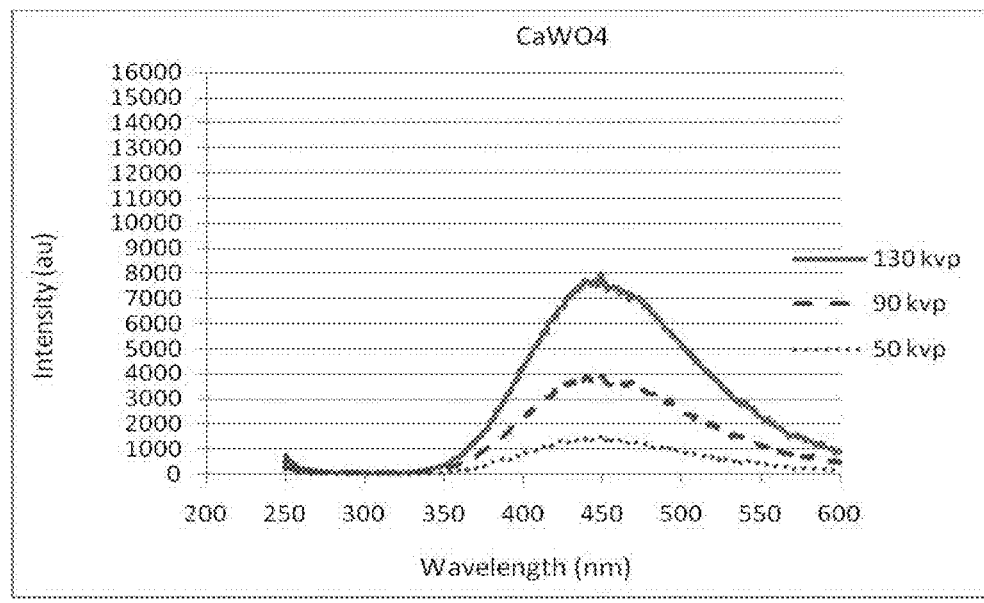
FIG. 13D is a schematic of the spectral output of a visible $CaWO_4$ phosphor under X-Ray excitation from different energy level and different flux x-rays.

One example of a material having an output in the UVA, UVB and the visible is provided in FIG. 13D. FIG. 13D is a schematic of emission from a CaWO$_4$ phosphor coated with silica and showing emission in UVB, UVA, and the visible.

Impact of X-ray on UV Output Intensity:

The initiation energy (X-Ray in this example) influences the UV output of the phosphor. Both the intensity of X-Ray and the energy of the X-Ray photon excitation influence the UV light output. The following examples are provided to illustrate how modifying the photonic energy and intensity of X-Ray can modulate the light output of the UV and Visible light. These tests were made using three different voltages between the filament and the tungsten target of the X-ray generator. In each case, the emission peak and intensity of the phosphor emission was dependent on the voltage between the filament and the target (i.e., dependent on the intensity of X-Ray and the energy of the X-ray photon excitation).

In these tests, various phosphors were weighed to 12 grams and placed in UV transparent containers. These phosphors were activated under X-ray generated using different voltages (50 kVp, 90 kVp and 130 kVp). The term "kVp" as before representing the peak voltage in kilovolts. A photo-spectrometer was placed in the same position vis-à-vis the various containers.

Figure 13E:
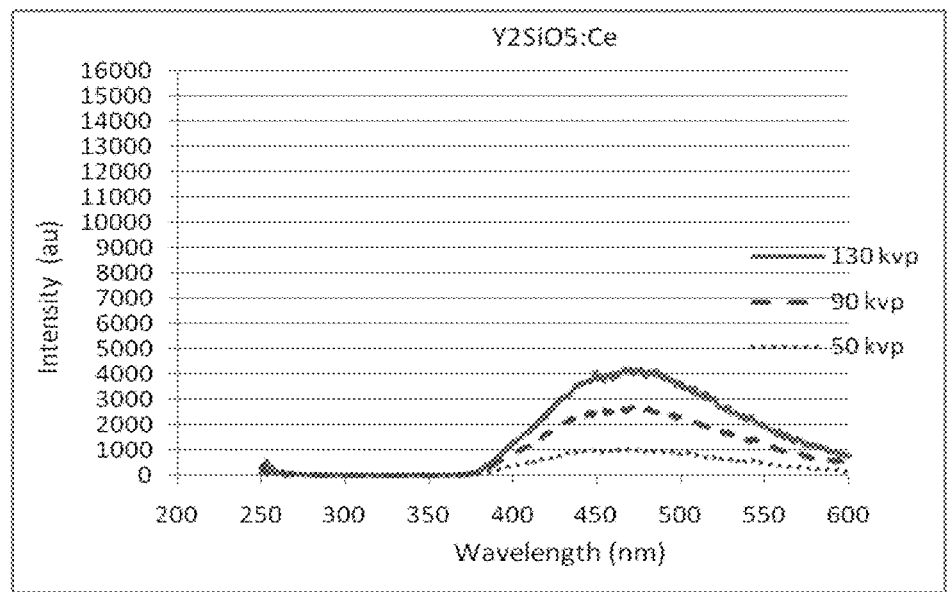
FIG. 13E is a schematic of the spectral output of a visible $Y_2SiO_5$:Ce phosphor under X-Ray excitation from different energy level and different flux x-rays.
Figure 13F:
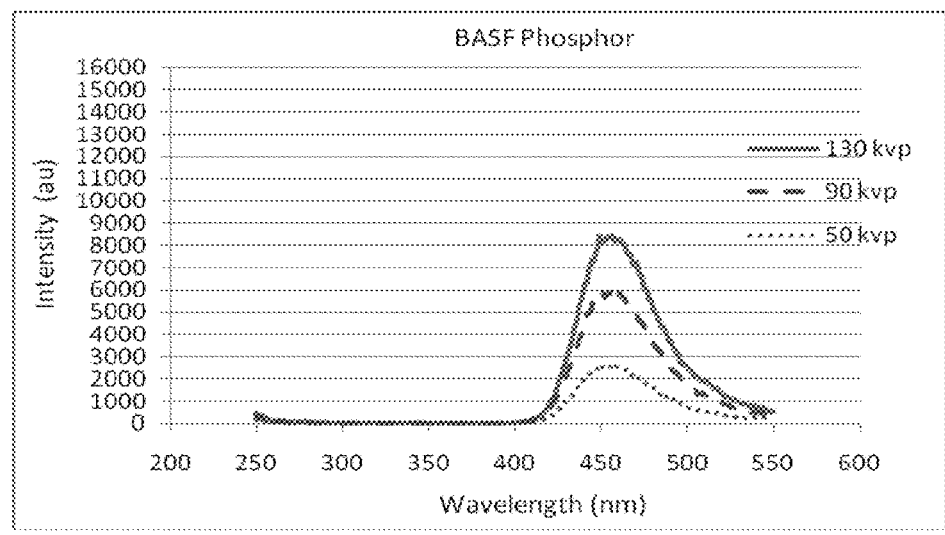
FIG. 13F is a schematic of the spectral output of a visible phosphor (BASF commercial phosphor XYMARA MARKER BLUE LF2A) under X-Ray excitation from different energy level and different flux x-rays.
Figure 13G:
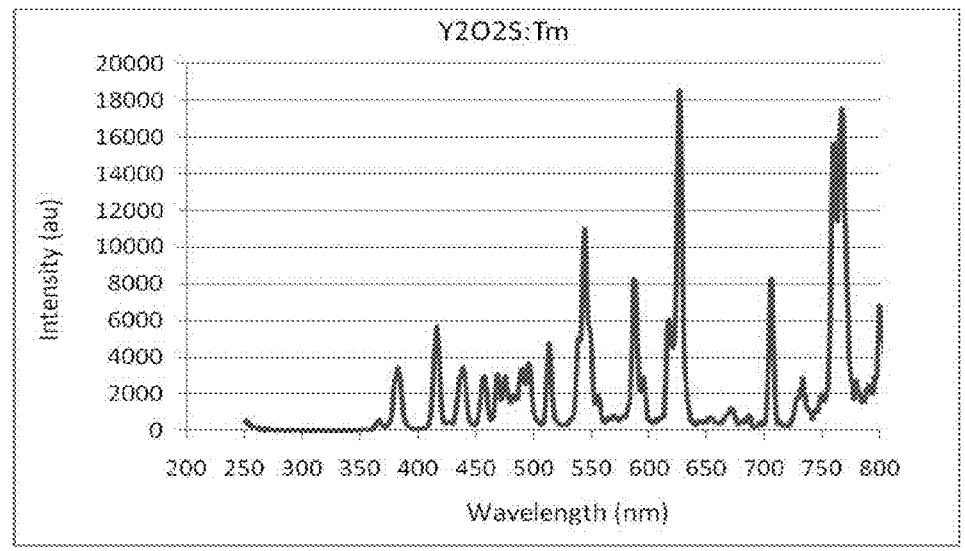
FIG. 13G is a schematic of the spectral output of a $Y_2O_2S$:Tm phosphor capable of emission in the UVAnd in the visible light regions.
Figure 13H:
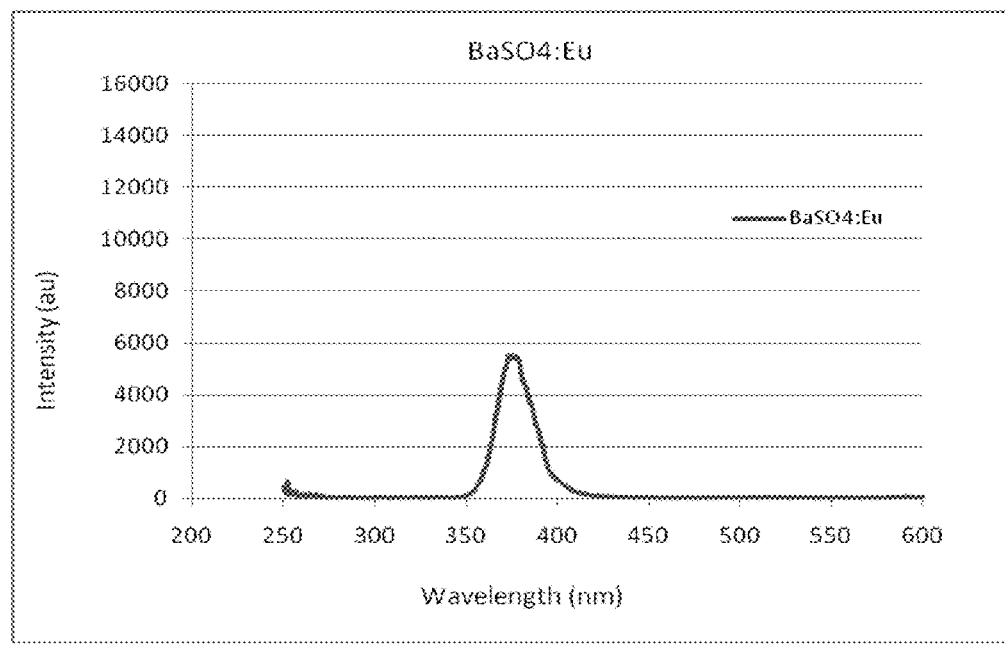
FIG. 13H is a schematic of the spectral output of a $BaSO_4$:Eu phosphor capable of emission in the UVAnd in the visible light regions.
Figure 13I:
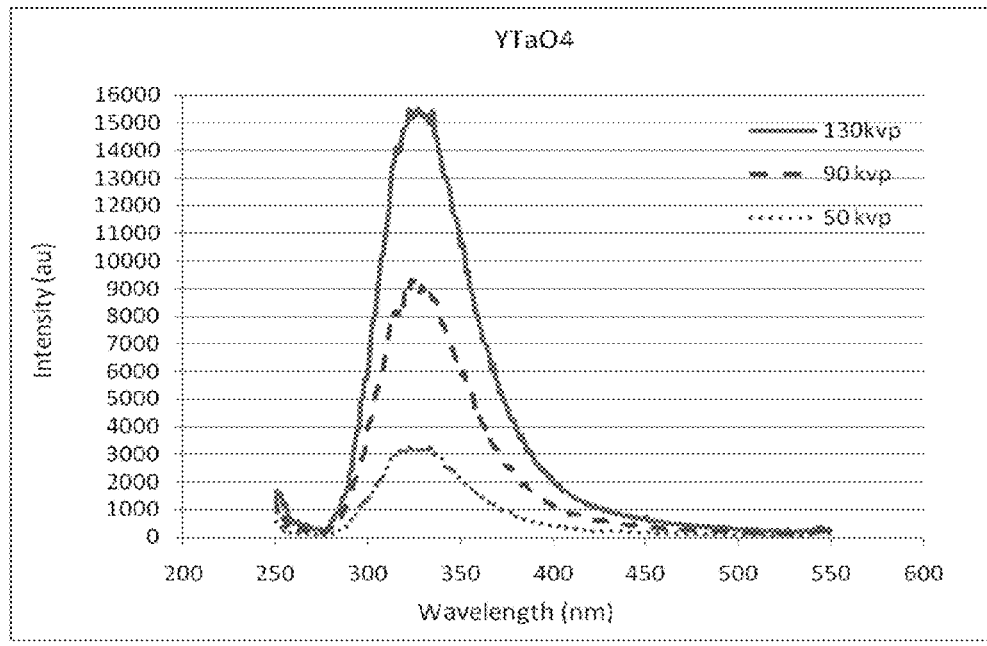
FIG. 13I is a schematic of the spectral output of a $YTaO_4$ phosphor capable of emission in the UVAnd in the visible light regions.
Figure 13I:
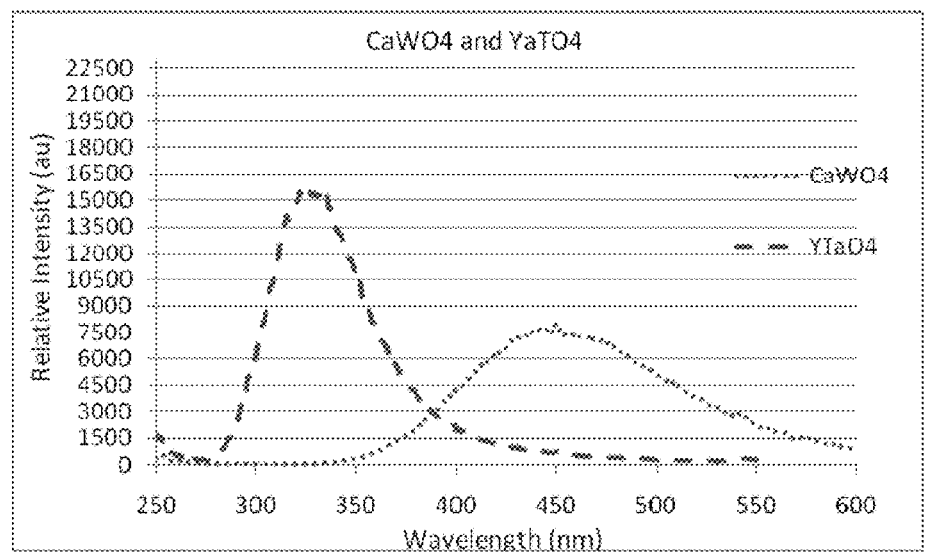

FIG. 13E is the spectral output from a visible phosphor Y$_2$SiO$_5$:Ce under X-ray excitation using three different voltages between the filament and the target. FIG. 13F is the spectral output of a visible phosphor (BASF commercial phosphor XYMARA MARKER BLUE LF2A) under X-Ray using three different voltages between the filament and the target of the X-ray generator. FIG. 13G is the spectral output of a visible phosphor Y$_2$O$_2$S:Tm under X-Ray using three different voltages between the filament and the target of the X-ray generator. FIG. 13H is the spectral output of a BaSO$_4$:Eu phosphor capable of emission in the UVAnd in the visible. FIG. 13I is the spectral output of a YTaO$_4$ phosphor capable of emission in the UVAnd in the visible. FIG. 13J-A is a schematic of the spectral output of a YTaO$_4$ phosphor chemistry capable of emission in the UVA and CaWO$_4$ capable of emitting in the UVA and in the visible.

A Mixed or Alloyed Configuration of the Invention

According to another embodiment of the invention, at least two phosphors are mixed to broaden the output of the mixture as compared to the individual starting phosphors. According to this embodiment, multi-peak output phosphors can be obtained from one phosphor chemistry or by combining multiple phosphor chemistries. All or any of the phosphor chemistries listed in Table 3 can be combined with one another to form multiple wavelengths of interest. These phosphors in Table 8 shown in FIG. 13J-B are listed in an ascending order of wavelength emissions.

In one embodiment of the invention, the amounts of each particular phosphor mixed into the composition is a weighted sum where the product of the emission intensity of each phosphor and the weight composition percentage provides at each emission wavelength a predetermined component of a spectral emission band. In one embodiment of the invention, light from the composition of phosphors simulates at least a part of an absorption spectrum of the photoactivatable agents. For example, a wavelength distribution of the light from the composition of phosphors can have a peak position in common with one of the peaks in the absorption spectra of the psoralens in different media shown in FIG. 12A. Further, the wavelength distribution of the light from the composition of phosphors can simulate an absorption edge of the absorption spectrum of the photoactivatable agents, such as for example the absorption edge to the higher wavelength side of the peaks in FIG. 12A. Further, the wavelength distribution of the light from the composition of phosphors can overlap the absorption spectrum of the photoactivatable agents in part or in whole as if a replicating the absorption spectra.

In one embodiment, the weighted product produces a spectral emission band which simulates a commercial UV light source. FIG. 13J-C provides a typical spectrum from a commercial UV light source which has been used to activate psoralens. As can be seen, the commercial UV light source has a broader spectral width than the absorption line of psoralen.

Given the uncertainties of the mechanisms of psoralen activation and association with the cancer cells for cell death, the broader spectral width of the commercial UV light source may offer advantages in activation of the psoralen and promotion of cancer cell death. For example, the broader spectral width of the commercial UV light source may itself promote changes in the cancer cells themselves which promote attachment of the "activated" psoralen. Laskin et al, in a paper entitled "Psoralens potentiate ultraviolet light-induced inhibition of epidermal growth factor binding," in Proc. Nat. Acd. Sci. vol. 83, pp. 8211-8212, November 1996, show in their FIG. 1 the effects of UV dose with and without trimethyl psoralen on inhibition of $^{125}$I-EGF specific binding. The inhibition of promoted with and without trimethyl psoralen at higher UVA light doses, but with higher efficiency with trimethyl psoralen present. Moreover, the data shows that doses of greater than 1 Joule/cm$^2$ seem required to activate a cell response without psoralen, while with psoralen the activation occurs at lower doses. Indeed, the dose to induce a cell response seems inversely proportional to the psoralen concentration, that is the higher the psoralen concentration the lower the dose needed to promote a cell response. Laskin et al concluded that psoralen/UVA or UVA light-induced changes in the kinase activity of an epidermal growth factor receptor may initiate a cascade of biochemical events leading to cellular responses.

Varga et al in "Dose-related Effects of Psoralen and Ultraviolet Light on the Cell Cycle of Murine Melanoma Cells," in Cancer Res 1982; 42:2223-2226, published online Jun. 1, 1982 reported similar results with Accordingly, in one embodiment of the invention, the mixed phosphors and scintillators of the invention provide a spectral response of higher UV dose and a closer spectral match to that of commercial UVA sources than for example single fluorescent emitters or single phosphor emitters.

Figure 13L:
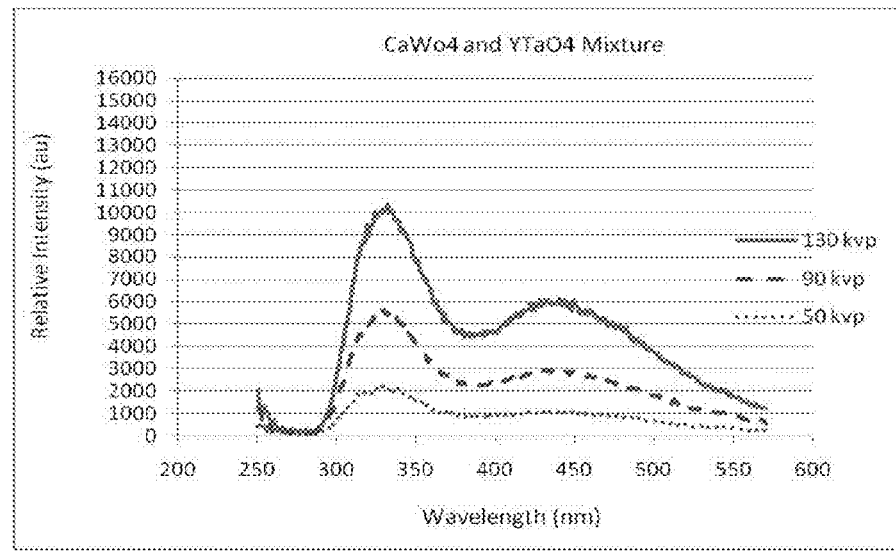
FIG. 13L is a schematic of the emission spectra under X-Ray excitation for the combination of $CaWO_4$ and $YTaO_4$ mixture.

FIG. 13K is the superimposed emission spectra under X-ray excitation for CaWO$_4$ phosphors and YTaO$_4$ phosphors. In the example illustrated in FIG. 13K, the two phosphors each emit in a distinct region. FIG. 13L is the emission spectra under X-ray excitation (for various voltages between the filament and the target) for the combination of a mixture of CaWO$_4$ and YTaO$_4$ phosphors. The spectral output demonstrates the ability to influence the output intensity of the mixture as compared to the staring materials. The intensity of the initiation energy (X-ray in this case) influences the UV output of the phosphor. The following examples are provided to illustrate how modifying the intensity of photonic energy of X-ray can modulate the light output of the UV and Visible light. The relative intensity output of a phosphor (CaOW$_4$) was measured as a function of the energy of the X-ray photons. The X-ray energy was intensified by modifying the peak voltages that exist between the filament and the target. The target in this case was Tungsten. The measurements were carried out using the same mass of phosphor under 50 kVp, 90 kVp and 130 kVp. The relative intensity of the emission in arbitrary units is indicative but not conclusive in terms of comparing different materials. However, within the same conditions used to conduct measurements, it is clear that the higher X-ray intensity the higher the relative intensity of the emitted wavelength.

According to one embodiment of the invention, phosphors are synthesized from different chemicals and using different processes to control their morphology, in turn influence their properties and light intensity output, but more importantly their stability in ambient air environments. It is preferred in certain applications to have phosphors that are not hygroscopic. Phosphors are easier to handle and to work with when the phosphors are stable in water and do not contain dopants that are toxic; however, even when phosphors are not stable in water and do contain dopants that are toxic, particles of these phosphors in one embodiment of the invention can be coated using chemistrical synthesis methods to build-up a protective coating which shields the phosphor from the environment (water for example) and which shields the environment from the toxic dopant in the phosphor (Bromide for example). The protective coating can be silica or can be diamond or diamond-like carbon. Silica can be formed using sol-gel derived techniques. Diamond and diamond-like carbon can be derived from chemical vapor deposition (CVD) techniques based for example on Hydrogen-Methane gas mixtures. The handling and packaging of various phosphors and phosphor mixtures can be achieved through dispersion in solution or in powder form. It was found that silica coated phosphors do not have a tendency to agglomerate.

Figure 14A:
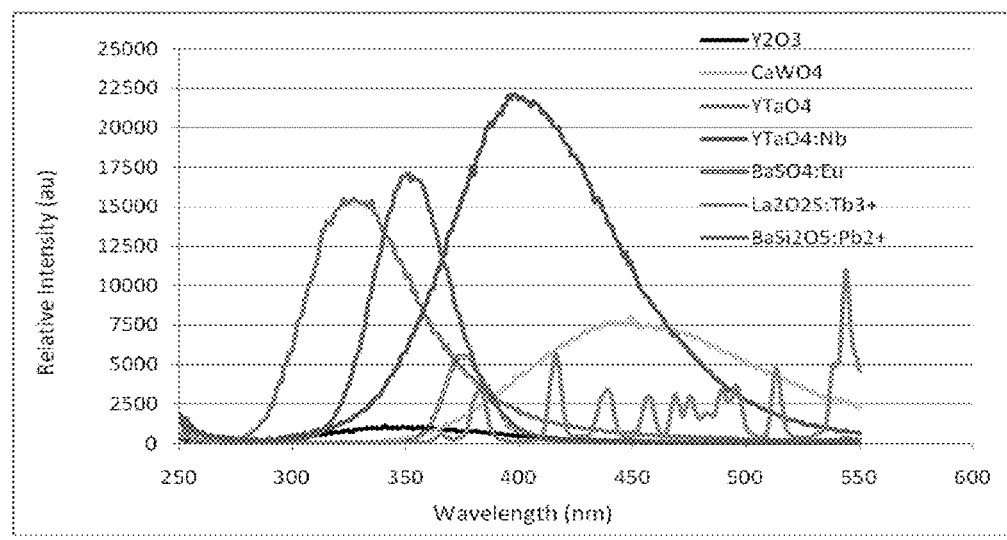
FIG. 14A is a schematic of the emission spectra under X-Ray for various materials including. $Y_2O_3$, $CaWO_4$, $YaTO_4$, $YaTO_4$:Nb, $BaSO_4$:Eu, $La_2O_2S$:Tb, $BaSi_2O_5$:Pb for various voltages between the filament and the target.
Figure 14B:
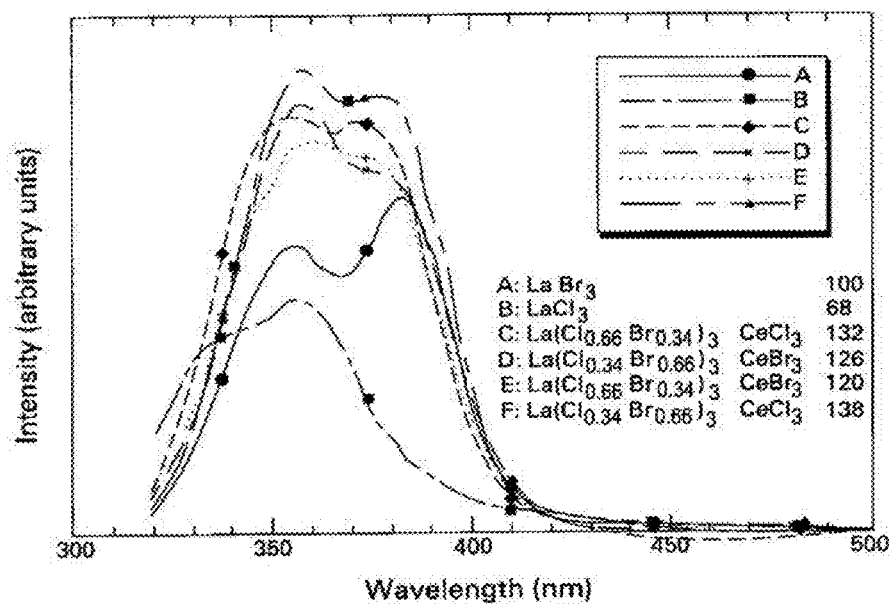
FIG. 14B is a schematic of emission spectra under X-ray excitation for scintillators.

FIG. 14A is the emission spectra under X-ray excitation for various materials including Y$_2$O$_3$, CaWO$_4$, YaTO$_4$, YaTO$_4$:Nb, BaSO$_4$:Eu, La$_2$O$_2$S:Tb, BaSi$_2$O$_5$:Pb. These materials yield various peak intensities and wavelengths. As seen from this figure, the phosphor and scintillator materials (CaWO$_4$, YaTO$_4$, YaTO$_4$:Nb, BaSO$_4$:Eu, La$_2$O$_2$S:Tb, BaSi$_2$O$_5$:Pb) are considerably brighter than that of Y$_2$O$_3$ a conventional fluorescent material.

Hence, in one embodiment, there is provided a system and method for light stimulation within a medium. The system includes an initiation source configured to an initiation energy and a plurality of energy-emitting particles in the medium which, upon radiation from the initiation source, radiate at a lower energy than the initiation source to interact with photoactivatable agents in the medium. The energy-emitting particles radiate with an intensity at least two times greater than that of intrinsic (or undoped) Y$_2$O$_3$, upon exposure of Y$_2$O$_3$ to the radiation from the initiation source. The method includes introducing a plurality of energy-emitting particles into the medium, radiating the plurality of energy-emitting particles in the medium with radiation from an initiation energy source, and emitting from the plurality of energy-emitting particles a lower energy than the radiation from the initiation energy source to interact with photoactivatable agents in the medium. In various aspects of the invention, the energy-emitting particles radiate with an intensity at least 10 times greater than that of intrinsic Y$_2$O$_3$, at least 50 times greater than that of intrinsic Y$_2$O$_3$, or at least 100 times greater than that of intrinsic Y$_2$O$_3$, or at least 500 times greater than that of intrinsic Y$_2$O$_3$, or at least 1000 times greater than that of intrinsic Y$_2$O$_3$.

In this and other embodiments, the plurality of energy-emitting particles can include at least one of phosphors, scintillators, fluorescent materials, and combinations and agglomerations thereof with or without plasmonic inducing agents. In this and other embodiments, the initiation energy source can be one of an X-ray source, a high energy source, a particle source, and extended UV source, and a radioactive source including at least one of a Cobalt 60 source, a Cesium-137 source, an Iridium-192 source, a Krypton-85 source, a Radium-226 source, and a Strontium-90 source or a combination thereof.

Figure 14C:
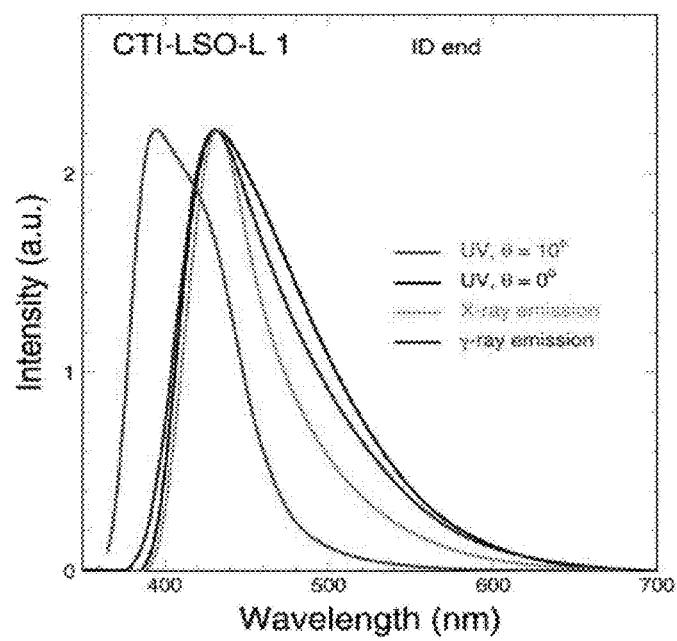
FIG. 14C is a schematic of emission spectra of lutetium oxyorthosilicate LSO under different excitation sources.

According to one embodiment of the invention, a combination of these materials can yield a spectrum with a specific signature. Phosphor emissions from these materials, as illustrated in FIGS. 14A, 14B, and 14C, cover a broad range of the VIS and UV spectrum. Hence, in one embodiment, there is provided a system for light stimulation within a medium. The system includes an initiation source configured to radiate an initiation energy, a first plurality of energy-emitting particles in the medium which (upon radiation from the initiation source) radiate at a first lower energy than the initiation source to interact with photoactivatable agents in the medium, and a second plurality of energy-emitting particles in the medium which (upon radiation from the initiation source) radiate at a second lower energy than the initiation source to interact with photoactivatable agents in the medium. A combination of emission from the first and second plurality of energy-emitting particles produces a spectrum for illumination of the photoactivatable agents in the medium. The spectrum has a wavelength distribution simulating at least a part of an absorption spectrum of the photoactivatable agents or a spectrum of an ultraviolet discharge lamp.

In one aspect of the invention, the wavelength distribution can have a peak position in common with a peak in the absorption spectrum of the photoactivatable agents or can simulates an absorption edge of the absorption spectrum of the photoactivatable agents. In another aspect, the first and second plurality of energy-emitting particles can be a weighted composition of a plurality of different light-emitting particles, where light emitted from the weighted composition simulates part of the absorption spectrum of the photoactivatable agents.

In another aspect, the combination of the emission from the first and second plurality of energy-emitting particles can be configured about a target site to form a light source illuminating the target site to treat the target site with the photoactivatable agents. In another aspect, an energy distribution emitted from the first and second plurality of energy-emitting particles resembles the absorption spectrum of the photoactivatable agents or the spectrum of the ultraviolet discharge lamp. The energy distribution can overlap with the absorption spectrum of the photoactivatable agents or the spectrum of the ultraviolet discharge lamp.

Toxicity Testing:

Clonogenic Survival Assay (Low Density Protocol): In low density clonogenics, multiple cell densities are plated first and then treated. This clonogenic technique minimizes plating effects and pilot errors. In contrast, high density clonogenics have one stock plate of cells that is treated and then trypsinized and plated at different densities. This assay is more labor intensive and more prone to errors (e.g., pilot and plating) as well as contamination. However, this technique may more accurately depict the clinical situation as it allows cells to have more cell-to-cell contact.

The procedures followed for the clonogenic survival assays below are as follows:
1. Label plates (cells, treatments, date, initials).
   a. Plate cells in triplicate at 3 different densities (such as 100, 300, and 1,000 cells/plate).
      i. The # of cells plated depends on:
         1. The cell line (for example HeLa, HT29, B16/F10 and most MEF cell lines, recommend using 100, 300 and 1,000 cells per plate).
         2. Treatments—the higher drug concentrations, higher IR doses or longer hypoxia treatments are usually more toxic compared to less stringent conditions, so use more cells for the more toxic treatments.
2. Calculate the drug concentrations and the amount of media needed for each treatment.
   a. Media:
      i. In 6-well plates, use 3 mL media per well—so total amount of media needed is (3 mL/well)*(total # of plates)*(# of wells/plate)
      ii. In 6-well plates, use 3 mL media per plate—so total amount of media needed is (3 mL/well)*(total # of plates)*(# of wells/plate)
      iii. Also, take into account any media changes/washes—if using drug treatments, double the amount of media needed as you will need to add fresh mediafter the drugs are rinsed off the cells.
   b. Drugs:
      i. Make fresh drug dilutions for every experiment
      ii. Make drug dilutions beforehand—if adding drugs directly to the media, add greater 3 μL volume per well. Any volume less than 3 μL adds potential error to your experiment.
3. Plating:
   a. Trypsinize cells.
   b. Determine total # of cells for each cell density in a 6-well format:
      i. (# of plates)*(3 well/plate)*(100 cells/well)=Total # of cells needed to give 3 wells 100 cells/well in each plate.
      ii. (# of plates)*(3 well/plate)*(300 cells/well)=Total # of cells needed to give 3 wells 300 cells/well in all plates
      iii. Calculate media needed to plate each density:
         1. (# of plates)*(3 well/plate)*(3 mL/well)=Total # mL of media needed to plate each density.
   c. Pellet cells—centrifuge @ 1,000 rpm/2-3 min/4° C.
   d. Resuspend in mediand count.
   e. Make serial dilutions to obtain the number of cells needed to add to total volume of media (step 3iii).
      i. If 1,200,000 cells/ml are counted, plate #100 and #300 cells/well—dilute the total number of cells down to a more manageable volume.
      ii. Dilute (1:10) the main stock 1,200,000 cells/ml- to give 120,000 cells/ml—dilute (1:10) again to give 12,000 cells/ml—dilute (1:10) again gives 1,200 cells/ml. See FIG. 15A.
   f. Plate 3 ml of mediand cells in each well of all plates
   g. Put in the incubator and allow cells ~18-24 hr to attach.
4. Treat cells:
   a. Treat cells according to the experimental design
      i. Optional (depends on experiment): Remove media on all plates, rinse with 2 mL 1×PBS and then add fresh 3 mL of media.
   b. Incubate plates under normal conditions (37° C. and 5% $CO_2$) for 7-14 days, or until visually detecting colonies of greater than 50 cells in the cell alone control plates.
   c. Stain plates.
5. Staining (not necessarily under sterile conditions):
   a. Decant media off plates.
   b. Rinse plates with ~2 mL 1×PBS.
   c. Add Fixation Solution and leave on for 10 min/RT
      i. Typically, 2-3 mL is enough (i.e. enough to cover the bottom of the plate)
   d. Decant Fixation Solution
   e. Add Crystal Violet Stain (enough to cover bottom of plate) and leave on for 10 min/RT.
   f. Rinse plates with water.
      i. Fill sink with water and drop plates in as you remove the crystal violet.
      ii. Rinse off plates with water.
   g. Allow plates to dry on bench paper
   h. Count colonies using the ColCounter.
      i. Count colonies that have >50 cells in them—look at colonies under the microscope if you are unsure.

| Fixation Solution: | Crystal Violet |
|---|---|
| 10% Methanol<br>10% Acetic Acid | 500 mL of working stock:<br>0.4% Crystal Violet (200 mL of the 1% stock)<br>20% Ethanol (100 mL)<br>200 mL $H_2O$ |

6. Datanalysis:
   a. Record the number of colonies for each cell density and treatment group.
   b. Correct for cell density (i.e. normalize all plates to 100 cells)
      i. Compare between groups to see if the groups are all corrected to reflect the same number of cells plated.
         1. To compare your treatment #1 on 300 cells to control/vehicle on 100 cells—divide your number of colonies from your 300 cell group by 3 since there are 3× as many cells.
   c. Calculate the plating efficiency (survival of your control-plated cells)
      i. Average the # colonies in your control plates
   d. Correct for plating efficiency (this removes effects just from plating your cells)
      i. Divide the surviving fractions normalized for cell density (Step 6B) by the plating efficiency calculated in Step 6C.
   e. Calculate survival fraction, which is the average of the corrected numbers in Step 6D, standard deviation as well as standard error (standard deviation divided by the square root of (n)).
   f. Plot Surviving Fraction (semi-log plot; y-axis) vs. treatments (linear; x-axis).

Solubilization Protocol:
(Used if working with cell lines that do not form tight, distinct colonies—like some GBM lines. Reference: Bernardi et al (2001) Clinical Cancer Research 7, 4164-73)
1. Add 33% acetic acid to each of your 60 mm plates 24 hr post-staining.
   a. Do not use less than 400 μL.
2. Aliquot 100 μL from each plate (in triplicate) to a 96-well plate.
3. Read the absorbance at 540 nm and average the 3 values.

4. Normalize all values based on the volume solubilized and then follow regular datanalysis steps.

The phosphors were tested in two forms, coated and uncoated. All coated phosphors were designated by a "c" at the end for example BP7c (blue phosphor #7 coated). All uncoated phosphors were designated by a "u" at the end for example BP3u (blue phosphor #3 uncoated). Most of the coatings tested in our experiments consisted of silica. All uncoated phosphors were predominantly oxides. The assigned names to the various phosphors are provided in the following Table 9 in FIG. 15B.

Toxicity Testing of $YTaO_4$:Nb

Various phosphors including $YTaO_4$:Nb phosphors were tested for their inherent toxicity using a clonogenic survival assay (the details of which are provided below). Three different doses of $YTaO_4$:Nb were used in this case. In this particular case, the $YTaO_4$:Nb oxide phosphor was coated with a nano-meter size layer of silica.

Figure 15C:
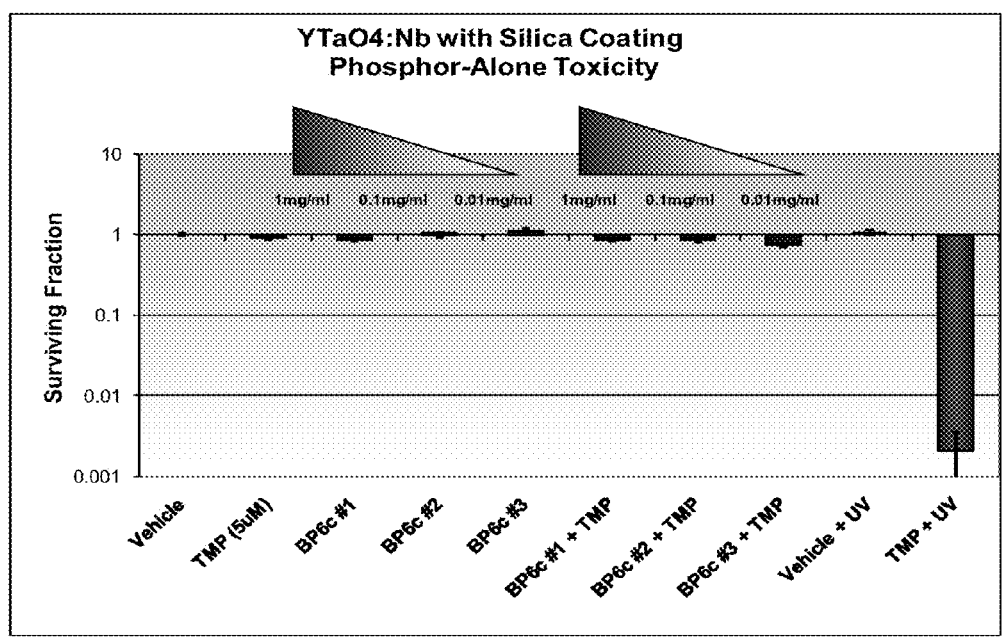
FIG. 15C is a schematic of the results from a clonogenic assay for a $YTaO_4$:Nb phosphor with and without a silica coating.

This clonogenic survival assay was plated using the B16 mouse melanoma cells with TMP (5 :m/ml) and/or silica coated YTaO4:Nb phosphor at three concentrations (1 mg/ml, 100 :g/ml, 10 :g/ml). The mixture sat on the cells for 3 hr, and then the media was removed. $YTaO_4$:Nb was found to be non-toxic up to a dose of 1 mg/ml alone or in combination with TMP. FIG. 15C is a depiction of the results of $YTaO_4$:Nb Phosphor-Alone Toxicity using clonogenic assay. No inherent toxicity was observed. The $YTaO_4$:Nb with silica coating was found to be non toxic even in high doses.

Figure 16:
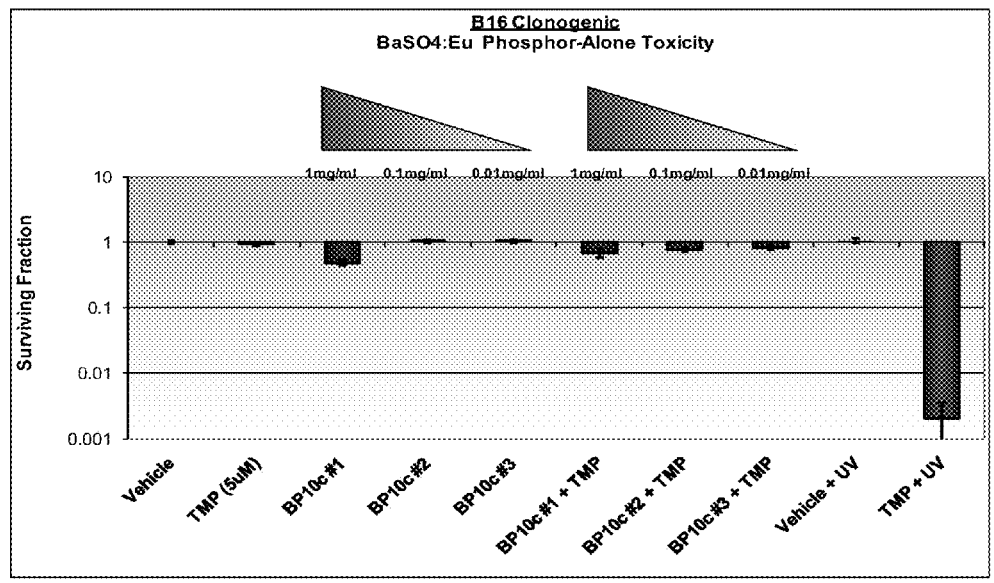
FIG. 16 is a schematic of the results from a clonogenic assay for a $BaSO_4$:Eu phosphor with and without a silica coating.

Toxicity Testing of $BaSO_4$:Eu:

Three doses of $BaSO_4$:Eu were used to look for any inherent toxicity. FIG. 16 is a depiction of the results of BaSO4:Eu phosphor-alone toxicity using the clonogenic assay. $BaSO_4$:Eu with silica coating was added in three different concentrations to B16 mouse melanoma cells with TMP. No inherent toxicity was observed. The clonogenic survial assay was plated using the B16 mouse melanoma cells with TMP (5 μm/ml) and/or $BaSO_4$:Eu phosphor (1 mg/ml, 100 μg/ml, 10 μg/ml) sat on the cells for 3 hr, and then the media was removed. $BaSO_4$:Eu phosphor coated with silica coating was found to be non-toxic at 100 :g/ml and 10 :g/ml. It had moderately toxic at 1 mg/ml.

Figure 17:
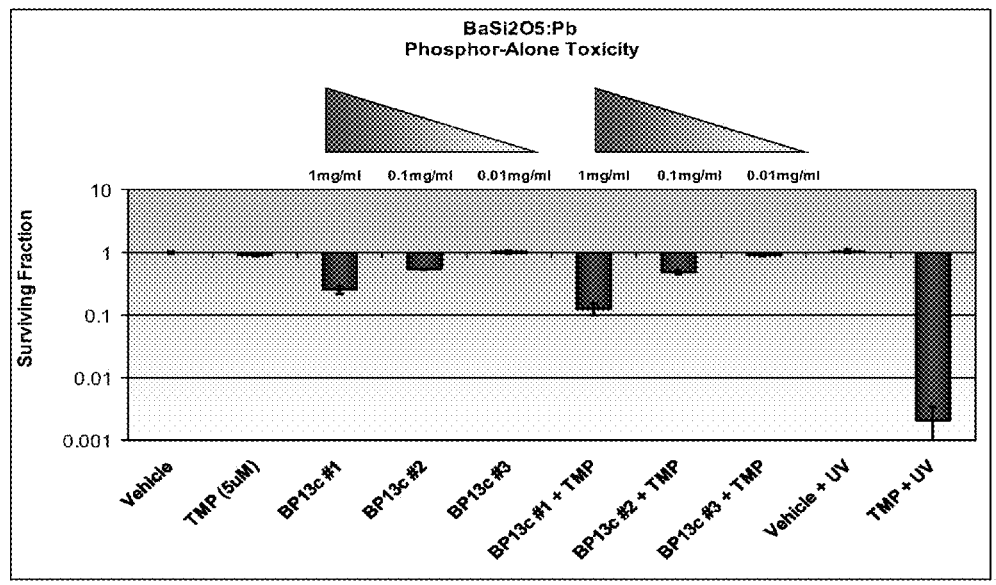
FIG. 17 is a schematic of the results from a clonogenic assay for a $BaSi_2O_5$:Pb phosphor with and without a silica coating.

Toxicity Testing of $BaSi_2O_5$:Pb:

Three doses of $BaSi_2O_5$:Pb were used to look for any inherent toxicity. FIG. 17 is a depiction of $BaSi_2O_5$:Pb phosphor-alone toxicity using the clonogenic assay. A $BaSi_2O_5$:Pb phosphor coated in silica containing trace amounts of Pb, is much more toxic at the highest concentration compared to either of the previous phosphors. This clonogenic survival assay was plated using the B16 mouse melanoma cells with TMP (5 m/ml) and/or $BaSi_2O_5$:Pb phosphor (1 mg/ml, 100 :g/ml, 10 :g/ml) sat on the cells for 3 hr, and then the media was removed. $BaSi_2O_5$:Pb was found to be non-toxic at 10 :g/ml, moderately toxic at 100 :g/ml, and markedly toxic at 1 mg/ml.

$YTaO_4$ Phosphor Coated with Silica Under X-Ray in the Presence of TMP:

Another clonogenic survival assay was plated using the B16 mouse melanoma cells. The testing was designed to determine if the $YTaO_4$ phosphor plus TMP lead to melanoma cells kill. Two levels of x-ray energy (filament to target voltage) were used. The TMP was added at a concentration of (5 μm/ml) and/or phosphor (1 mg/ml, 100 :g/ml, or 10 :g/ml). The mixture sat on the cells for 3 hr before the cells were exposed to radiation. The radiation was given to the indicated groups using the Orthovoltage machine where the 2 Gy total dose was delivered using 2 different energy levels (135 kVp, 160 kVp).

There is some degree of XRT+phosphor effect even at the lower doses of phosphor at 160 kVp. One effect of the X-ray radiation treatment with the $YTaO_4$ phosphor was observable though not as pronounced at 135 kVp. The cell kill results indicated a 30-40% 'inherent' toxicity with 1 mg/ml of phosphor (high concentration).

Figure 18:
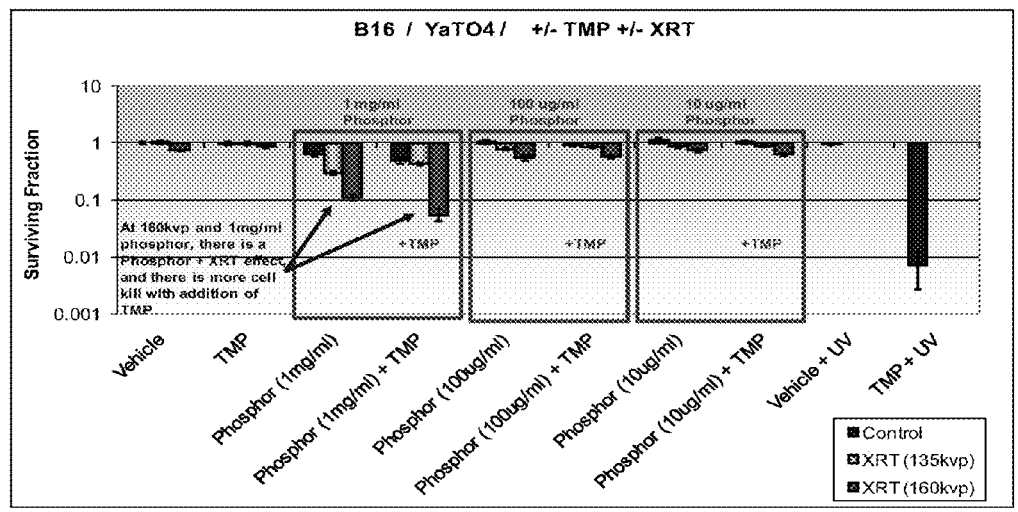
FIG. 18 is a schematic showing the effect of X-ray from a voltage of 160 kVp and 1 mg/ml concentration of the $YTaO_4$ phosphor showing a XRT and Phosphor effect, and further cell kill when adding trimethyl psoralen (TMP)

FIG. 18 is a depiction of the results using a voltage of 160 kVp and 1 mg/ml concentration of the $TaO_4$ phosphor, which shows a marked XRT and Phosphor effect, and further cell kill when adding TMP.

Based on this data with $YTaO_4$, two concentrations of the $YTaO_4$ phosphors were evaluated to resolve with greater details the combined effect of phosphor plus X-Ray radiation plus TM at 160 kVp+TMP. This clonogenic survival assay was plated using the B16 mouse melanoma cells with TMP (5 μm/ml) and/or $YTaO_4$ phosphor (1 mg/ml, 500 :g/ml) sat on the cells for 3 hr before the cells were exposed to radiation. The radiation was given to the indicated groups using the Orthovoltage machine with the 2 Gy total dose at 160 kVp.

Figure 19:
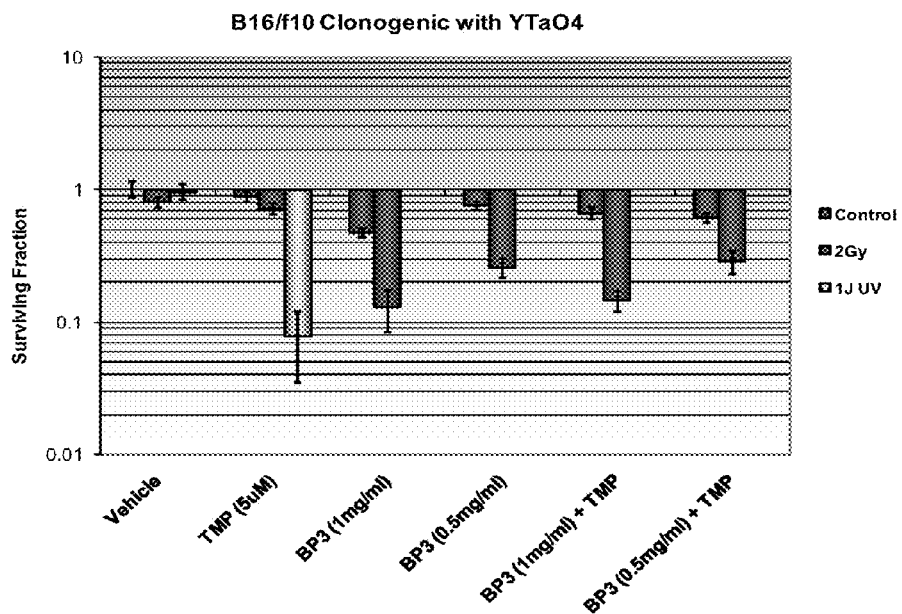
FIG. 19 is a schematic of the results from a clonogenic assay for a YTaO$_4$ phosphor with and without a silica coating for three different concentrations added to a B16 mouse melanoma cells with TMP.

A repeatable and reproducible signal was observed based on the effect of radiation and phosphor. However, no significant added benefit of adding TMP was observed. In fact the data showed that (in this case) the addition of TMP lessened the surviving cell fraction. Perhaps, the TMP may have selectively adsorbed on the particle surfaces or the UV intensity was attenuated more in the presence of TMP. In either case, the phosphor effect was observable under X-ray. FIG. 19 is a depiction of the $YTaO_4$ phosphor-alone toxicity—using clonogenic assay with three different concentrations added to B16 mouse melanoma cells with TMP.

Figure 20:
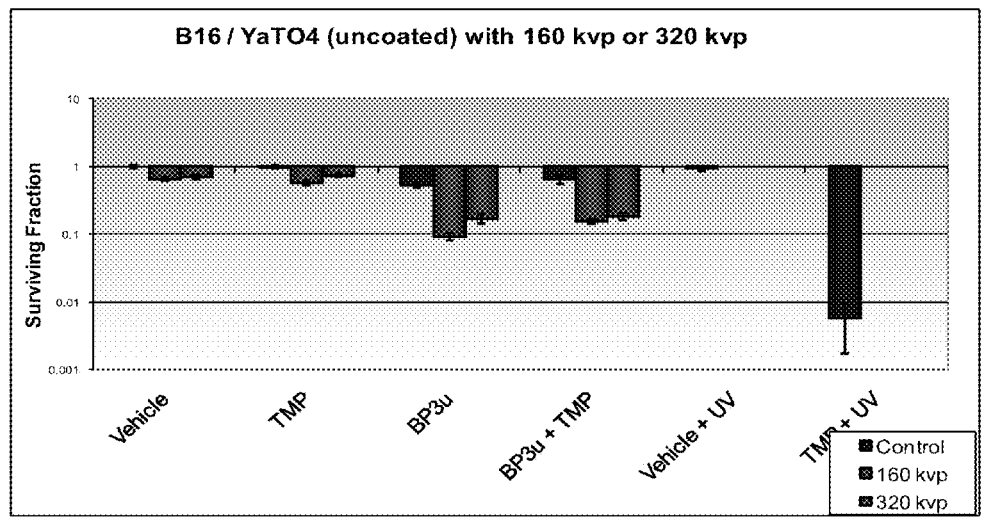
FIG. 20 is a schematic of the results from a clonogenic assay for a YTaO$_4$ phosphor (uncoated) at 0.75 mg/ml+/−2 gray XRT at 160 kVp or 320 kVp.

$YTaO_4$ Phosphor (with No Coating) Under X-Ray in the Presence of TMP:

Another clonogenic test was carried out using an identical $YTaO_4$ (BP3u) without the $SiO_2$. In essence, the innate oxide was tested to resolve the impact of the surface finish of the phosphor. FIG. 20 is a depiction of the results with $YTaO_4$ (uncoated) at 0.75 mg/ml+/−2 gray XRT at 160 kVp or 320 kVp. 30-40% cell kill from radiation alone was observed. There is moderate toxicity with 0.75 mg/ml of $YTaO_4$ uncoated by itself (36-48% kill). There is a markedly enhanced cell kill with $YTaO_4$ plus XRT. However, similarly to the previous result shown in FIG. 18, there is no added benefit from XRT+BP3u+TMP.

With $YTaO_4$ (uncoated) at a dose of 0.75 mg/ml, there is moderate toxicity from the phosphor alone. An enhanced cell kill with BP3u+radiation. However, there was observed no added benefit of $YTaO_4$+radiation+TMP at either 160 kVp or 320 kVp.

Figure 21:
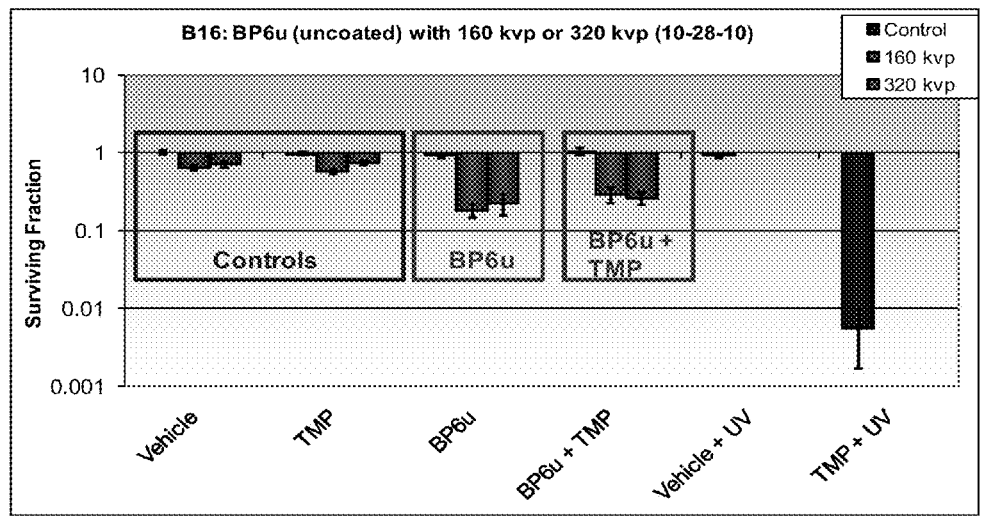
FIG. 21 is a schematic of the results from a clonogenic assay for a YTaO$_4$:Nb phosphor (uncoated) at 0.75 mg/ml, +/−2 gray XRT at 160 kVp and 320 kVp.

$YTaO_4$:Nb Phosphor (with No Coating) Under X-Ray in the Presence of TMP:

Another clonogenic test was carried out using the same phosphor base matrix with a doping that shifted the peak emission. This was achieved by adding niobium to the tantalate chemistry to form $YTaO_4$:Nb (BP6u). This evaluated phosphor was without the $SiO_2$ coating. In essence, the innate oxide was tested to resolve the impact of the surface finish of the phosphor. FIG. 21 is a depiction of the results with $YTaO_4$:Nb (uncoated) at 0.75 mg/ml, +/−2 gray XRT at 160 kVp and 320 kVp. 30-40% cell kill from radiation alone was observed. There is minimal toxicity with 0.75 mg/ml of BP6u by itself (0-7% kill). There is markedly enhanced cell kill with YTaO$_4$:Nb plus XRT. However, there is no added benefit from XRT plus YTaO$_4$:Nb plus TMP at these kVp levels.

LaOBr:Tm$^{3+}$ Phosphor (with SiO$_2$ Coating) Under X-Ray in the Presence of TMP:

Based on the previous data with YTaO4, three doses of LaOBr:Tm$^{3+}$ were evaluated to look for a phosphor plus radiation plus TMP effect. This clonogenic survival assay was plated using the B16 mouse melanoma cells with TMP (5 μm/ml) and/or LaOBr:Tm phosphor (1 mg/ml, 100 :g/ml, 10 :g/ml) sat on the cells for 3 hrs before the cells were exposed to radiation. The radiation was given to the indicated groups using the Orthovoltage machine (2 gy total dose at 160 kVp or 80 kVp).

Figure 22:
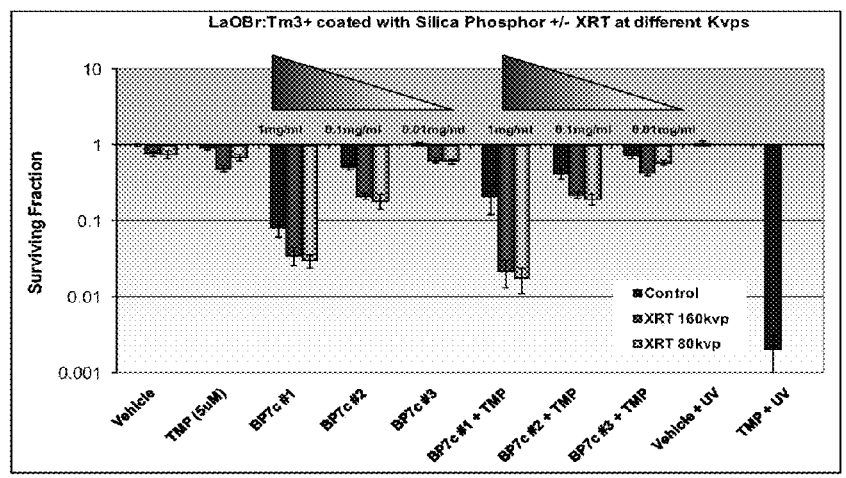
FIG. 22 is a schematic of the results from a clonogenic assay for a LaOBr:Tm phosphor (coated with SiO$_2$)

FIG. 22 is a depiction of the results with LaOBr:Tm (coated with SiO$_2$) phosphor-alone toxicity—using a clonogenic assay with three different concentrations added to B16 mouse melanoma cells with TMP. LaOBr:Tm is toxic by itself (see the blue bars in FIG. 22). There was no additional benefit of adding TMP at these kVp levels. LaOBr:Tm while the brightest phosphor was found to be toxic by itself. This is not a surprise in the view of the bromine constituent which is toxic. Also, no TMP activation was seen, as with the previous experiment, at either 80 or 160 kVp. However, with this phosphor having a strong UV and visible light intensity, a lower X-Ray dose experiment was carried out. These experiments were carried out at 40 kVp and 80 kVp.

Figure 23:
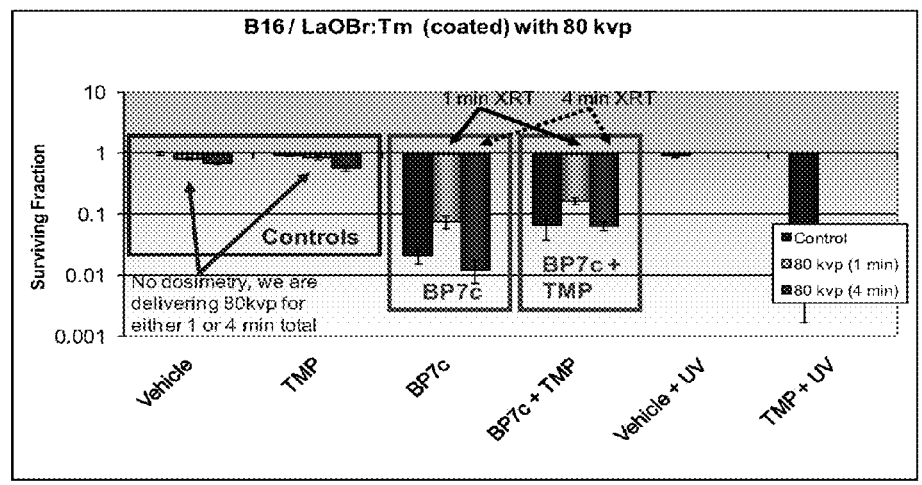
FIG. 23 is a schematic of the results from a clonogenic assay for a LaOBr:Tm phosphor (coated with SiO$_2$) with Phosphor-Alone Toxicity using at 0.75 mg/ml and phosphor plus TMP at 80 kVp XRT for 1 or 4 minutes total.

LaOBr:Tm$^{3+}$ Phosphor (with SiO$_2$ Coating) Under X-Ray Using 80 kVp in the Presence of TMP FIG. 23 is a depiction of the results with a LaOBr:Tm (coated with SiO$_2$) phosphor-(BP7c) toxicity using a concentration of 0.75 mg/ml phosphor plus TMP concentration at 80 kVp for 1 or 4 minutes total. There is marked toxicity with 0.75 mg/ml of LaOBr:Tm by itself resulting in a 93-98% kill. The radiation bars are difficult to interpret in light of the severe, inherent toxicity of these phosphors With BP7c (coated) at a dose of 0.75 mg/ml, there is marked toxicity from the phosphor alone. It was difficult to interpret the radiation data in light of the marked inherent toxicity of this phosphor at the concentration of 0.75 mg/ml. It is not possible to determine if there is a radiation plus phosphor effect, or an added benefit of TMP at 80 kVp for either 1 min or 4 min.

Figure 24:
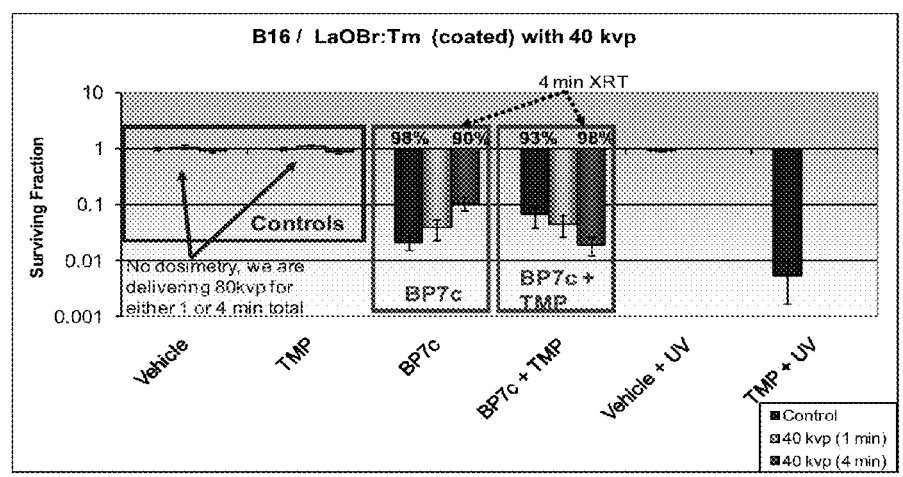
FIG. 24 is a schematic of the results from a clonogenic assay for a LaOBr:Tm phosphor (coated with SiO$_2$) with Phosphor-Alone Toxicity using at 0.75 mg/ml and phosphor plus TMP at 40 kVp XRT for 1 or 4 minutes total.

LaOBr:Tm$^{3+}$ Phosphor (with SiO$_2$ Coating) Under X-Ray Using 40 kVp in the Presence of TMP FIG. 24 is a depiction of the results with a LaOBr:Tm (coated with SiO$_2$) phosphor-alone toxicity using a concentration of 0.75 mg/ml plus TMP at 40 kVp XRT for 1 or 4 minutes total. With LaOBr:Tm (coated) at a dose of 0.75 mg/ml, there is marked toxicity from the phosphor alone. It was difficult to interpret the radiation data in light of the marked inherent toxicity of this phosphor at 0.75 mg/ml. It is not possible to tell if there is a radiation+phosphor effect, or an added benefit of TMP in this study at 40 kVp for either 1 min or 4 min.

There is marked toxicity with 0.75 mg/ml of LaOBr:Tm by itself 93-98% kill. The plus radiation LaOBr:Tm radiation bars are difficult to interpret in light of the inherent toxicity. Though the brown bars (40 kVp for 4 min) may appear to be different, there is only an 8% difference between those bars. The LaOBr:Tm plus TMP plus XRT bar is not different from the toxicity of LaOBr:Tm alone.

Figure 25:
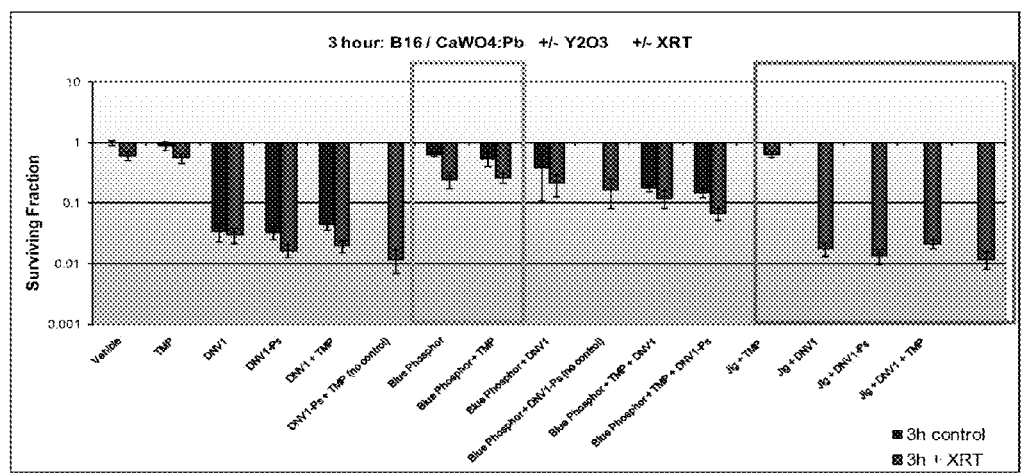
FIG. 25 is a schematic of a cell kill assay performed with a CaWO$_4$ phosphor combined with the Y$_2$O$_3$ particles.

CaWO$_4$ Phosphor (with No Coating) with Surface Modified Y$_2$O$_3$ Under X-Ray in the Presence of TMP:

In this experiment, B16 mouse melanoma cells were plated in a 6-well format for a clonogenic survival assay. Cells were treated with combinations of TMP, downconverting nanoparticles, phosphor fixture used for processing in the irradiator or phosphor powder mixed into the media. FIG. 25 is a depiction of the results of the cell kill assay performed with CaWO$_4$ combined with the Y$_2$O$_3$ particles in some cases. CaWO$_4$ plus TMP show an enhanced cell kill with radiation.

The cells were incubated with or without down-converting yttrium nanoparticles for 3 hours. These particles were either tethered to a tat-peptide or a tat-peptide conjugated with psoralen. X-ray exposure of the blue phosphor fixture results in UV emission which should activate TMP in the cell media. For the radiation set with CaWO$_4$ phosphor in the media, the cells were exposed to the phosphor and/or TMP and/or nanoparticles for 3 hours. The nanoparticle preparation was so toxic that an interpretation of enhanced cell kill with this nanoparticle combination was not possible.

Figure 26:
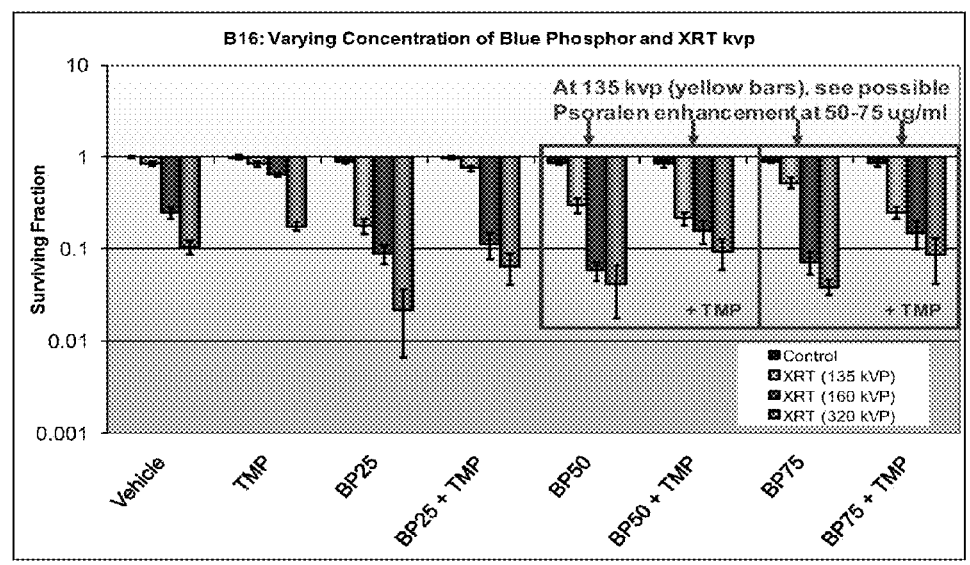
FIG. 26 is a schematic of the results from a clonogenic assay for B16 mouse melanoma cells treated with a CaWO$_4$ phosphor.

Another clonogenic survival assay was plated using the B16 mouse melanoma cells to test if the CaWO$_4$ phosphor at 3 intermediate concentrations can activate TMP to kill melanoma cells using 3 different energy levels of radiation. The cells were plated and allowed to attach to the plates overnight. The next day, CaWO$_4$ powder was suspended in water to give a 100 mg/ml stock and then added directly to the cells to give final concentrations of 0.25 mg/ml, 0.5 mg/ml and 0.75 mg/ml. TMP, previously dissolved in DMSO. was also added to the cells at the same time to give a final concentration of 5 :M. The drug and phosphor sat on the cells for 3 hr before the cells were exposed to radiation. The radiation was given to the indicated groups using the Orthovoltage machine where the 2 Gy total dose was delivered using three different energy levels (135 kVp, 160 kVp and 320 kVp). FIG. 26 is a depiction of the results with B16 clonogenic assay for the CaWO$_4$ phosphor by varying the X-ray voltage (135 kVp, 160 kVp and 320 kVp) and phosphor doses 0.25 mg/ml, 0.5 mg/ml and 0.75 mg/ml. A signal of psoralen enhancement at 50 and 75 mg/ml was observed.

Figure 27:
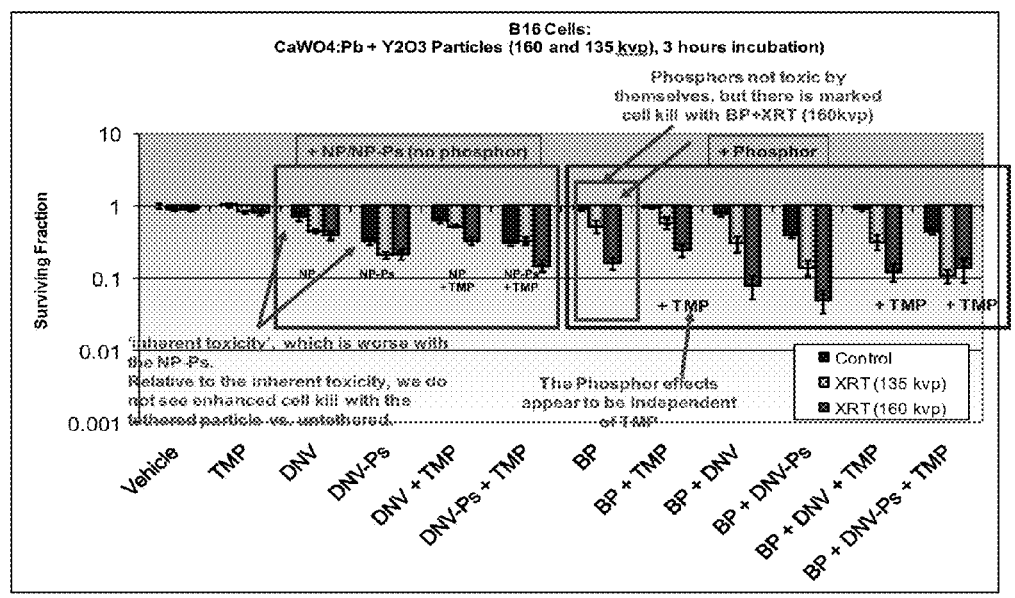
FIG. 27 is a schematic of the results from a clonogenic assay for B16 mouse melanoma cells treated with a CaWO$_4$ phosphor by varying the X-ray voltage.

Another clonogenic survival assay was plated using the B16 mouse melanoma cells testing if the CaWO$_4$ phosphor plus TMP to kill melanoma cells using two different energy levels of radiation, to determine whether adding nanoparticles provides a benefit. The drug, particles, and phosphor sat on the cells for 3 hr before the cells were exposed to radiation. The radiation was given to the indicated groups using the Orthovoltage machine where the 2 Gy total dose was delivered using two different energy levels (135 kVp and 160 kVp). FIG. 27 is a depiction of the results of a B16 clonogenic assay using the CaWO$_4$ phosphor and varying the X-ray voltage (135 kVp and 160 kVp).

There was significant toxicity from the nanoparticles, especially with the psoralen-tethered particles. The phosphor was not toxic by itself, but provided enhanced cell kill in the present of radiation. This phosphor+radiation effect was independent of TMP. The CaWO$_4$ phosphors have a very pronounced cell kill when treated with X-ray radiation. This effect does not seem to rely on TMP.

Energy Modulation Agent Modifications:

In one embodiment of the invention, a phosphor production process for producing novel phosphor configurations is provided. The following depicts schematically this process and the resultant phosphor configurations.

Figure 28:
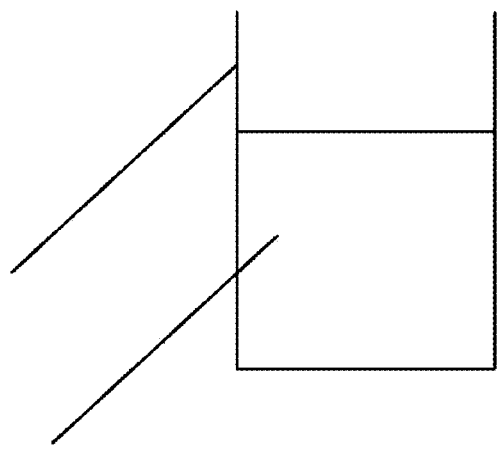
FIG. 28 is a schematic of a container including a solution containing nano-particles.
Figure 29:
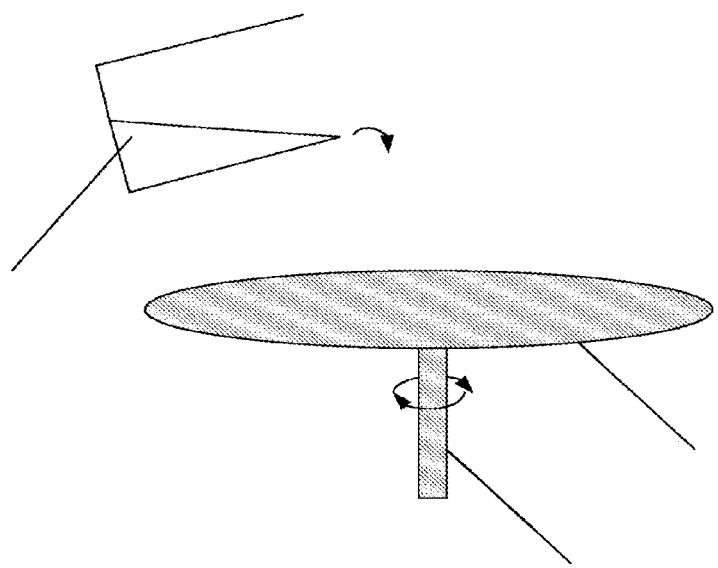
FIG. 29 is a schematic of a solution containing nano particles applied to a quartz wafer through the process of spin coating.
Figure 30:
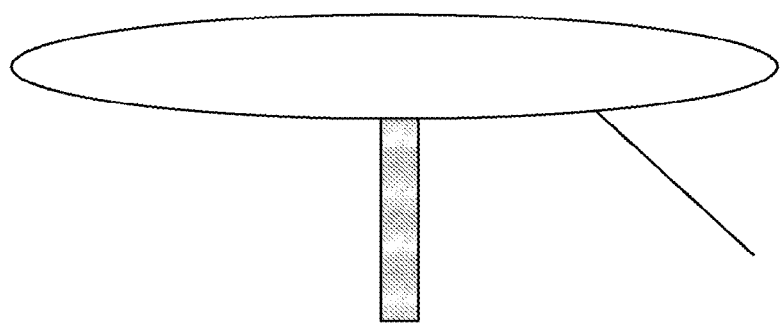
FIG. 30 is a schematic of a wafer dried to produce a thin layer of nanoparticles dispersed across the surface of the wafer.

FIG. 28 is a schematic of a container including a solution containing nano-particles. FIG. 29 is a schematic of a solution containing nano particles applied to a quartz wafer through the process of spin coating. FIG. 30 is a schematic of the wafer dried with a thin layer of the nanoparticles dispersed across the surface of the wafer.

Figure 31A:
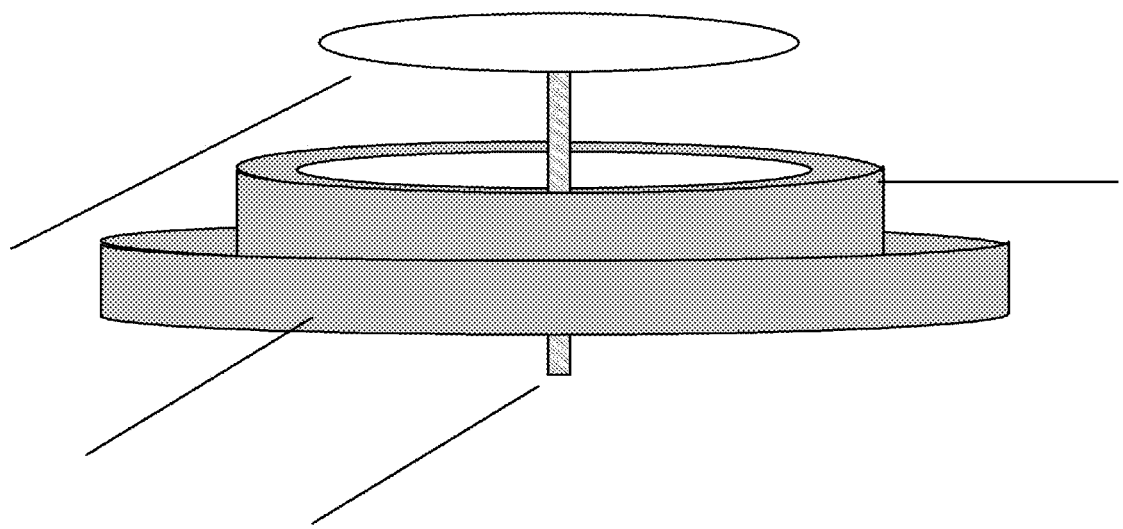
FIG. 31A is a schematic of a wafer a taken to a physical vapor deposition system
Figure 31B:
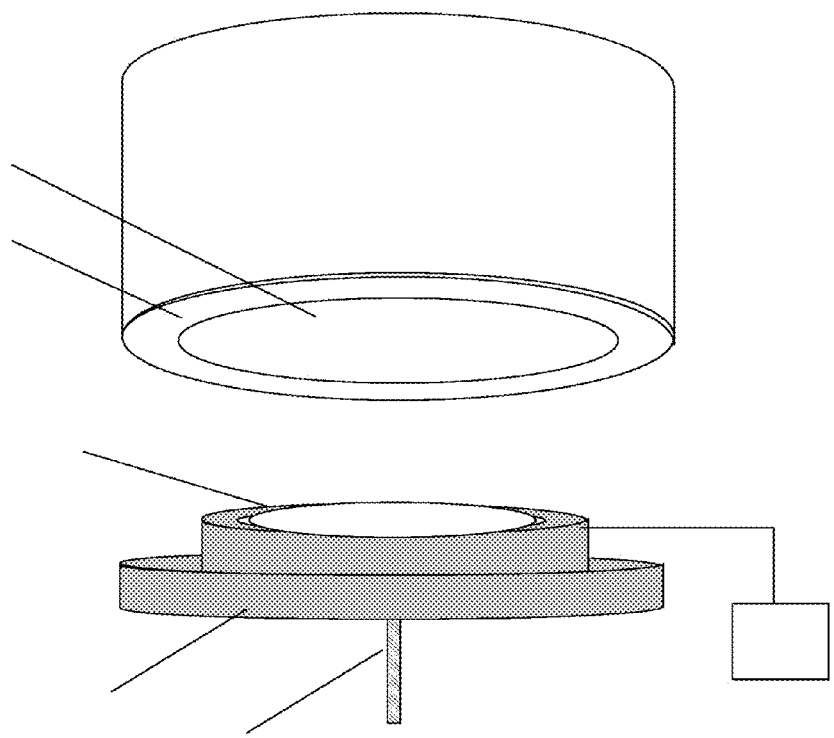
FIG. 31B is a schematic of a wafer placed onto a biasable and heatable stage and inserted into physical vapor deposition system for applying a coating on a top half of the nano particles.
Figure 32:
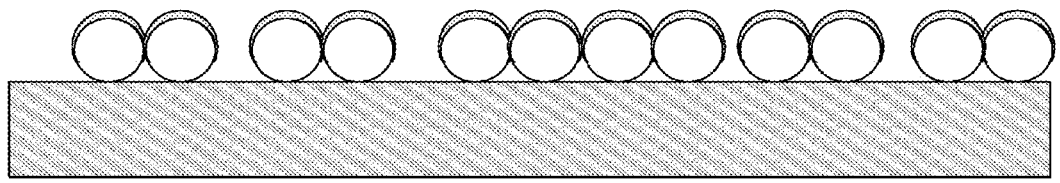
FIG. 32 is a schematic of a cross section of the quartz wafer coated with nanoparticles.

FIG. 31A is a schematic of the wafer with nano particle dispersion taken to a physical vapor deposition system. FIG. 31B is a schematic of the wafer lower onto a biased and heated stage, and inserted into physical vapor deposition system for applying a coating on half of the nanoparticles. FIG. 32 is a schematic of the cross section of the quartz wafer coated with nanoparticles. The coating applied in the PVD system is applied to a top half the particles.

Figure 33:
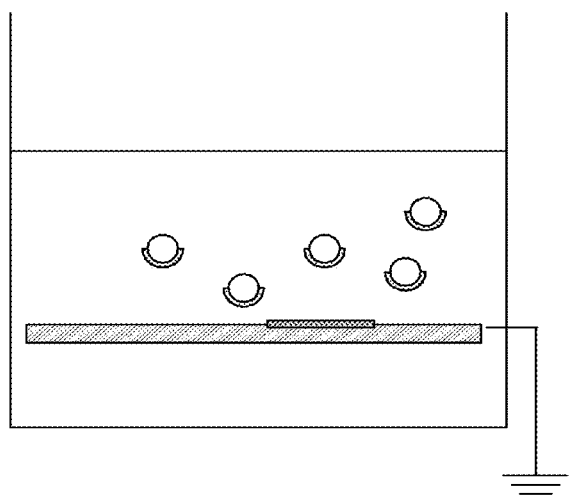
FIG. 33 is a schematic of the half coated phosphor particles placed back in solution inside a container that has a biased stage.

FIG. 33 is a schematic of the half coated phosphor particles placed back in a solution inside a container that has a biased stage. The biased stage contains metallic nano rods.

Figure 34:
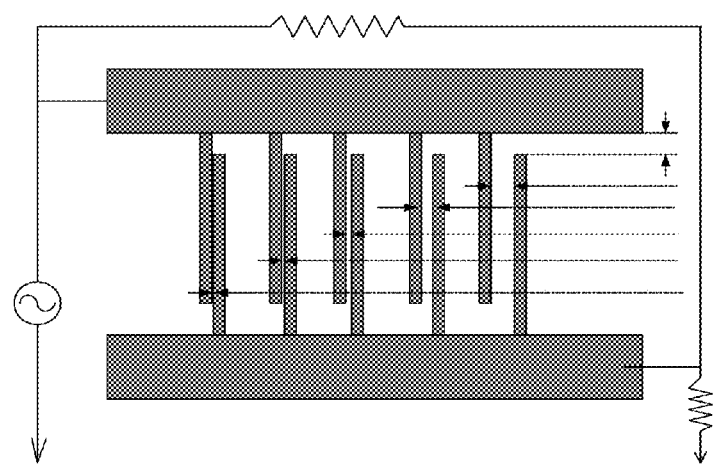
FIG. 34 is a schematic of the half coated phosphor particles placed back in solution inside a container that has a RF biased stage.

FIG. 34 is a schematic of an alternative process where the solution containing phosphors with a metallic coating is placed in a micro-electrode structure having a RF feed energizing the electrodes. The electrodes are disposed to form various gaps ranging from the micron to submicron levels.

Figure 35:
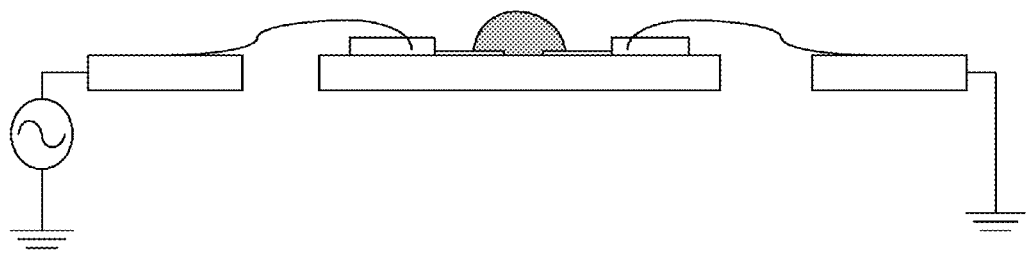
FIG. 35 is a schematic of the half coated phosphor particles placed back in solution inside a container that has a RF biased micro-electrode structure.

FIG. 35 is a cross-sectional schematic of this alternative process where the solution containing phosphors with a metallic coating is placed in a micro-electrode structure having a RF feed energizing the electrodes. The electrodes are disposed to form various gaps ranging from the micron to submicron levels.

Figure 36:
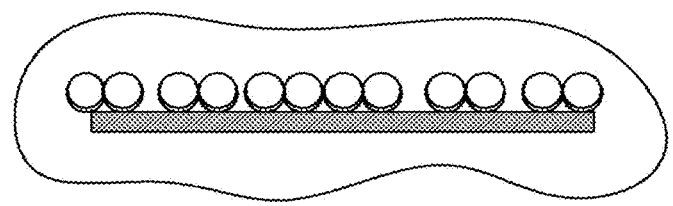
FIG. 36 is a schematic of the half coated phosphor particles disposed around a metallic nano rod and heated to sufficient temperatures to alloy the metallic coating with the metallic nano rod.

FIG. 36 is a schematic depicting the half coated phosphor particles disposed around a metallic nano rod and heated to sufficient temperatures to alloy the metallic coating with the metallic nano rod. Subsequently, a silica gel coating process is applied to coat the composite structure using silica.

Figure 37:
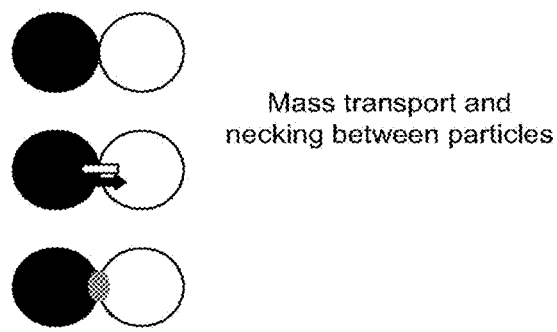
FIG. 37 is a schematic of mass transport being used to form a neck between particles.

FIG. 37 is a schematic depicting a mass transport process, necking the region between particles.

Figure 38:
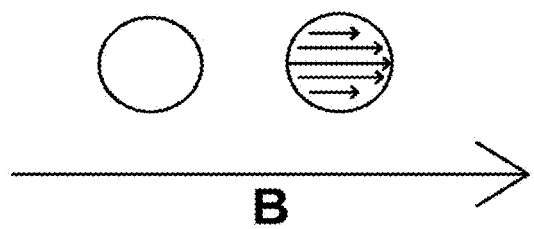
FIG. 38 is a schematic showing alignment of a magnetic particle under a magnetic field and followed by joining the phosphor and the magnetic particles with a lateral field configuration.

FIG. 38 is a schematic depicting alignment of a magnetic particle under a magnetic field and followed by joining the phosphor and the magnetic particles (lateral field configuration).

Figure 39:
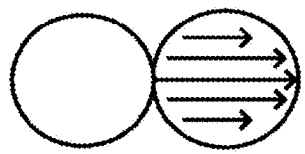
FIG. 39 is a schematic showing the joining of a magnetic particle and phosphor through a necking process.
Figure 40:
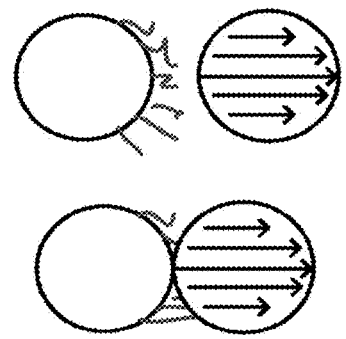
FIG. 40 is a schematic showing the joining of a magnetic particle and phosphor through an adhesion process by surface modification of at least one of the particles.

FIG. 39 is a schematic depicting the joining of a magnetic particle and phosphor through a necking process. FIG. 40 is a schematic depicting the joining of a magnetic particle and phosphor through an adhesion process by surface modification of at least one of the particles.

Figure 41:
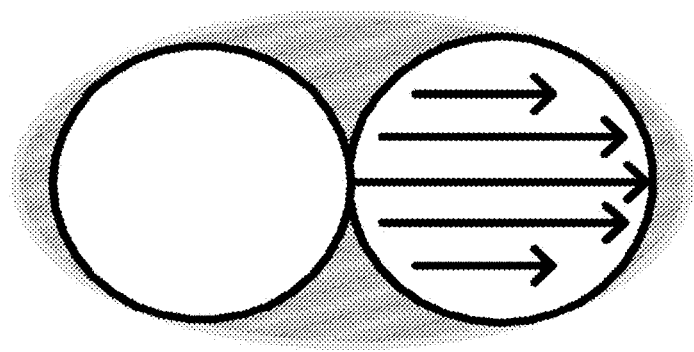
FIG. 41 is a schematic showing a lipid envelop around the adhered phosphor and nano magnetic particle.
Figure 42:
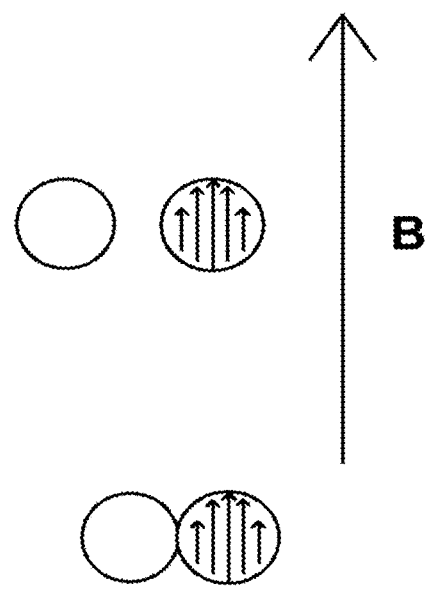
FIG. 42 is a schematic showing the alignment of a magnetic particle under a magnetic field and followed by joining the phosphor and the magnetic particles (orthogonal field configuration)

FIG. 41 is a schematic depicting a lipid envelop around the adhered phosphor and nano magnetic particle. FIG. 42 is a schematic depicting alignment of a magnetic particle under a magnetic field and followed by joining the phosphor and the magnetic particles (orthogonal field configuration).

Figure 43:
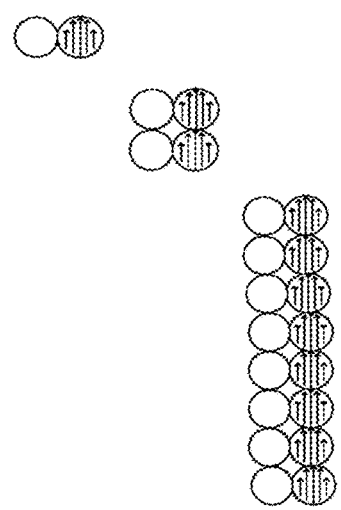
FIG. 43 is a schematic showing that, after joining the particles in an orthogonal field configuration, the particles would have a tendency to self assemble in a recto-linear fashion.
Figure 44:
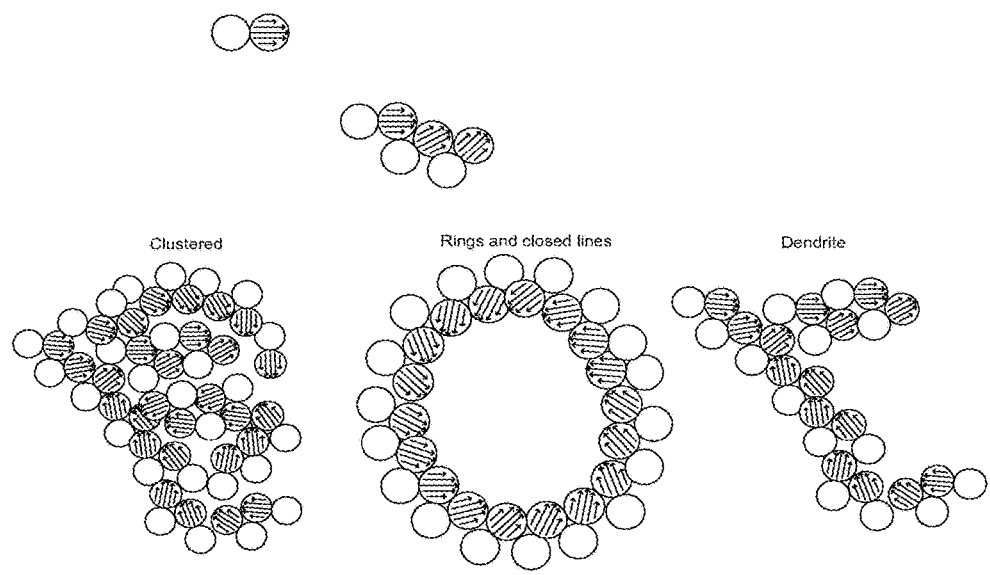
FIG. 44 is a schematic showing that, after joining the particles in a lateral field configuration, the particles would have a tendency to self assemble in dendrite configurations, clusters and rings.

FIG. 43 is a schematic depicting a situation where, after joining the particles in an orthogonal field configuration, the particles have a tendency to self assemble in a recto-linear fashion. FIG. 44 is a schematic depicting a situation where, after joining the particles in a lateral field configuration, the particles have a tendency to self assemble in dendrite configurations, clusters and rings.

The phosphors of this invention are not limited to those described above. Other phosphors are suitable and are applicable for various applications where mixtures of down converters are needed. For example, other down converters known in the art and suitable for this invention include $TiO_2$, ZnO, $Fe_2O_3$, CdTe, CdSe, ZnS, CaS, BaS, SrS and $Y_2O_3$. Other suitable down conversion materials known in the art include zinc sulfide, $ZnS:Mn^{2+}$, ferric oxide, titanium oxide, zinc oxide, zinc oxide containing small amounts of $Al_2O_3$ and AgI nanoclusters encapsulated in zeolite. Other suitable down conversion materials include lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, Cesium Iodine, Bismuth Germanate, Cadmium Tungstate, and CsBr doped with divalent Eu.

In various embodiments of the invention, the following luminescent polymers known in the art are also suitable as conversion materials: poly(phenylene ethynylene), poly (phenylene vinylene), poly(p-phenylene), poly(thiophene), poly(pyridyl vinylene), poly(pyrrole), poly(acetylene), poly (vinyl carbazole), poly(fluorenes), and the like, as well as copolymers and/or derivatives thereof.

In various embodiments of the invention, the following particles can be used similar to that detailed in U.S. Pat. No. 7,090,355, the entire contents of which are incorporated herein by reference. For down-conversion, the following materials can be used: inorganic or ceramic phosphors or nano-particles, including but not limited to metal oxides, metal halides, metal chalcoginides (e.g. metal sulfides), or their hybrids, such as metal oxo-halides, metal oxo-chalcoginides; laser dyes and small organic molecules, and fluorescent organic polymers; semiconductor nano-particles, such as II-VI or III-V compound semiconductors, e.g. fluorescent quantum dots; organometallic molecules including at least a metal center such as rare earth elements (e.g. Eu, Tb, Ce, Er, Tm, Pr, Ho) and transitional metal elements such as Cr, Mn, Zn, Ir, Ru, V, and main group elements such as B, Al, Ga, etc. The Garnet series of phosphors can be used: $(Y_m A_{1-m})_3 (Al_n B_{1-n})_5 O_{12}$, doped with Ce; where $0 \le m$, $n \le 1$, where A includes other rare earth elements, B includes B, Ga. In addition, phosphors containing metal silicates, metal borates, metal phosphates, and metal aluminates hosts can be used. In addition, phosphors containing common rare earth elements (e.g. Eu, Tb, Ce, Dy, Er, Pr, Tm) and transitional or main group elements (e.g. Mn, Cr, Ti, Ag, Cu, Zn, Bi, Pb, Sn, Tl) as the fluorescent activators, can be used. Materials such as Ca, Zn, Cd in tungstates, metal vanadates, ZnO, etc. can be used.

Semiconductor nanoparticles can be used. The term "semiconductor nanoparticles," in the art refers to an inorganic crystallite between 1 nm and 1000 nm in diameter, preferably between 2 nm to 50 nm. A semiconductor nanoparticle is capable of emitting electromagnetic radiation upon excitation (i.e., the semiconductor nano-particle is luminescent). The nanoparticle can be either a homogeneous nano-crystal, or comprises of multiple shells. For example, the nanoparticle can include a "core" of one or more first semiconductor materials, and may be surrounded by a "shell" of a second semiconductor material. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, and an alloy or a mixture thereof.

Other down converters include for example ZnS, PbS, $SbS_3$, $MoS_2$, PbTe, PbSe, BeO, MgO. $Li_2CO_3$, $Ca(OH)_2$, $MoO_3$, $SiO_2$, $Al_2O_3$, $TeO_2$, $SnO_2$, KBr, KCl, and NaCl. These materials can include dopants to tailor the emission properties. Examples of doped (or alloyed) glass systems suitable for the include $Y_2O_3$:Gd, $Y_2O_3$:Dy, $Y_2O_3$:Tb, $Y_2O_3$: Ho, $Y_2O_3$:Er, $Y_2O_3$:Tm, $Gd_2O_3$:Eu, $Y_2O_2S$:Pr, $Y_2O_2S$:Sm, $Y_2O_2S$:Eu, $Y_2O_2S$:Tb, $Y_2O_2S$:Ho, $Y_2O_2S$:Er, $Y_2O_2S$:Dy, $Y_2O_2S$:Tm, ZnS:Ag:Cl (blue), ZnS:Cu:Al (green), $Y_2O_2S$: Eu (red), $Y_2O_3$:Eu (red), $YVO_4$:Eu (red), and $Zn_2SiO_4$:Mn (green).

Alternatively, quantum dots can be used to tailor the down conversion process. As described in U.S. Pat. No. 6,744,960 (the entire contents of which are incorporated by reference), different size quantum dots produce different color emissions. As applicable to this invention, quantum dots can comprise various materials including semiconductors such as zinc selenide (ZnSe), cadmium selenide (CdSe), cadmium sulfide (CdS), indium arsenide (InAs), and indium phosphide (InP). Another material that may suitably be employed is titanium dioxide ($TiO_2$). The size of the particle, i.e., the quantum dot, may range from about 2 to 10 nm. Since the size of these particles is so small, quantum physics governs many of the electrical and optical properties of the quantum dot. One such result of the application of quantum mechanics to the quantum dot is that quantum dots absorb a broad spectrum of optical wavelengths and re-emit radiation having a wavelength that is longer than the wavelength of the absorbed light. The wavelength of the emitted light is governed by the size of the quantum dot. For example, CdSe quantum dots 5.0 nm in diameter emit radiation having a narrow spectral distribution centered about 625 nm while quantum dots 18 including CdSe 2.2 nm in size emit light having a center wavelength of about 500 nm. Semiconductor quantum dots comprising CdSe, InP, and InAs, can emit radiation having center wavelengths in the range between 400 nm to about 1.5 µm. Titanium dioxide $TiO_2$ also emits in this range. The line width of the emission, i.e., full-width half-maximum (FWHM), for these semiconductor materials may range from about 20 to 30 nm. To produce this narrowband emission, quantum dots simply need to absorb light having wavelengths shorter than the wavelength of the light emitted by the dots. For example, for 5.0 nm diameter CdSe quantum dots, light having wavelengths shorter than about 625 nm is absorbed to produce emission at about 625 nm while for 2.2 nm quantum dots comprising CdSe light having wavelengths smaller than about 500 nm is absorbed and re-emitted at about 500 nm.

The converters in one embodiment can include a down converter including at least one of $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS: $Tb^{3+}$, $Er^{3+}$; $ZnS:Tb^{3+}$; $Y_2O_3:Tb^{3+}$; $Y_2O_3:Tb^{3+}$, Er3+; ZnS: $Mn^{2+}$; $ZnS:Mn,Er^{3+}$, alkali lead silicate including compositions of $SiO_2$, $B_2O_3$, $Na_2O$, $K_2O$, PbO, MgO, or Ag, and combinations or alloys or layers thereof.

In other embodiments, a metal coating or a metallic structure can exist inside the dielectric and the relative position of the metal structure to the dielectric structure can enhance plasmonic resonance. These structures with the metallic structure inside can be referred to as a metallic core up converter or a metallic core down converter. The metallic core technique for energy conversion is useful since it takes advantage of metal nano-particles that have improved surface morphology compared to shell coatings on core dielectrics. The metal or metallic alloy in the inner core metallic energy converter can be selected to tune its plasmonic activity.

Such nanoparticle structures can exhibit in certain embodiments surface plasmonic resonance in the metallic shell to enhance upconversion of light from a first wavelength $\lambda_1$ to a second wavelength $\lambda_2$.

As described above, shell is in particular designed with a layer thickness to enhance the photon upconversion process through plasmonic enhancement. The thickness of the shell is "tuned" in its thickness to the absorption process by having a dimension in which plasmons (i.e., electrons oscillations) in shell have a resonance in frequency which provides spectral overlap with the absorption band of the incident light targeted. Thus, the thickness of the shell is "tuned" in a thickness to where a plasmon resonance resonates at a frequency of interest for stimulating a photoactivatable agent.

Such a plasmon resonating shell can be made of numerous transition metals, including though not limited to gold, silver, platinum, palladium, nickel, ruthenium, rhenium, copper, and cobalt. This capability of matching or tuning of the frequencies provides an enhancement of the absorption which would not be present with a dielectric core alone.

In one embodiment of this invention, the thickness of the metal shell is set depending on the emission frequency to enhance the total efficiency of the emission process. Accordingly, the thickness of the shell can be considered as a tool that in one instance enhances the absorption of $\lambda_1$, and in another instance can be considered as a tool that enhances the emission of $\kappa_2$, or in other situations can be considered an enhancement feature that in combination enhances the overall conversion process.

Additionally, plasmon-phonon coupling may be used to reduce a resonance frequency through the tuning of the bands to a degree off resonance. This may be useful in optimizing resonance energy transfer processes for the purpose of coupling the core-shell nanoparticles to sensitive chromophores or drug targets. Accordingly, when a recipient is outside of the shell, the recipient will receive enhanced light $\lambda_2$ by the above-described plasmonic effect than would occur if the shell were absent from the structure.

Accordingly, a plasmonics effect (from plasmonic inducing agents) is advantageous. A plasmonics effect can occur throughout the electromagnetic region provided the suitable nanostructures, nanoscale dimensions, metal types are used. Plasmonic effects are possible over a wide range of the electromagnetic spectrum, ranging from gamma rays and X rays throughout ultraviolet, visible, infrared, microwave and radio frequency energy.

Photodynamic Therapy (PDT) with the Energy Modulation Agents of the Invention:

In one embodiment of this invention, the above-described energy modulation agents (phosphors, scintillators, fluorescent materials, and combinations and agglomerations thereof) with or without plasmonic inducing agents can be used in photodynamic therapy for the light source.

PDT is a relatively new light-based treatment, which has recently been approved by the United States Food & Drug Administration (FDA) for the treatment of both early and late-stage lung cancer. Other countries have approved PDT for treatment of various cancers as well. Unlike chemotherapy, radiation, and surgery, PDT is useful in treating all cell types, whether small cell or non-small cell carcinoma. PDT involves treatment of diseases such as cancer using light action on a special photoactive class of drugs, by photodynamic action in vivo to destroy or modify tissue [Dougherty T. J. and Levy J. G., "Photodynamic Therapy and Clinical Applications", in *Biomedical Photonics Handbook*, Vo-Dinh T., Ed., CRC Press, Boca Raton Fla. (2003)]. PDT, which was originally developed for treatment of various cancers, has now been used to include treatment of pre-cancerous conditions, e.g. actinic keratoses, high-grade dysplasia in Barrett's esophagus, and non-cancerous conditions, e.g. various eye diseases, e.g. age related macular degeneration (AMD). Photodynamic therapy (PDT) is approved for commercialization worldwide both for various cancers (lung, esophagus) and for AMD.

The PDT process requires three elements: (1) a PA drug (i.e., photosensitizer), (2) light that can excite the photosensitizer and (3) endogenous oxygen. The putative cytotoxic agent is singlet oxygen, an electronically excited state of ground state triplet oxygen formed according to the Type II photochemical process, as follows.

PA+hv→¹PA*(S) Excitation

¹PA*(S)→³PA*(T) Intersystem crossing for singlet to triplet state

³PA*(T)+O₂→¹O*₂+PA Energy transfer from the drug to singlet oxygen where PA=photo-active drug at the ground state; $^1PA^*(S)$=excited singlet state; $^3PA^*(T)$=excited triplet state; $^1O^*_2$=singlet excited state of oxygen Because the triplet state has a relatively long lifetime (μsec to seconds) only photosensitizers that undergo efficient intersystem crossing to the excited triplet state will have sufficient time for collision with oxygen in order to produce singlet oxygen. The energy difference between ground state and singlet oxygen is 94.2 kJ/mol and corresponds to a transition in the near-infrared at ~1270 nm. Most PA photosensitizers in clinical use have triplet quantum yields in the range of 40-60% with the singlet oxygen yield being slightly lower. Competing processes include loss of energy by deactivation to ground state by fluorescence or internal conversion (loss of energy to the environment or surrounding medium).

However, while a high yield of singlet oxygen is desirable it is by no means sufficient for a photosensitizer to be clinically useful. Pharmacokinetics, pharmacodynamics, stability in vivo and acceptable toxicity play critical roles as well [Henderson B W, Gollnick S O, "*Mechanistic Principles of Photodynamic Therapy*", in *Biomedical Photonics Handbook*, Vo-Dinh T., Ed., CRC Press, Boca Raton Fla. (2003)]. For example, it is desirable to have relatively selective uptake in the tumor or other tissue being treated relative to the normal tissue that necessarily will be exposed to the exciting light as well. Pharmacodynamic issues such as the subcellular localization of the photosensitizer may be important as certain organelles appear to be more sensitive to PDT damage than others (e.g. the mitochondria). Toxicity can become an issue if high doses of photosensitizer are necessary in order to obtain a complete response to treatment. An important mechanism associated with PDT drug activity involves apoptosis in cells. Upon absorption of light, the photosensitiser (PS) initiates chemical reactions that lead to the direct or indirect production of cytotoxic species such as radicals and singlet oxygen. The reaction of the cytotoxic species with subcellular organelles and macromolecules (proteins, DNA, etc) lead to apoptosis and/or necrosis of the cells hosting the PDT drug. The preferential accumulation of PDT drug molecules in cancer cells combined with the localized delivery of light to the tumor, results in the selective destruction of the cancerous lesion. Compared to other traditional anticancer therapies, PDT does not involve generalized destruction of healthy cells. In addition to direct cell killing, PDT can also act on the vasculature, reducing blood flow to the tumor causing its necrosis. In particular cases it can be used as a less invasive alternative to surgery.

There are several chemical species used for PDT including porphyrin-based sensitizers. A purified hematoporphyrin derivative, Photofrin®, has received approval of the US Food and Drug Administration. Porphyrins are generally used for tumors on or just under the skin or on the lining of internal organs or cavities because theses drug molecules absorbs light shorter than 640 nm in wavelength. For tumors occurring deep in tissue, second generation sensitizers, which have absorbance in the NIR region, such as porphyrin-based systems [R. K. Pandey, "*Synthetic Strategies in designing Porphyrin-Based* Photosensitizers', in *Biomedical Photonics Handbook*, Vo-Dinh T., Ed., CRC Press, Boca Raton Fla. (2003)], chlorines, phthalocyanine, and naphthalocyanine have been investigated.

PDT retains several photosensitizers in tumors for a longer time than in normal tissues, thus offering potential improvement in treatment selectivity. See Comer C., "Determination of [3H]- and [14C] hematoporphyrin derivative distribution in malignant and normal tissue," Cancer Res 1979, 3 9: 146-15 1; Young S W, et al., "Lutetium texaphyrin (PCI-0123) a near-infrared, water-soluble photosensitizer," Photochem Photobiol 1996, 63:892-897; and Berenbaum M C, et al., "Meso-Tetra(hydroxyphenyl)porphyrins, a new class of potent tumor photosensitisers with favourable selectivity," Br J Cancer 1986, 54:717-725. Photodynamic therapy uses light of a specific wavelength to activate the photosensitizing agent. Various light sources have been developed for PDT, which include dye lasers and diode lasers. Light generated by lasers can be coupled to optical fibers that allow the light to be transmitted to the desired site. See Pass 1-11, "Photodynamic therapy in oncology: mechanisms and clinical use," J Natl Cancer Inst 1993, 85:443-456. According to researchers, the cytotoxic effect of PDT is the result of photooxidation reactions, as disclosed in Foote C S, "Mechanisms of photooxygenation," Proa Clin Biol Res 1984, 170:3-18. Light causes excitation of the photosensitizer, in the presence of oxygen, to produce various toxic species, such as singlet oxygen and hydroxyl radicals. It is not clear that direct damage to DNA is a major effect; therefore, this may indicate that photoactivation of DNA crosslinking is not stimulated efficiently.

Photoactivation Treatments with the Energy Modulation Agents of the Invention:

For the treatment of cell proliferation disorders, an initiation energy source (e.g., light from the phosphors or scintillators of the invention) can provide an initiation energy that activates an activatable pharmaceutical agent to treat target cells within a subject. In one embodiment, the initiation energy source is applied indirectly to the activatable pharmaceutical agent, preferably in proximity to the target cells. Within the context of the present invention, the phrase "applied indirectly" (or variants of this phrase, such as "applying indirectly", "indirectly applies", "indirectly applied", "indirectly applying", etc.), when referring to the application of the initiation energy, means the penetration by the initiation energy into the subject beneath the surface of the subject and to the activatable pharmaceutical agent within a subject.

Although not intending to be bound by any particular theory or be otherwise limited in any way, the following theoretical discussion of scientific principles and definitions are provided to help the reader gain an understanding and appreciation of the present invention. As used herein, the term "subject" is not intended to be limited to humans, but may also include animals, plants, or any suitable biological organism.

As used herein, the phrase "cell proliferation disorder" refers to any condition where the growth rate of a population of cells is less than or greater than a desired rate under a given physiological state and conditions. Although, preferably, the proliferation rate that would be of interest for treatment purposes is faster than a desired rate, slower than desired rate conditions may also be treated by methods of the present invention. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Particularly preferred cell proliferation disorders for treatment using the present methods are cancer, *staphylococcus aureus* (particularly antibiotic resistant strains such as methicillin resistant *staphylococcus aureus* or MRSA), and autoimmune disorders.

As used herein, an "activatable pharmaceutical agent" (alternatively called a "photoactive agent" or PA) is an agent that normally exists in an inactive state in the absence of an activation signal. When the agent is activated by a matching activation signal under activating conditions, it is capable of affecting the desired pharmacological effect on a target cell (i.e. preferably a predetermined cellular change).

Signals that may be used to activate a corresponding agent may include, but are not limited to, photons of specific wavelengths (e.g. x-rays, or visible light), together with or without electromagnetic energy (e.g. radio or microwave), thermal energy, acoustic energy, or any combination thereof.

Activation of the agent may be as simple as delivering the signal to the agent or may further premise on a set of activation conditions. For example, in the former case, an activatable pharmaceutical agent, such as a photosensitizer, may be activated by UV-A radiation (e.g., UV-A light from the phosphors or scintillators of the invention). Once activated, the agent in its active-state may then directly proceed to effect a cellular change.

Where activation may further premise upon other conditions, mere delivery of the activation signal may not be sufficient to bring about the desired cellular change. For example, a photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors. Selection of an activatable pharmaceutical agent greatly depends on a number of factors such as the desired cellular change, the desired form of activation, as well as the physical and biochemical constraints that may apply.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, production of reactive oxygen species or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

The treatment can be by those methods described in U.S. application Ser. No. 11/935,655, filed Nov. 6, 2007 (incorporated by reference), or by a modified version of a conventional treatment such as PDT, but using a plasmonics-active agent to enhance the treatment by modifying or enhancing the applied energy or, in the case of using an energy modulation agent, modifying either the applied energy, the emitted energy from the energy modulation agent, or both.

In one embodiment, the activatable pharmaceutical agent is capable of chemically binding to the DNA or mitochondriat a therapeutically effective amount. In this embodiment, the activatable pharmaceutical agent, preferably a photoactivatable agent, is exposed in situ to an activating energy emitted from an energy modulation agent such as the phosphors or scintillators of the invention, which, in turn receives energy from an initiation energy source.

The activatable agent may be derived from a natural or synthetic origin. Any such molecular entity that may be activated by a suitable activation signal source to effect a predetermined cellular change may be advantageously employed in the present invention. Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethyli soalloxazine (lumiflavin), 7, 8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

Table 10 below lists some photoactivatable molecules capable of being photoactivated to induce an auto vaccine effect.

TABLE 10

| Compound | $\lambda_{ex}$ (nm) | $E_{SSET}$ | $k_s$ of donor ($s^{-1}$) | $k_{SSET}$ ($s^{-1}$) | $k_{SSET}$ ($s^{-1}$) (Average) | $R_0$ (Å) | R (Å) | $R_{model}$ (Å) (Average) | $E_{TTET}$ | $k_{TTET}$ ($s^{-1}$) |
|---|---|---|---|---|---|---|---|---|---|---|
| 1B | 224 | 96.3 | $9.5 \times 10^3$ | $2.44 \times 10^8$ | $1.87 \times 10^3$ | 14.7 | 9 | 9.5 | | |
|  | 266 | 95 |  | $1.8 \times 10^8$ |  |  |  |  | 2.5 | $5 \times 10^2$ |
|  | 280 | 94 |  | $1.36 \times 10^8$ |  |  |  |  |  |  |
| 1A | 224 | 80 | $9.5 \times 10^6$ | $3.6 \times 10^7$ | $3.67 \times 10^7$ | 14.7 | 11.8 | 14.1 | | |
|  | 266 | 79 |  | $3.6 \times 10^7$ |  |  |  |  | 2 | $3.6 \times 10^2$ |
|  | 280 | 79 |  | $3.6 \times 10^7$ |  |  |  |  |  |  |
| 2B | 224 | 77 | $9.5 \times 10^5$ | $3.1 \times 10^7$ | $3.9 \times 10^7$ | 14.7 | 11.9 | 6.5 | | |
|  | 266 | 81 |  | $3.9 \times 10^7$ |  |  |  |  | 32 | $9.4 \times 10^3$ |
|  | 280 | 83 |  | $4.7 \times 10^7$ |  |  |  |  |  |  |
| 2A | 224 | 69 | $9.5 \times 10^5$ | $2.1 \times 10^7$ | $3 \times 10^7$ | 14.7 | 12.2 | 8.1 | 74.3 | $5.7 \times 10^4$ |
|  | 266 | 80 |  | $3.7 \times 10^7$ |  |  |  |  |  |  |
|  | 280 | 77 |  | $3.2 \times 10^7$ |  |  |  |  |  |  |

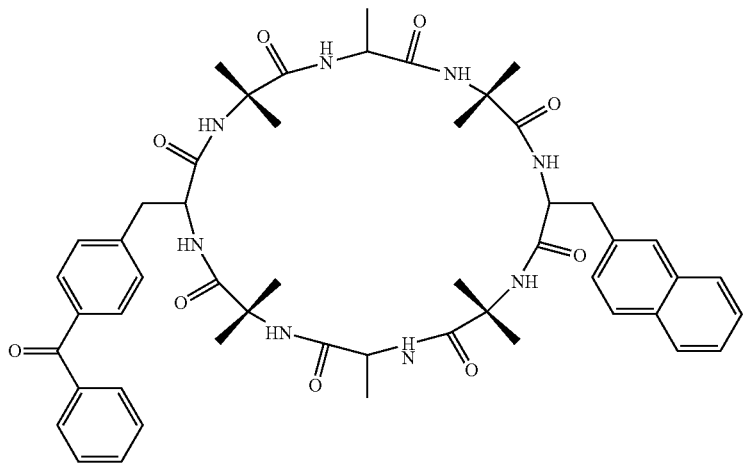

1A

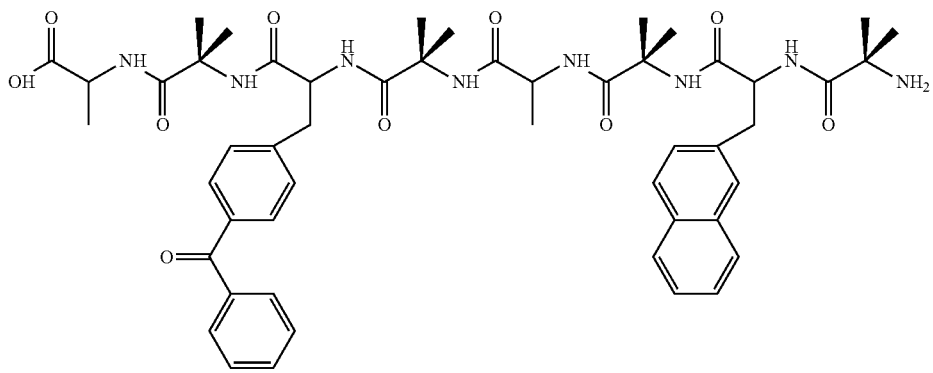

1B

-continued

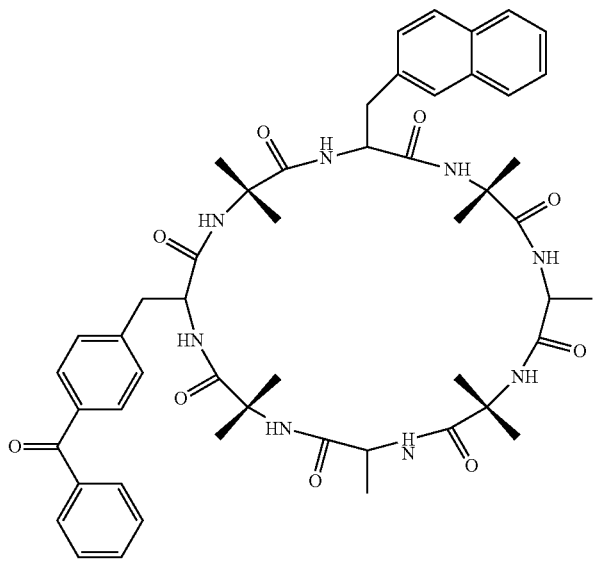

2A

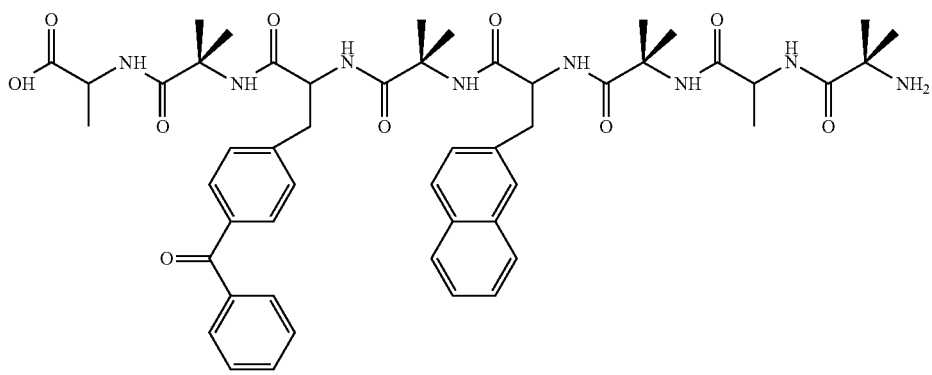

2B

| Endogenous Fluorophores | Excitation Max. (nm) | Emission Max. (nm) |
|---|---|---|
| Amino acids: | | |
| Tryptophan | 280 | 350 |
| Tyrosine | 275 | 300 |
| Phenylalanine | 260 | 280 |
| Structural Proteins: | | |
| Collagen | 325, 360 | 400, 405 |
| Elastin | 290, 325 | 340, 400 |
| Enzymes and Coenzymes: | | |
| flavin adenine dinucleotide | 450 | 535 |
| reduced nicotinamide dinucelotide | 290, 351 | 440, 460 |
| reduced nicotinamide dinucelotide phosphate | 336 | 464 |
| Vitamins: | | |
| Vitamins A | 327 | 510 |
| Vitamins K | 335 | 480 |
| Vitamins D | 390 | 480 |
| Vitamins $B_6$ compounds: | | |
| Pyridoxine | 332, 340 | 400 |
| Pyridoxamine | 335 | 400 |
| Pyridoxal | 330 | 385 |
| Pyridoxic acid | 315 | 425 |
| Pyridoxal phosphate | 5'-330 | 400 |
| Vitamin $B_{12}$ | 275 | 305 |

-continued

| Endogenous Fluorophores | Excitation Max. (nm) | Emission Max. (nm) |
|---|---|---|
| Lipids: | | |
| Phospholipids | 436 | 540, 560 |
| Lipofuscin | 340-395 | 540, 430-460 |
| Ceroid | 340-395 | 430-460, 540 |
| Porphyrins | 400-450 | 630, 690 |

Energy from light emitted from the phosphors, scintillators, fluorescent materials, and combinations and agglomerations thereof, with or without plasmonic inducing agents, of the invention may be transferred from one molecule to another (intermolecular transfer) or from one part of a molecule to another part of the same molecule (intramolecular transfer). For example, the electromagnetic energy may be converted into thermal energy. Energy transfer processes are also referred to as molecular excitation.

Additionally, energy modulation agents may be included in the medium to be treated. The energy modulation agents may upon receiving of light from the phosphors or scintilators of the invention re-emit a light specific to a desired photo-driven reaction. Energy modulation agents can have a very short energy retention time (on the order of fs-ns, e.g. fluorescent molecules) whereas others may have a very long half-life (on the order of seconds to hours, e.g. luminescent inorganic molecules or phosphorescent molecules). Various exemplary uses of these are described below in preferred embodiments.

The modulation agents may further be coupled to a carrier for cellular targeting purposes. For example, a biocompatible molecule, such as a fluorescing metal nanoparticle or fluorescing dye molecule that emits in the UV-A band, may be selected as the energy modulation agent.

The energy modulation agent of the invention such as the phosphors, scintillators, fluorescent materials, and combinations and agglomerations thereof, with or without plasmonic inducing agents may be preferably directed to the desired site (e.g. a tumor) by systemic administration to a subject. For example, a UV-A emitting energy modulation agent may be concentrated in the tumor site by physical insertion or by conjugating the UV-A emitting energy modulation agent with a tumor specific carrier, such as an antibody, nucleic acid, peptide, a lipid, chitin or chitin-derivative, a chelate, a surface cell receptor, molecular imprints, aptamers, or other functionalized carrier that is capable of concentrating the UV-A emitting source in a specific target tumor.

Additionally, the energy modulation agent can be used alone or as a series of two or more energy modulation agents wherein the energy modulation agents provide an energy cascade from the light of the phosphors or scintillators. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the activatable pharmaceutical agent.

Although the activatable pharmaceutical agent and the energy modulation agent can be distinct and separate, it will be understood that the two agents need not be independent and separate entities. In fact, the two agents may be associated with each other via number of different configurations. Where the two agents are independent and separately movable from each other, they generally interact with each other via diffusion and chance encounters within a common surrounding medium. Where the activatable pharmaceutical agent and the energy modulation agent are not separate, they may be combined into one single entity.

In general, photoactivatable agents may be stimulated by light of from the phosphors or scintillators of the invention, leading to subsequent irradiation, resonance energy transfer, exciton migration, electron injection, or chemical reaction, to an activated energy state that is capable of effecting the predetermined cellular change desired. In a one embodiment, the photoactivatable agent, upon activation, binds to DNA or RNA or other structures in a cell. The activated energy state of the agent is capable of causing damage to cells, inducing apoptosis. The mechanism of apoptosis is associated with an enhanced immune response that reduces the growth rate of cell proliferation disorders and may shrink solid tumors, depending on the state of the patient's immune system, concentration of the agent in the tumor, sensitivity of the agent to stimulation, and length of stimulation.

A preferred method of treating a cell proliferation disorder of the invention administers a photoactivatable agent to a patient, stimulates the photoactivatable agent by light from the phosphors or scintillators of the invention to induce cell damage, and generates an auto vaccine effect. In one further preferred embodiment, the photoactivatable agent is stimulated via resonance energy transfer.

One advantage is that multiple wavelengths of emitted radiation from the light from the phosphors or scintillators of the invention may be used to selectively stimulate one or more photoactivatable agents or energy modulation agents capable of stimulating the one or more photoactivatable agents. The energy modulation agent is preferably stimulated at a wavelength and energy that causes little or no damage to healthy cells, with the energy from one or more energy modulation agents being transferred, such as by Foerster Resonance Energy Transfer, to the photoactivatable agents that damage the cell and cause the onset of the desired cellular change, such as apoptosis of the cells.

Another advantage is that side effects can be greatly reduced by limiting the production of free radicals, singlet oxygen, hydroxides and other highly reactive groups that are known to damage healthy cells. Furthermore, additional additives, such as antioxidants, may be used to further reduce undesired effects of irradiation.

Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule. Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a photoactivatable molecule.

In another embodiment, the invention includes the administration of the activatable pharmaceutical agent, along with administration of a source of chemical energy such as chemiluminescence, phosphorescence or bioluminescence. The source of chemical energy can be a chemical reaction between two or more compounds, or can be induced by activating a chemiluminescent, phosphorescent or bioluminescent compound with an appropriate activation energy, either outside the subject or inside the subject, with the chemiluminescence, phosphorescence or bioluminescence being allowed to activate the activatable pharmaceutical agent in vivo after administration. The administration of the activatable pharmaceutical agent and the source of chemical energy can be performed sequentially in any order or can be performed simultaneously. In the case of certain sources of such chemical energy, the administration of the chemical energy source can be performed after activation outside the subject, with the lifetime of the emission of the energy being up to several hours for certain types of phosphorescent materials for example. There are no known previous efforts to use resonance energy transfer of any kind to activate an intercalator to bind DNA.

When drug molecules absorb excitation light, electrons undergo transitions from the ground state to an excited electronic state. The electronic excitation energy subsequently relaxes via radiative emission (luminescence) and radiationless decay channels. When a molecule absorbs excitation energy, it is elevated from $S_o$ to some vibrational level of one of the excited singlet states, $S_n$, in the manifold $S_1, \ldots, S_n$. In condensed media (tissue), the molecules in the $S_n$ state deactivate rapidly, within $10^{-13}$ to $10^{-11}$ s via vibrational relaxation (VR) processes, ensuring that they are in the lowest vibrational levels of $S_n$ possible. Since the VR process is faster than electronic transitions, any excess vibrational energy is rapidly lost as the molecules are deactivated to lower vibronic levels of the corresponding excited electronic state. This excess VR energy is released as thermal energy to the surrounding medium. From the $S_n$ state, the molecule deactivates rapidly to the isoenergetic vibrational level of a lower electronic state such as $S_{n-1}$ vian internal conversion (IC) process. IC processes are transitions between states of the same multiplicity. The molecule subsequently deactivates to the lowest vibronic levels of $S_{n-1}$ via VR process. By a succession of IC processes immediately followed by VR processes, the molecule deactivates rapidly to the ground state $S_1$. This process results in excess VR and IC energy released as thermal energy to the surrounding medium leading to the overheating of the local environment surrounding the light absorbing drug molecules. The heat produced results in local cell or tissue destruction. The light absorbing species include natural chromophores in tissue or exogenous dye compounds such as indocyanine green, naphthalocyanines, and porphyrins coordinated with transition metals and metallic nanoparticles and nanoshells of metals. Natural chromophores, however, suffer from very low absorption. The choice of the exogenous photothermal agents is made on the basis of their strong absorption cross sections and highly efficient light-to-heat conversion. This feature greatly minimizes the amount of energy needed to induce local damage of the diseased cells, making therapy method less invasive.

Various Light-Activated Pharmaceuticals Activatable with the Energy Modulation Agents of the Invention:

Another object of the invention is to treat a condition, disorder or disease in a subject using an activatable pharmaceutical agent activated using the above-described energy modulation agents (phosphors, scintillators, fluorescent materials, and combinations and agglomerations thereof) with or without plasmonic inducing agents.

It has been reported that ferritin could be internalized by some tumor tissues, and the internalization was associated with the membrane-specific receptors [S. Fargion, P. Arosio, A. L. Fracanzoni, V. Cislaghi, S. Levi, A. Cozzi, A Piperno and A. G. Firelli, *Blood,* 1988, 71, 753-757; P. C. Adams, L. W. Powell and J. W. Halliday, *Hepalology,* 1988, 8, 719-721]. Previous studies have shown that ferritin-binding sites and the endocytosis of ferritin have been identified in neoplastic cells [M. S. Bretscher and J. N. Thomson, *EMBO J.,* 1983, 2, 599-603]. Ferritin receptors have the potential for use in the delivery of anticancer drugs into the brain [S. W. Hulet, S. Powers and J. R. Connor, *J. Neurol. Sci.,* 1999, 165, 48-55]. In one embodiment, the invention uses ferritin or apoferritin to both encapsulate PAnd energy modulation agent-PA systems and also target tumor cells selectively for enhanced drug delivery and subsequent phototherapy. In this case, no additional bioreactors are needed.

The photoactive drug molecules can be given to a patient by oral ingestion, skin application, or by intravenous injection. The photoactive drug molecules drugs travel through the blood stream inside the body towards the targeted tumor (either via passive or active targeting strategies). The invention treatment may also be used for inducing an auto vaccine effect for malignant cells, including those in solid tumors. To the extent that any rapidly dividing cells or stem cells may be damaged by a systemic treatment, then it may be preferable to direct the stimulating energy directly toward the tumor, preventing damage to most normal, healthy cells or stem cells by avoiding photoactivation or resonant energy transfer of the photoactivatable agent.

Alternatively, a treatment may be applied that slows or pauses mitosis. Such a treatment is capable of slowing the division of rapidly dividing healthy cells or stem cells during the treatment, without pausing mitosis of cancerous cells. Alternatively, a blocking agent is administered preferentially to malignant cells prior to administering the treatment that slows mitosis.

In one embodiment, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death, even if exposed to photoactivated agents, provided that such photoactivated agents degenerate from the excited state to a lower energy state prior to binding, mitosis or other mechanisms for creating damage to the cells of a substantial fraction of the healthy stem cells. Thus, an auto-immune response may not be induced.

Alternatively, a blocking agent may be used that prevents or reduces damage to stem cells or healthy cells, selectively, which would otherwise be impaired. The blocking agent is selected or is administered such that the blocking agent does not impart a similar benefit to malignant cells, for example.

In one embodiment, stem cells are targeted, specifically, for destruction with the intention of replacing the stem cells with a donor cell line or previously stored, healthy cells of the patient. In this case, no blocking agent is used. Instead, a carrier or photosensitizer is used that specifically targets the stem cells.

Work in the area of photodynamic therapy has shown that the amount of singlet oxygen required to cause cell lysis, and thus cell death, is $0.32 \times 10^{-3}$ mol/liter or more, or $10^9$ singlet oxygen molecules/cell or more. However, in one embodiment of the invention, it is most preferable to avoid production of an amount of singlet oxygen that would cause cell lysis, due to its indiscriminate nature of attack, lysing both target cells and healthy cells. Accordingly, it is most preferred in the invention that the level of singlet oxygen production caused by the initiation energy used or activatable pharmaceutical agent upon activation be less than level needed to cause cell lysis.

In a further embodiment, methods in accordance with the invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

The activatable pharmaceutical agent and derivatives thereof as well as the energy modulation agent and plasmonics compounds and structures, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such mediand agents for pharmaceutically active substances is well known in the art. Except insofar as any conventional media or agent is incompatible with the active compound, use thereof in the compositions is contemplated. Supplementary active compounds can also be incorporated into the compositions.

Modifications can be made to the compound of the present invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteriand fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, the entire contents of which are incorporated herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, kit or dispenser together with instructions for administration.

Methods of administering agents are not limited to the conventional means such as injection or oral infusion, but include more advanced and complex forms of energy transfer. For example, genetically engineered cells that carry and express energy modulation agents may be used. Cells from the host may be transfected with genetically engineered vectors that express bioluminescent agents. Transfection may be accomplished via in situ gene therapy techniques such as injection of viral vectors or gene guns, or may be performed ex vivo by removing a sample of the host's cells and then returning to the host upon successful transfection. Such transfected cells may be inserted or otherwise targeted at the site where diseased cells are located.

It will also be understood that the order of administering the different agents is not particularly limited. It will be appreciated that different combinations of ordering may be advantageously employed depending on factors such as the absorption rate of the agents, the localization and molecular trafficking properties of the agents, and other pharmacokinetics or pharmacodynamics considerations.

An advantage of the methods of this approach is that by specifically targeting cells affected by a cell proliferation disorder, such as rapidly dividing cells, and triggering a cellular change, such as apoptosis, in these cells in situ, the immune system of the host may be stimulated to have an immune response against the diseased cells. Once the host's own immune system is stimulated to have such a response, other diseased cells that are not treated by the activatable pharmaceutical agent may be recognized and be destroyed by the host's own immune system. Such autovaccine effects may be obtained, for example, in treatments using psoralen and UV-A.

The methods described here can be used alone or in combination with other therapies for treatment of cell proliferation disorders. Additionally, the methods described can be used, if desired, in conjunction with recent advances in chronomedicine, such as that detailed in Giacchetti et al, *Journal of Clinical Oncology*, Vol 24, No 22 (August 1), 2006: pp. 3562-3569, the entire contents of which are incorporated herein by reference.

In chronomedicine, it has been found that cells suffering from certain types of disorders, such as cancer, respond better at certain times of the day than at others. Thus, chronomedicine could be used in conjunction with the present methods in order to augment the effect of the treatments of the invention.

Photo-Treatment with the Energy Modulation Agents of the Invention

Another object of the invention is to treat a condition, disorder or disease in a subject using an activatable pharmaceutical agent activated using the above-described energy modulation agents (phosphors, scintillators, fluorescent materials, and combinations and agglomerations thereof) with or without plasmonic inducing agents. Exemplary conditions, disorders or diseases may include, but are not limited to, cancer, autoimmune diseases, cardiac ablasion (e.g., cardiac arrhythmiand atrial fibrillation), photoangioplastic conditions (e.g., de novo atherosclerosis, restinosis), intimal hyperplasia, arteriovenous fistula, macular degeneration, psoriasis, acne, hopeciareata, portwine spots, hair removal, rheumatoid and inflammatory arthrisis, joint conditions, lymph node conditions, and cognitive and behavioral conditions.

Accordingly, the invention in one embodiment provides methods utilizing the principle of energy transfer to and among molecular agents to control delivery and activation of pharmaceutically active agents such that delivery of the desired pharmacological effect is more focused, precise, and effective than the conventional techniques. Here, the energy transfer can include light from the phosphors or scintillators.

Although not intending to be bound by any particular theory or be otherwise limited in any way, the following theoretical discussion of scientific principles and definitions are provided to help the reader gain an understanding and appreciation of the present invention.

As used here, the term "subject" is not intended to be limited to humans, but may also include animals, plants, or any suitable biological organism.

As used herein, the phrase "a disease or condition" refers to a condition, disorder or disease that may include, but are not limited to, cancer, soft and bone tissue injury, chronic pain, wound healing, nerve regeneration, viral and bacterial infections, fat deposits (liposuction), varicose veins, enlarged prostate, retinal injuries and other ocular diseases, Parkinson's disease, and behavioral, perceptional and cognitive disorders. Exemplary conditions also may include nerve (brain) imaging and stimulation, a direct control of brain cell activity with light, control of cell death (apoptosis), and alteration of cell growth and division. Yet other exemplary a condition, disorder or disease may include, but are not limited to, cardiac ablasion (e.g., cardiac arrhythmi- and atrial fibrillation), photoangioplastic conditions (e.g., de novo atherosclerosis, restinosis), intimal hyperplasia, arteriovenous fistula, macular degeneration, psoriasis, acne, hopeciareata, portwine spots, hair removal, rheumatoid and inflammatory arthritis, joint conditions, and lymph node conditions.

As used here, the term "target structure" refers to an eukaryotic cell, prokaryotic cell, a subcellular structure, such as a cell membrane, a nuclear membrane, cell nucleus, nucleic acid, mitochondria, ribosome, or other cellular organelle or component, an extracellular structure, virus or prion, and combinations thereof.

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, regulation of cytochrome c oxidase and flavoproteins, activation of mitochondria, stimulation antioxidant protective pathway, modulation of cell growth and division, alteration of firing pattern of nerves, alteration of redox properties, generation of reactive oxygen species, modulation of the activity, quantity, or number of intracellular components in a cell, modulation of the activity, quantity, or number of extracellular components produced by, excreted by, or associated with a cell, or a combination thereof. Predetermined cellular changes may or may not result in destruction or inactivation of the target structure.

As used here, an "energy modulation agent" refers to an agent that is capable of receiving an energy input from a source and then re-emitting a different energy to a receiving target. Energy transfer among molecules may occur in a number of ways. The form of energy may be electronic, thermal, electromagnetic, kinetic, or chemical in nature. Energy may be transferred from one molecule to another (intermolecular transfer) or from one part of a molecule to another part of the same molecule (intramolecular transfer). For example, a modulation agent may receive electromagnetic energy and re-emit the energy in the form of thermal energy. In various embodiments, the energy modulation agents receive higher energy (e.g. x-ray) and re-emits in lower energy (e.g. UV-A). Some modulation agents may have a very short energy retention time (on the order of fs, e.g. fluorescent molecules) whereas others may have a very long half-life (on the order of minutes to hours, e.g. luminescent or phosphorescent molecules). Suitable energy modulation agents include, but are not limited to, a phosphor, a scintillator, a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, an up-converter, and a lanthanide chelate capable of intense luminescence. Various exemplary uses of these are described below.

The modulation agents may further be coupled to a carrier for cellular targeting purposes. For example, a biocompatible molecule, such as a fluorescing metal nanoparticle or fluorescing dye molecule that emits in the UV-A band, may be selected as the energy modulation agent.

The energy modulation agent may be preferably directed to the desired site (e.g. a tumor) by systemic administration to a subject. For example, a UV-A emitting energy modulation agent may be concentrated in the tumor site by physical insertion or by conjugating the UV-A emitting energy modulation agent with a tumor specific carrier, such as a lipid, chitin or chitin-derivative, a chelate or other functionalized carrier that is capable of concentrating the UV-A emitting source in a specific target tumor.

Additionally, the energy modulation agent can be used alone or as a series of two or more other energy modulation agents wherein the energy modulation agents provide an energy cascade. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the activatable pharmaceutical agent.

Signals that may be used to activate a corresponding agent may include, but are not limited to, photons of specific wavelengths (e.g. x-rays, ultraviolet, or visible light), electromagnetic energy (e.g. radio or microwave), thermal energy, acoustic energy, or any combination thereof.

Activation of the agent may be as simple as delivering the signal to the agent or may further premise on a set of activation conditions. For example, an activatable pharmaceutical agent, such as a photosensitizer, may be activated by UV-A radiation from the phosphors or scintillators of the invention. Once activated, the agent in its active-state may then directly proceed to effect a cellular change.

Where activation may further premise upon other conditions, mere delivery of the activation signal may not be sufficient to bring about the desired cellular change. For example, a photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors.

Selection of an activatable pharmaceutical agent greatly depends on a number of factors such as the desired cellular change, the desired form of activation, as well as the physical and biochemical constraints that may apply. Exemplary activatable pharmaceutical agents may include, but are not limited to, agents that may be activated by photonic energy, electromagnetic energy, acoustic energy, chemical or enzymatic reactions, thermal energy, or any other suitable activation mechanisms.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

In one embodiment, the activatable pharmaceutical agent is capable of chemically binding to the DNA or mitochondria a therapeutically effective amount. In this embodiment, the activatable pharmaceutical agent, preferably a photoactivatable agent, is exposed in situ to an activating energy emitted from an energy modulation agent, which, in turn receives energy from an initiation energy source. An activatable agent may be a small molecule; a biological molecule such as a protein, a nucleic acid or lipid; a supramolecular assembly; a nanoparticle; or any other molecular entity having a pharmaceutical activity once activated.

The activatable agent may be derived from a natural or synthetic origin. Any such molecular entity that may be activated by a suitable activation signal source to effect a predetermined cellular change may be advantageously employed in the present invention.

Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

The initiation energy source can be any energy source capable of providing energy at a level sufficient to cause cellular changes directly or via modulation agent which transfer the initiation energy to energy capable of causing the predetermined cellular changes. Also, the initiation energy source can be any energy source capable of providing energy at a level sufficient activate the activatable agent directly, or to provide the energy to a modulation agent with the input needed to emit the activation energy for the activatable agent (indirect activation). In one embodiment, the initiation energy is capable of penetrating completely through the subject. Within the context of the invention, the phrase "capable of penetrating completely through the subject" is used to refer to energy that can penetrate to any depth within the subject to activate the activatable pharmaceutical agent. It is not required that the any of the energy applied actually pass completely through the subject, merely that it be capable of doing so in order to permit penetration to any desired depth to activate the activatable pharmaceutical agent. Exemplary initiation energy sources that are capable of penetrating completely through the subject include, but are not limited to, UV light, visible light, IR radiation, x-rays, gamma rays, electron beams, microwaves and radio waves.

An additional embodiment of the invention is to provide a method for treatment of a condition, disease or disorder by the in-situ generation of energy in a subject in need thereof, where the energy generated can be used directly to effect a change thereby treating the condition, disease or disorder, or the energy can be used to activate an activatable pharmaceutical agent, which upon activation effects a change thereby treating the condition, disease or disorder. The energy can be generated in-situ by any desired method, including, but not limited to, chemical reaction such as chemiluminescence, or by conversion of an energy applied to the subject externally, which is converted in-situ to a different energy (of lower or higher energy than that applied), through the use of one or more energy modulation agents.

A further embodiment of the invention combines the treatment of a condition, disease or disorder with the generation of heat in the affected target structure in order to enhance the effect of the treatment. For example, in the treatment of a cell proliferation disorder using a photoactivatable pharmaceutical agent (such as a psoralen or derivative thereof), one can activate the photoactivatable pharmaceutical agent by applying an initiation energy which, directly or indirectly, activates the pharmaceutical agent. As noted elsewhere in this application, this initiation energy can be of any type, so long as it can be converted to an energy suitable for activating the pharmaceutical compound. In addition to applying this initiation energy, in this embodiment of the present invention, an energy is applied that causes heating of the target structure. In the case of a cell proliferation disorder such as cancer, the heating would increase the proliferation rate of the cancer cells. While this may seem counterintuitive at first, when the cell proliferation disorder is being treated using a DNA intercalation agent, such as psoralen or a derivative thereof, this increase in cell proliferation can actually assist the psoralen in causing apoptosis. In particular, when psoralen becomes intercalated into DNA, apoptosis occurs when the cell goes through its next division cycle. By increasing the rate at which the cells divide, one can use the present invention methods to enhance the onset of apoptosis.

In one embodiment, heat can be generated by any desired manner. Preferably, the heat can be generated using the application of microwaves or NIR energy to the target structure or by the use of use of nanoparticles of metal or having metal shells. Heat can also be generated by the absorption of light from the phosphors or scintillators of the invention. Alternatively, as is done in tumor thermotherapy, magnetic metal nanoparticles can be targeted to cancer cells using conventional techniques, then used to generate heat by application of a magnetic field to the subject under controlled conditions. (DeNardo S J, DeNardo G L, Natarajan A et al.: Thermal dosimetry predictive of efficacy of 111In-ChL6 NPAMF-induced thermoablative therapy for human breast cancer in mice. J. Nucl. Med. 48(3), 437-444 (2007).)

In another embodiment, the patient's own cells are removed and genetically modified to provide photonic emissions. For example, tumor or healthy cells may be removed, genetically modified to induce bioluminescence and may be reinserted at the site of the disease or condition to be treated. The modified, bioluminescent cells may be further modified to prevent further division of the cells or division of the cells only so long as a regulating agent is present.

In a further embodiment, a biocompatible emitting source, such as a fluorescing metal nanoparticle or fluorescing dye molecule or the phosphors or scintillators of the invention, is selected that emits in the UV-A band. The UV-A emitting source is directed to the site of a disease or condition. The UV-A emitting source may be directed to the site of the disease or condition by systemically administering the UV-A emitting source. Preferably, the UV-A emitting source is concentrated in the target site, such as by physical insertion or by conjugating the UV-A emitting molecule with a specific carrier that is capable of concentrating the UV-A emitting source in a specific target structure, as is known in the art.

In another embodiment, a UV- or light-emitting luciferase is selected as the emitting source for exciting a photoactivatable agent. A luciferase may be combined with ATP or another molecule, which may then be oxygenated with additional molecules to stimulate light emission at a desired wavelength. Alternatively, a phosphorescent emitting source may be used. One advantage of a phosphorescent emitting source is that the phosphorescent emitting molecules or other source may be electroactivated or photoactivated prior to insertion into a target site either by systemic administration or direct insertion into the region of the target site. Alternatively, some of these materials can be activated, with the energy being "stored" in the activated material, until emission is stimulated by application of another energy. For example, see the discussion in U.S. Pat. No. 4,705,952 (incorporated by reference in its entirety) regarding infrared-triggered phosphors.

Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state.

Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

Among various materials, luminescent nanoparticles have attracted increasing technological and industrial interest. In the context of the invention, nanoparticle refers to a particle having a size less than one micron. While the description of the invention describes specific examples using nanoparticles, the invention in many embodiments is not limited to particles having a size less than one micron. However, in many of the embodiments, the size range of having a size less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

In an additional embodiment, the photoactivatable agent can be a photocaged complex having an active agent contained within a photocage. The active agent is bulked up with other molecules that prevent it from binding to specific targets, thus masking its activity. When the photocage complex is photoactivated, the bulk falls off, exposing the active agent. In such a photocage complex, the photocage molecules can be photoactive (i.e. when photoactivated, they are caused to dissociate from the photocage complex, thus exposing the active agent within), or the active agent can be the photoactivatable agent (which when photoactivated causes the photocage to fall off), or both the photocage and the active agent are photoactivated, with the same or different wavelengths. For example, a toxic chemotherapeutic agent can be photocaged, which will reduce the systemic toxicity when delivered. Once the agent is concentrated in the tumor, the agent is irradiated with an activation energy. This causes the "cage" to fall off, leaving a cytotoxic agent in the tumor cell. Suitable photocages include those disclosed by Young and Deiters in "Photochemical Control of Biological Processes", *Org. Biomol. Chem.*, 5, pp. 999-1005 (2007) and "Photochemical Hammerhead Ribozyme Activation", *Bioorganic & Medicinal Chemistry Letters*, 16(10), pp. 2658-2661 (2006), the contents of which are hereby incorporated by reference.

In one embodiment, the use of light (e.g. light emitted from the phosphor or scintillator particles or combination thereof) for uncaging a compound or agent is used for elucidation of neuron functions and imaging, for example, two-photon glutamine uncaging (Harvey C D, et al., Nature, 450:1195-1202 (2007); Eder M, et al., Rev. Neurosci., 15:167-183 (2004)). Other signaling molecules can be released by UV light stimulation, e.g., GABA, secondary messengers (e.g., $Ca^{2+}$ and $Mg^{2+}$), carbachol, capsaicin, and ATP (Zhang F., et al., 2006). Chemical modifications of ion channels and receptors may be carried out to render them light-responsive. $Ca^{2+}$ is involved in controlling fertilization, differentiation, proliferation, apoptosis, synaptic plasticity, memory, and developing axons. In yet another preferred embodiment, $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

Genetic targeting allows morphologically and electrophysiologically characterization of genetically defined cell populations. Accordingly, in an additional embodiment, a light-sensitive protein is introduced into cells or live subjects via number of techniques including electroporation, DNA microinjection, viral delivery, liposomal transfection, creation of transgenic lines and calcium-phosphate precipitation. For example, lentiviral technology provides a convenient combination a conventional combination of stable long-term expression, ease of high-titer vector production and low immunogenicity. The light-sensitive protein may be, for example, channelrhodopsin-2 (ChR2) and chloride pump halorhodopsin (NpHR). The light protein encoding gene(s) along with a cell-specific promoter can be incorporated into the lentiviral vector or other vector providing delivery of the light-sensitive protein encoding gene into a target cell. ChR2 containing a light sensor and a cation channel, provides electrical stimulation of appropriate speed and magnitude to activate neuronal spike firing, when the cells harboring Ch2R are pulsed with light.

In one embodiment, a lanthanide chelate capable of intense luminescence can be used. For example, a lanthanide chelator may be covalently joined to a coumarin or coumarin derivative or a quinolone or quinolone-derivative sensitizer. Sensitizers may be a 2- or 4-quinolone, a 2- or 4-coumarin, or derivatives or combinations of these examples. A carbostyril 124 (7-amino-4-methyl-2-quinolone), a coumarin 120 (7-amino-4-methyl-2-coumarin), a coumarin 124 (7-amino-4-(trifluoromethyl)-2-coumarin), aminoinethyltrimethylpsoralen or other similar sensitizer may be used. Chelates may be selected to form high affinity complexes with lanthanides, such as terbium or europium, through chelator groups, such as DTPA. Such chelates may be coupled to any of a wide variety of well known probes or carriers, and may be used for resonance energy transfer to a psoralen or psoralen-derivative, such as 8-MOP, or other photoactive molecules capable of binding DNA. In one alternative example, the lanthanide chelate is localized at the site of the disease using an appropriate carrier molecule, particle or polymer, and a source of electromagnetic energy is introduced by minimally invasive procedures (e.g., the gas containing upconverters of the invention) to irradiate the target structure, after exposure to the lanthanide chelate and a photoactive molecule.

In another embodiment, a biocompatible, endogenous fluorophore emitter can be selected to stimulate resonance energy transfer to a photoactivatable molecule. A biocompatible emitter (e.g. the phosphors or scintillators) with an emission maxima within the absorption range of the biocompatible, endogenous fluorophore emitter may be selected to stimulate an excited state in fluorophore emitter. One or more halogen atoms may be added to any cyclic ring structure capable of intercalation between the stacked nucleotide bases in a nucleic acid (either DNA or RNA) to confer new photoactive properties to the intercalator. Any intercalating molecule (psoralens, coumarins, or other polycyclic ring structures) may be selectively modified by halogenation or addition of non-hydrogen bonding ionic substituents to impart advantages in its reaction photochemistry and its competitive binding affinity for nucleic acids over cell membranes or charged proteins, as is known in the art.

Skin photosensitivity is a major toxicity of photosensitizers. Severe sunburn occurs if skin is exposed to direct sunlight for even a few minutes. Early murine research hinted at a vigorous and long term stimulation of immune response; however, actual clinical testing has failed to achieve the early promises of photodynamic therapies. The early photosensitizers for photodynamic therapies targeted type II responses, which created singlet oxygen when photoactivated in the presence of oxygen. The singlet oxygen caused cellular necrosis and was associated with inflammation and an immune response. Some additional photosensitizers have been developed to induce type I responses, directly damaging cellular structures.

Porfimer sodium (Photofrin; QLT Therapeutics, Vancouver, BC, Canada), is a partially purified preparation of hematoporphyrin derivative (HpD). Photofrin has been approved by the US Food and Drug Administration for the treatment of obstructing esophageal cancer, microinvasive endobronchial non-small cell lung cancer, and obstructing endobronchial non-small cell lung cancer. Photofrin is activated with 630 nm, which has a tissue penetration of approximately 2 to 5 mm. Photofrin has a relatively long duration of skin photosensitivity (approximately 4 to 6 weeks).

Tetra (m-hydroxyphenyl) chlorin (Foscan; Scotia Pharmaceuticals, Stirling, UK), is a synthetic chlorine compound that is activated by 652 nm light. Clinical studies have demonstrated a tissue effect of up to 10 mm with Foscan and 652 nm light. Foscan is more selectively a photosensitizer in tumors than normal tissues, and requires a comparatively short light activation time. A recommended dose of 0.1 mg/kg is comparatively low and comparatively low doses of light may be used. Nevertheless, duration of skin photosensitivity is reasonable (approximately 2 weeks). However, Foscan induces a comparatively high yield of singlet oxygen, which may be the primary mechanism of DNA damage for this molecule.

Motexafin lutetium (Lutetium texaphryin) is activated by light in the near infrared region (732 nm). Absorption at this wavelength has the advantage of potentially deeper penetration into tissues, compared with the amount of light used to activate other photosensitizers. Lutetium texaphryin also has one of the greatest reported selectivities for tumors compared to selectivities of normal tissues. Young S W, et al.: Lutetium texaphyrin (PCI-0123) a near-infrared, water-soluble photosensitizer. Photochem Photobiol 1996, 63:892-897. In addition, its clinical use is associated with a shorter duration of skin photosensitivity (24 to 48 hours). Lutetium texaphryin has been evaluated for metastatic skin cancers. It is currently under investigation for treatment of recurrent breast cancer and for locally recurrent prostate cancer. The high selectivity for tumors promises improved results in clinical trials.

In general, the approach may be used with any source for the excitation an activatable molecule. The process may be a photopheresis process or may be similar to photophoresis. While photophoresis is generally thought to be limited to photonic excitation, such as by UV-light, other forms of radiation may be used as a part of a system to activate an activatable molecule. Light emission can stimulate the activation of an activatable molecule, such as 8-MOP. In one example, light emission from the phosphors or scintillators of the invention is directed at a solid tumor and stimulates, directly or indirectly, activation of 8-MOP.

In yet another embodiment, the activatable pharmaceutical agent, preferably a photoactive agent, is directed to a receptor site by a carrier having a strong affinity for the receptor site. The carrier may be a polypeptide and may form a covalent bond with a photo active agent, for example. The polypeptide may be an insulin, interleukin, thymopoietin or transferrin, for example. Alternatively, a photoactive pharmaceutical agent may have a strong affinity for the target cell without a binding to a carrier.

For example, a treatment may be applied that acts to slow or pause mitosis. Such a treatment is capable of slowing the division of rapidly dividing healthy cells or stem cells without pausing mitosis of cancerous cells. Thus, the difference in growth rate between the non-target cells and target cells are further differentiated to enhance the effectiveness of the methods of the invention.

In a further embodiment, methods in accordance with the invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

In another aspect, the invention also provides methods for producing an autovaccine, including: (1) providing a population of targeted cells; (2) treating the cells ex vivo with a psoralen or a derivative thereof; (3) activating the psoralen with an initiation energy source to induce a predetermined change in a target structure in the population of the target cells; and (4) returning the treated cells back to the host to induce an autovaccine effect against the targeted cell, wherein the treated cells cause an autovaccine effect.

Photobiomodulation

Photobiomodulation also known as low level laser therapy (LLLT), cold laser therapy, and laser biostimulation, is an emerging medical and veterinary technique in which exposure to low-level laser light can stimulate or inhibit cellular function leading to beneficial clinical effects. The "best" combination of wavelength, intensity, duration and treatment interval is complex and sometimes controversial with different diseases, injuries and dysfunctions needing different treatment parameters and techniques.

In one embodiment of this invention, the above-described energy modulation agents (phosphors, scintillators, fluorescent materials, and combinations and agglomerations thereof) with or without plasmonic inducing agents provide the light for producing photobiomodulation. Certain wavelengths of light emitted from the phosphor or scintillator configurations of the invention at certain intensities will, for example, aid tissue regeneration, resolve inflammation, relieve pain and boost the immune system. Observed biological and physiological effects to be expected include changes in cell membrane permeability, and up-regulation and down-regulation of adenosine triphosphate and nitric oxide.

All light-induced biological effects depend on the parameters of the irradiation (wavelength, dose, intensity, irradiation time, depth of a target cell, and continuous wave or pulsed mode, pulse parameters). (See, e.g., Karu I T, Low-Power Laser Therapy", in Biomedical Photonics Handbook, Vo-Dinh T. Ed., CRC Press, Boca Raton, Fla., pp. 48-1 to 48-25, (2003)). The phosphor or scintillator configurations of the invention can be programmed or instructed to deliver light comparable to that of known photobiomodulation treatments. For example, the phosphor or scintillator configurations of the invention can be programmed or instructed to deliver light with an average power typically in the range of 1-500 mW; or with peak power and short pulse width in the range of 1-100 W with 200 ns pulse widths. In this example, the average beam irradiance would typically be 10 mW/cm$^2$-5 W/cm$^2$. The phosphor or scintillator configurations of the invention can be programmed or instructed to or configured to deliver light at a wavelength typically in the range 600-1000 nm. The red-to-near infrared (NIR) region is preferred for photobiomodulation. Other wavelengths may be also used, e.g., UV light for neurons and green light for prostate tissue. Maximum biological responses have been seen to occur from prior work when the tissues were irradiated at 620, 680, 760, and 820-830 nm (Karu T I, et al., (1998).

In another embodiment, a plurality of sources for supplying electromagnetic radiation energy or energy transfer are provided by one or more molecules administered to a patient. The molecules may emit stimulating radiation in the correct band of wavelength to stimulate the target structure directly or to simulate the photoactivatable agents, or the molecules may transfer energy by a resonance energy transfer or other mechanism directly to the target structure or the photoactivatable agent or indirectly by a cascade effect via other molecular interactions.

The phenomenon of ultra weak emission from cellular systems has been a topic of various inquiries since the 1900s. This topic can be traced back to the early investigations of the Russian biologist Gurwitsch Alexander G. Gurwitsch more than seventy years ago, who speculated that ultraweak photon emission transmit information in cells [A. G. Gurwitsch, S. S. Grabje, and S. Salkind, "Die Natur des spezifischen Erregers der Zellteilung," *Arch. Entwicklungsmech. Org.* 100, 11-40, 1923].

In the 1970s, this area of research was investigated by a number of investigators. The presence of biological radiation from a variety of cells was later investigated by several research groups in Europe and Japan using low-noise, sensitive photon-counting detection systems [B. Ruth and F.-A. Popp, "Experimentelle Untersuchungen zur ultraschwachen Photonenemission biologischer Systeme," *Z. Naturforsch., A: Phys. Sci.* 31c, 741-745, 1976; T. I. Quickenden and S. S. Que-Hee, "The spectral distribution of the luminescence emitted during growth of the yeast *Saccharomyces cerevisiae* and its relationship to mitogenetic radiation," *Photochem. Photobiol.* 23, 201-204, 1976; H. Inaba, Y. Shimizu, Y. Tsuji, and A. Yamagishi, "Photon counting spectral analysing system of extra-weak chemi- and bioluminescence for biochemical applications," *Photochem. Photobiol.* 30, 169-175, 1979]. Popp and coworkers suggested the evidence of some 'informational character' associated with the ultra-weak photon emission from biological systems, often referred by Popp as "bio-photons". Other studies reported ultra-weak photon emission from various species including plant, and animals cells [H. J. Niggli, C. Scaletta, Y. Yan, F.-A. Popp, and L. A. Applegate, "Ultraweak photon emission in assessing bone growth factor efficiency using fibroblastic differentiation," *J. Photochem. Photobiol., B*, 64, 62-68, 2001;]. Results of experiments of UV-irradiated skin fibroblasts indicated that repair deficient xeroderma pigmentosum cells show an efficient increase of ultraweak photon emission in contrast to normal cells. [H. J. Niggli, "Artificial sunlight irradiation induces ultraweak photon emission in human skin fibroblasts," *J. Photochem. Photobiol., B* 18, 281-285 (1993)].

A delayed luminescence emission was also observed in biological systems [F.-A. Popp and Y. Yan, "Delayed luminescence of biological systems in terms of coherent states," *Phys. Lett. A* 293, 93-97 (2002); A. Scordino, A. Triglia, F. Musumeci, F. Grasso, and Z. Rajfur, "Influence of the presence of Atrazine in water on in-vivo delayed luminescence of acetabularium acetabulum," *J. Photochem. Photobiol., B,* 32, 11-17 (1996); This delayed luminescence was used in quality control of vegetable products [A. Triglia, G. La Malfa, F. Musumeci, C. Leonardi, and A. Scordino, "Delayed luminescence as an indicator of tomato fruit quality," *J. Food. Sci.* 63, 512-515 (1998)] or for assessing the quality or quality changes of biological tissues [Yu Yan, Fritz-Albert Popp *, Sibylle Sigrist, Daniel Schlesinger, Andreas Dolf, Zhongchen Yan, Sophie Cohen, Amodsen Chotia, "Further analysis of delayed luminescence of plants", *Journal of Photochemistry and Photobiology B: Biology* 78, 235-244 (2005)].

It was reported that UV excitation can further enhance the ultra-weak emission and a method for detecting UV-A-laser-induced ultra-weak photon emission was used to evaluate differences between cancer and normal cells. [H. J. Niggli et al, Laser-ultraviolet-A-induced ultraweak photon emission in mammalian cells, *Journal of Biomedical Optics* 10(2), 024006 (2005)].

Accordingly, in one embodiment of the present invention, upon applying an initiation energy from at least one source to a target structure in a subject in need of treatment, the initiation energy contacts the target structure and induces a predetermined change in said target structure in situ, wherein the predetermined change is the enhancement of energy emission from the target, which then mediates, initiates or enhances a biological activity of other target structures in the subject, or of a second type of target structure (e.g., a different cell type).

In another embodiment, the initiation energy can itself be energy emitted by at least one cell excited by metabolic processes or some other internal or external trigger, and said applying is conducted via cell-to-cell energy transfer. There are those that maintain that the health of the body depends on certain bioelectric vibrations that are susceptible to chemical or physical toxic factors. Frohlich notes that there are coherent electric vibrations in the frequency range 100 GHz to 1 THz, excited in cells by metabolic processes (see Frohlich H. Coherent electric vibrations in biological systems and the cancer problem, IEEE Transactions on Microwave Theory and Techniques, Vol. MTT-26, No. 8, August, 1978, pp 613-617). This idea is based on observation of the inhibition or stimulation of the growth of yeast and bacterias functions of the applied frequency, showing very stable and repetitive resonances. If such vibrational states are indeed metabolically excited, then they should be manifested in Raman spectroscopy. Actually, their existence has been demonstrated during periods of metabolic activity of lysozyme and *E. coli* (700 GHz to 5 THz). Emissions have also been observed at lower frequencies (150 GHz or less). These vibrations occur in the tissue of higher organisms and they have been hypothesized exercise some control on cellular growth (see also S. J. Webb et al, Nature, Vol. 218, Apr. 27, 1968, pp. 374-375; and S. J. Webb et al et al, Nature Vol. 222, Jun. 21, 1969, pp. 1199-1200). Cancerization could result from a modification of these vibrations by the invasion of foreign molecules, e.g., the presence of free electrons in the condition bands of proteins. There is some evidence for the presence of double spectral lines at 1.5 and 6 THz in breast carcinoma, which may be an indication of an interaction between normal cellular vibrations and free electrons. In such coherent frequency communication between cells, it is believed that the medium through which the communication is transmitted is the water within and around the cells (see Smith, Coherent Frequencies, Consciousness and the Laws of Life, 9$^{th}$ International Conference CASYS '09 on *Computing Anticipatory Systems*, Liege, Belgium, Aug. 3-8, 2009).

Accordingly, in a further embodiment of the present invention, the initiation energy is an energy capable of triggering an altered metabolic activity in one or more cells, preferably in the 100 GHz to 10 THz region, and is applied directly to one or more cells, to trigger the cell(s) to undergo altered metabolic activity, and optionally, to further trigger emissions from the cell(s) to thereby cascade the effects of the emissions to other similar or different cell types adjacent thereto, in essentially a triggered entry into the natural emissions process described above, preferably where the medium through which the emissions are communicated is water-based, most preferably where the medium is the water contained within and surrounding the cells.

Indeed, FIG. 11A-2 as described above shows the combination of x-ray and microwave energy (e.g., 100 GHz to 10 THz region) applied to a target site. In this embodiment, the x-ray irradiation triggers light emission from energy modulation agents in the medium (phosphors, scintillators, fluorescent materials, and combinations and agglomerations thereof) with or without plasmonic inducing agents to activate photoactivatable agents in the medium (as discussed above), and the microwave and or RF radiation can cause the alignment of dipoles or alter the mass transport across ionic channels which in turn could trigger the cell(s) to undergo altered metabolic activity, or optionally, to further trigger emissions from the cell(s) to thereby cascade the effects of the emissions to other similar or different cell types adjacent thereto (as described above) to complement the photoactivated photoactivatable agents in the medium.

While not bound to the particular following theory, a photoacceptor first absorbs the light used for the irradiation. After promotion of electronically excited states, primary molecule processes from these states can lead to a measurable biological effect (via secondary biochemical reaction, or photosignal transduction cascade, or cellular signaling) at the cellular level. A photoacceptor for eukaryotic cells in red-to-NIR region is believed to be the terminal enzyme of the respiratory chain cytochrome c oxidase located in cell mitochondrion. In the violet-to blue spectra region, flavoprotein (e.g., NADHdehydrogenase in the beginning of the respiratory chain) is also among the photoacceptors. The phosphor configurations of the invention can be programmed or instructed to or configured to deliver light at these wavelengths.

Clinical applications of photobiomodulation include, for example, treating soft tissue and bone injuries, chronic pain, wound healing and nerve and sensory regeneration/restoration, and possibly even resolving viral and bacterial infections, treating neurological and phychiatric diseases (e.g., epilepsy and Parkinson's disease) (e.g., Zhang F., et al., Nature, 446:617-9 (Apr. 5, 2007; Han X., et al., PloS ONE, 2(3):e299 (Mar. 21, 2007); Arany P R, et al., Wound Repair Regen., 15(6):866-74 (2007); Lopes C B, et al., Photomed. Laser Surg., 25(2):96-101 (2007)). One clinical application showing great promise is the treatment of inflammation, where the anti-inflammatory effect of location-and-dose-specific laser irradiation produces similar outcomes as NSAIDs, but without the potentially harmful side-effects (Bjordal J M, Couppe C, Chow R T, Tuner J, Ljunggren E A (2003). "A systematic review of low level laser therapy with location-specific doses for pain from chronic joint disorders". The Australian journal of physiotherapy 49(2): 107-16). The phosphor configurations of the invention can be programmed or instructed to or configured to deliver light at the wavelengths and illuminations reported in this work.

An NIR light treatment can prevent cell death (apoptosis) in cultured neurons (brain) cells (Wong-Reiley M T, et al., JBC, 280(6):4761-71 (2005)). Specific wavelengths of light can promote cellular proliferation to the activation of mitochondria, the energy-producing organelles within the cell via cytochrome c oxidase. An NIR treatment can augment mitochondrial function and stimulate antioxidant protective pathways. The evidence that the NIR treatment can augment mitochondrial function and stimulate antioxidant protective pathways comes from photobiomodulation experiments carried out using a laboratory model of Parkinson's disease (PD) (cultures of human dopaminergic neuronal cells) (Whelan H., et. al., SPIE, Newsroom, pages 1-3 (2008)). The phosphor or scintillator configurations of the invention can be programmed or instructed to or configured to deliver light at these NIR wavelengths.

It has also been shown that light has both inductive and inhibitory effect on cell growth and division in a red tide flagellate, *Chattonellantique* (Nemote Y., Plant and Cell Physiol., 26(4):669-674 (1985)). The phosphor or scintillator configurations of the invention can be programmed or instructed to or configured to deliver light at these wavelengths.

When the excitable cells (e.g., neurons, cardiomyocites) are irradiated with monochromatic visible light, the photoacceptors are also believed to be components of respiratory chain. It is clear from experimental data (Karu, T. I., (2002). Low-power laser therapy. In: CRC Biomedical Photonics Handbook, T. Vo-Dinh, Editor-in-Chief, CRC Press, Boca Raton (USA)) that irradiation can cause physiological and morphological changes in nonpigmental excitable cells viabsorption in mitochondria. Later, similar irradiation experiments were performed with neurons in connection with low-power laser therapy. It was shown in 80's that He—Ne laser radiation alters the firing pattern of nerves; it was also found that transcutaneous irradiation with HeNe laser mimicked the effect of peripheral stimulation of a behavioral reflex. These findings were found to be connected with pain therapy (Karu T I, et al., (2002)). The phosphor configurations of the invention can be programmed or instructed to or configured to deliver light at these wavelengths.

When photoacceptors absorb photons, electronic excitation followed by photochemical reactions occurring from lower excitation states (first singlet and triplet) takes place. It is also known that electronic excitation of absorbing centers alters their redox properties. Until yet, five primary reactions have been discussed in literature (Karu T I, et al., (2002)). Two of them are connected with alteration of redox properties and two mechanisms involve generation of reactive oxygen species (ROE). Also, induction of local transient (very short time) heating of absorbing chromophores is possible. Details of these mechanisms can be found in (Karu T I, et. al., (2002); Karu T I, et al., (1998). The Science of Low Power Laser Therapy. Gordon and Breach Sci. Publ., London). The phosphor or scintillator configurations of the invention can be programmed or instructed to or configured to deliver light at these wavelengths.

Photobiological action via activation of respiratory chain is believed to be a general mechanism occurring in cells. Crucial events of this type of cell metabolism activation are occurring due to a shift of cellular redox potential into more oxidized direction as well as due to ATP extrasynthesis. Susceptibility to irradiation and capability for activation depend on physiological status of irradiated cells: the cells, which overall redox potential is shifted to more reduced state (example: some pathological conditions) are more sensitive to the irradiation. The specificity of final photobiological response is determined not at the level of primary reactions in the respiratory chain but at the transcription level during cellular signaling cascades. In some cells, only partial activation of cell metabolism happens by this mechanism (example: redox priming of lymphocytes). The phosphor or scintillator configurations of the invention can be programmed or instructed to or configured to deliver light at these wavelengths.

Far red and NIR radiation have been shown to promote wound healing, e.g., infected, ischemic, and hypoxic wounds (Wong-Reley, WTT, JBC, 280(6):4761-4771 (2005)). Red-to-NIR radiation also protects the retina against the toxic actions of methanol-derived formic acid in a rodent model of methanol toxicity and may enhance recovery from retinal injury and other ocular diseases in which mitochondrial dysfunction is postulated to play a role (Eells J T., PNAS, 100(6):3439-44 (2003)). Another clinical application of photobiomodulation is repair of soft and bone tissues by IR laser irradiation (Martinez M E, et al., Laser in Med. Sci., 2007). Invasive laser assisted liposuction is a recently developed method, wherein a laser fiber is introduced through a tube into the skin and directly to the fat cells causing the cells to rapture and drain away as liquid (Kim K H, Dermatol. Surg., 32(2):241-48 (2006)). Tissue around the area is coagulated. Yet, another application of photobiomodulation is a non-surgical varicose vein treatment (an endovenous laser therapy), wherein a laser is threaded through an incision and the full length of the varicose vein (Kim H S, J. Vasc. Interv. Radiol., 18(6):811 (2007)). When the laser is slowly withdrawn, heat is applied to the vein walls, causing the vein to permanently close and disappear. The phosphor or scintillator configurations of the invention can be programmed or instructed to or configured to deliver light at these wavelengths.

The green light laser is a laser that vaporizes and removes the enlarged prostate tissue (Heinrich E., Eur. Urol., 52(6): 1632-7 (2007)). The significance of the color of the laser light (green) is that this results in absorption by hemoglobin which is contained within red blood cells and not absorbed by water. The procedure may also be known as laser prostatectomy or laser Transurethral resection of the prostate (TURP). The technique involves painting the enlarged prostate with the laser until the capsule of the prostate is reached. By relieving this portion of the prostate, patients are able to void much easier through a wide-open channel in the prostate. The procedure needs to be performed under general or spinal anesthesia. An advantage of the procedure is that even patients taking blood thinners (e.g., aspirin to prevent stroke) can be treated because there is less bleeding compared to a traditional surgery. The phosphor configurations of the invention can be programmed or instructed to or configured to deliver light at these wavelengths.

Yet, another area of application of photobiomodulation is a direct control of brain cell activity with light. The technique is based upon NIR spectroscopy and is simpler to use and less expensive than other methods such as functional magnetic resonance imaging and positron emission tomography.

Whenever a region of the brain is activated, that part of the brain uses more oxygen. This technique works by measuring the blood flow and oxygen consumption in the brain. The light emitted by NIR laser diodes is carried through optical fibers to a person's head. The light penetrates the skull where it assesses the brain's oxygen level and blood volume. The scattered light is then collected by optical fibers, sent to detectors and analyzed by a computer. By examining how much of the light is scattered and how much is absorbed, portions of the brain and extract information about brain activity can be mapped. By measuring the scattering, it is determined where the neurons are firing. This means that scientists can simultaneously detect both blood profusion and neural activity. The technique could be used in many diagnostic, prognostic and clinical applications. For example, it could be used to find hematomas in children, to study blood flow in the brain during sleep apnea, and to monitor recovering stroke patients on a daily, or even hourly, basis (that would be impractical to do with MRI). To validate the technique, hemoglobin oxygen concentrations in the brain obtained simultaneously by NIR spectroscopy and by functional MRI, the current "gold standard" in brain studies, was compared. Both methods were used to generate functional maps of the brain's motor cortex during a periodic sequence of stimulation by finger motion and rest. Spatial congruence between the hemoglobin signal and the MRI signal in the motor cortex related to finger movement was demonstrated. The researchers also demonstrated collocation between hemoglobin oxygen levels and changes in scattering due to brain activities. The changes in scattering associated with fast neuron signals came from exactly the same locations. The phosphor or scintillator configurations of the invention can be programmed or instructed to or configured to deliver light at these wavelengths.

A low-intensity laser light-oxygen cancer therapy is another application of photobiomodulation. The light-oxygen effect (LOE), which involves activation of or damage to biosystems by optical radiation at low optical doses by direct photoexcitation of molecular oxygen dissolved in a biosystem so that it is converted to the singlet state, i.e., by photogeneration of molecular singlet oxygen from $O_2$ dissolved in cells, similar to photodynamic effect (Zakharov S D, et al., Quantum Electronics, 29(12):1031-53 (1999)). It was shown that the He—Ne laser radiation destroys tumor cells in the presence or absence of the photosensitiser. The LOE can be activated by small optical doses, which are 4-5 orders of magnitude lower that those found if a comparison is made with the familiar analogue in the form of the photodynamic effect (PDE). The phosphor or scintillator configurations of the invention can be programmed or instructed to or configured to deliver light at these wavelengths.

Another type of photobiomodulation methods fall into two general categories: one set of methods uses light to uncage a compound that then becomes biochemically active, binding to a downstream effector; the other set uses light to activate a light-sensitive protein such as rhodopsin (ChR2), which can then excite the cell expressing the opsin. The phosphor or scintillator configurations of the invention can be programmed or instructed to or configured to deliver light for these types of photobiomodulation.

In the first set, this method involves applying "caged" chemicals to a sample and then using light to open the cage to invoke a reaction. Modified glutamate is useful for finding excitatory connections between neurons, since the uncaged glutamate mimics the natural synaptic activity of one neuron impinging upon another. This method is used for elucidation of neuron functions and imaging in brain slices using, for example, two-photon glutamine uncageing (Harvey C D, et al., Nature, 450:1195-1202 (2007); Eder M, et al., Rev. Neurosci., 15:167-183 (2004)). Other signaling molecules can be released by UV light stimulation, e.g., GABA, secondary messengers (e.g., $Ca^{2+}$ and $Mg^{2+}$), carbachol, capsaicin, and ATP (Zhang F., et al., 2006). Chemical modifications of ion channels and receptors may be carried out to render them light-responsive. $Ca^{2+}$ is involved in controlling fertilization, differentiation, proliferation, apoptosis, synaptic plasticity, memory, and developing axons. In yet another preferred embodiment, $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

In the second set which uses light to activate a light-sensitive protein such as rhodopsin (ChR2), which can then excite the cell expressing the opsin, It has been shown that channelrhodopsin-2, a monolithic protein containing a light sensor and a cation channel, provides electrical stimulation of appropriate speed and magnitude to activate neuronal spike firing. Recently, photoinhibition, the inhibition of neural activity with light, has become feasible with the application of molecules such as the light-activated chloride pump halorhodopsin to neural control. Together, blue-light activated channelrhodopsin-2 and the yellow light-activated chloride pump halorhodopsin enable multiple-color, optical activation and silencing of neural activity.

ChR2 photostimulation involves genetic targeting ChR2 to neurons and light pulsing the neurons expressing ChR2 protein. The experiments have been conducted in vitro and in vivo in mice by in vivo deep-brain photostimulaiton using optical fibers to deliver light into the lateral hypothalamus (Adamantidis A R, et al., Nature 450:420-425 (2007)). Genetic targeting of ChR2 allows exclusive stimulation of defined cellular subsets and avoids the need for addition of the caged glutamate, facilitating photostimulation in vivo (Wang H., et al., PNAS, 104(19):8143-48 (2007)). ChR2 photostimulation has been used for restoring visual activity in mice with impaired vision, to evoke behavioral responses in worms and flies (Wang H., et al., 2007). The robust associative learning induced by ChR2-assisted photostimulaiton in mice opens the door to study the circuit basis of perception and cognition in vivo (Huber D., et al., 2007). This kind of neuronal targeting and stimulation might have clinical application, e.g., deep brain stimulation to treat Parkinson's disease and other disorders, controlling behavioral, perceptional and cognitive characteristics, and for imaging and studying how the brain works (Zhang F., et al., Nature Methods, 3(10):785-792 (2006); Wong-Riley M T., et al., JBC, 280(6):4761-4771 (2005)).

Another gene, chloride pump (NpHR), which is borrowed from a microbe called an archaebacterium, can make neurons less active in the presence of yellow light. Combined, the two genes ChR2 and NpHR can now make neurons obey pulses of light like drivers obey a traffic signal: Blue means "go" (emit a signal), and yellow means "stop" (don't emit).

Light-sensitive proteins can be introduced into cells or live subjects via number of techniques including electroporation, DNA microinjection, viral delivery, liposomal transfection and calcium-phosphate precipitation.

Hence, in one embodiment of the invention, there is provided a system for modulating biological activity within a medium. The system includes a reduced-voltage x-ray source configured to generate x-rays from a peak applied cathode voltage at or below 80 kVp, and a plurality of energy-emitting particles in the medium which, upon radiation from the x-ray source, radiate at a lower energy than the x-ray source to alter the biological activity of the medium by photobiomodulation (as discussed above). The ranges of peak applied cathode voltage discussed above are applicable for photobiomodulation. The use of energy-emitting particles radiate with an intensity at least 10 times greater than that of $Y_2O_3$, upon exposure of $Y_2O_3$ to the radiation from an initiation source (or with the other greater intensities described above) are applicable for photobiomodulation. The use of first and second energy-emitting particles to produce a combination of emission from the first and second plurality of energy-emitting particles to produce a spectrum for illumination in the medium (as described above) applicable for direct or indirect (via a photoactivated agent) photobiomodulation.

Photostimulation

A photostimulation technique involves chemical modification of ion channels and receptors to render them light-responsive. The above-described energy modulation agents (phosphors, scintillators, fluorescent materials, and combinations and agglomerations thereof) with or without plasmonic inducing agents can be programmed or instructed to or configured to deliver light for this technique. Some of the most fundamental signaling mechanisms in a cell involve the release and uptake of $Ca^{2+}$ ions. $Ca^{2+}$ is involved in controlling fertilization, differentiation, proliferation, apoptosis, synaptic plasticity, memory, and developing axons. It has been shown that $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

Directly controlling a brain cell activity with light is a novel means for experimenting with neural circuits and could lead to therapies for some disorders. This accomplishment is a step toward the goal of mapping neural circuit dynamics on a millisecond timescale to see if impairments in these dynamics underlie severe psychiatric symptoms. Knowing the effects that different neurons have could ultimately help researchers figure out the workings of healthy and unhealthy brain circuits. If use of the technique can show that altered activity in a particular kind of neuron underlies symptoms, for example, this insight will allow development of targeted genetic or pharmaceutical treatments to fix those neurons. Conceivably, direct control of neuronal activity with light could someday become a therapy in itself. Here, the phosphor configurations of the invention can be programmed or instructed to or configured to deliver light for direct control of neuronal activity.

In living organisms, scientists have been able to cause worms, C. elegans, to stop swimming while their genetically altered motor neurons were exposed to pulses of yellow light intensified through a microscope. In some experiments, exposure to blue light caused the worms to wiggle in ways they weren't moving while unperturbed. When the lights were turned off, the worms resumed their normal behavior.

Meanwhile, in experiments in living brain tissues extracted from mice, the researchers were able to use the technique to cause neurons to signal or stop on the millisecond timescale, just as they do naturally. Other experiments showed that cells appear to suffer no ill effects from exposure to the light. The mice resume their normal function once the exposure ends.

The most direct application of an optical neuron control is experimenting with neural circuits to determine why unhealthy ones fail and how healthy ones work.

In patients with Parkinson's disease, for example, researchers have shown that electrical "deep brain stimulation" of cells can help patients, but they don't know precisely why. By allowing researchers to selectively stimulate or dampen different neurons in the brain, the light stimulation techniques could help in determining which particular neurons are benefiting from deep brain stimulation. That could lead to making the electrical treatment, which has some unwanted side effects, more targeted.

Another potential application is experimenting with simulating neural communications. Because neurons communicate by generating patterns of signals-sometimes on and sometimes off like the 0s and 1s of binary computer code-flashing blue and yellow lights in these patterns could compel neurons to emit messages that correspond to real neural instructions. In the future, this could allow researchers to test and tune sophisticated neuron behaviors. Much farther down the road, the ability to artificially stimulate neural signals, such as movement instructions, could allow doctors to bridge blockages in damaged spinal columns, perhaps restoring some function to the limbs of paralyzed patients.

Finally, the technique could be useful in teasing out the largely unknown functioning of healthy brains. Here, the phosphor or scintillator configurations of the invention can be programmed or instructed to or configured to deliver light for control of these and other neuron activities.

Hence, in one embodiment of the invention, there is provided a system for modulating biological activity within a medium. The system includes a reduced-voltage x-ray source configured to generate x-rays from a peak applied cathode voltage at or below 80 kVp, and a plurality of energy-emitting particles in the medium which, upon radiation from the x-ray source, radiate at a lower energy than the x-ray source to alter the biological activity of the medium by photostimulation (as discussed above). The ranges of peak applied cathode voltage discussed above are applicable for photobiomodulation. The use of energy-emitting particles radiate with an intensity at least 10 times greater than that of $Y_2O_3$, upon exposure of $Y_2O_3$ to the radiation from an initiation source (or with the other greater intensities described above) are applicable for photostimulation. The use of first and second energy-emitting particles to produce a combination of emission from the first and second plurality of energy-emitting particles to produce a spectrum for illumination in the medium (as described above) applicable for direct or indirect (via a photoactivated agent) photostimulation.

Photocuring with the Energy Modulation Agents of this Invention:

In this application, the above-described energy modulation agents (phosphors, scintillators, fluorescent materials, and combinations and agglomerations thereof) with or without plasmonic inducing agents are provided and distributed into an uncured polymer based medium for the activation of photosensitive agents in the medium to promote cross-linking and curing of the polymer based medium. For adhesive and surface coating applications, light activated processing is limited due to the penetration depth of UV light into the processed medium. In light activated adhesive and surface coating processing, the primary limitation is that the material to be cured must see the light—both in type (wavelength or spectral distribution) and intensity. This limitation has meant that one medium typically has to transmit the appropriate light. In adhesive and surface coating applications, any "shaded" area will require a secondary cure mechanism, increasing cure time over the non-shaded areas and further delaying cure time due to the existent of a sealed skin through which subsequent curing must proceed.

Conventionally, moisture-curing mechanisms, heat-curing mechanisms, and photo-initiated curing mechanisms are used to initiate cure, i.e., cross-linking, of reactive compositions, such as reactive silicones, polymers, and adhesives. These mechanisms are based on either condensation reactions, whereby moisture hydrolyzes certain groups, or addition reactions that can be initiated by a form of energy, such as electromagnetic radiation or heat.

The invention described herein can use any of the following light activated curing polymers as well as others known in the art to which the phosphors of this invention are added.

For example, one suitable light activated polymer compound includes UV curing silicones having methacrylate functional groups. U.S. Pat. No. 4,675,346 to Lin, the disclosure of which is hereby expressly incorporated herein by reference, is directed to UV curable silicone compositions including at least 50% of a specific type of silicone resin, at least 10% of a fumed silica filler and a photoinitiator, and cured compositions thereof. Other known UV curing silicone compositions suitable for the invention include organopolysiloxane containing a (meth)acrylate functional group, a photosensitizer, and a solvent, which cures to a hard film. Other known UV curing silicone compositions suitable for the invention include compositions of an organopolysiloxane having an average of at least one acryloxy and/or methacryloxy group per molecule; a low molecular weight polyacrylyl crosslinking agent; and a photosensitizer.

Loctite Corporation has designed and developed UV and UV/moisture dual curable silicone compositions, which also demonstrate high resistance to flammability and combustibility, where the flame-retardant component is a combination of hydrated aluminand a member selected from the group consisting of organo ligand complexes of transition metals, organosiloxane ligand complexes of transition metals, and combinations thereof. See U.S. Pat. Nos. 6,281,261 and 6,323,253 to Bennington. These formulations are also suitable for the invention.

Other known UV photoactivatable silicones include silicones functionalized with, for example, carboxylate, maleate, cinnamate and combinations thereof. These formulations are also suitable for the invention. Other known UV photoactivatable silicones suitable for the invention include benzoin ethers ("UV free radical generator") and a free-radical polymerizable functional silicone polymers, as described in U.S. Pat. No. 6,051,625 whose content is incorporated herein by reference in its entirety. The UV free radical generator (i.e., the benzoin ether) is contained at from 0.001 to 10 wt % based on the total weight of the curable composition. Free radicals produced by irradiating the composition function as initiators of the polymerization reaction, and the free radical generator can be added in a catalytic quantity relative to the polymerizable functionality in the subject composition.

Further included in these silicone resins can be silicon-bonded divalent oxygen atom compounds which can form a siloxane bond while the remaining oxygen in each case can be bonded to another silicon to form a siloxane bond, or can be bonded to methyl or ethyl to form an alkoxy group, or can be bonded to hydrogen to form silanol. Such compounds can include trimethylsilyl, dimethylsilyl, phenyldimethylsilyl, vinyldimethylsilyl, trifluoropropyldimethylsilyl, (4-vinylphenyl)dimethylsilyl, (vinylbenzyl)dimethylsilyl, and (vinylphenethyl)dimethylsilyl.

The photoinitiator component of this invention is not limited to those free radical generators given above, but may be any photoinitiator known in the art, including the aforementioned benzoin and substituted benzoins (such as alkyl ester substituted benzoins), Michler's ketone, dialkoxyacetophenones, such as diethoxyacetophenone ("DEAP"), benzophenone and substituted benzophenones, acetophenone and substituted acetophenones, and xanthone and substituted xanthones. Other desirable photoinitiators include DEAP, benzoin methyl ether, benzoin ethyl ether, benzoin isopropyl ether, diethoxyxanthone, chloro-thio-xanthone, azo-bisisobutyronitrile, N-methyl diethanolaminebenzophenone, and mixtures thereof. Visible light initiators include camphoquinone, peroxyester initiators and non-fluorene-carboxylic acid peroxyesters.

Commercially available examples of photoinitiators suitable for the invention include those from Vantico, Inc., Brewster, N.Y. under the IRGACURE and DAROCUR tradenames, specifically IRGACURE 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4,4-trimethyl pentyl) phosphine oxide and 2-hydroxy-2-methyl-1-phenyl-propan-1-one), and 819 [bis(2,4,6-trimethyl benzoyl)phenyl phosphine oxide] and DAROCUR 1173 (2-hydroxy-2-methyl-1-phenyl-1-propane) and 4265 (the combination of 2,4,6-trimethylbenzoyldiphenyl-phosphine oxide and 2-hydroxy-2-methyl-1-phenyl-propan-1-one); and IRGACURE 784DC (bis (.eta..sup.5-2,4-cyclopentadien-1-yl)-bis[2, 6-difluoro-3-(1H-pyrrol-1-yl)phenyl]titanium).

Generally, the amount of photoinitiator (or free radical generators) should be in the range of about 0.1% to about 10% by weight, such as about 2 to about 6% by weight. The free radical generator concentration for benzoin ether is generally from 0.01 to 5% based on the total weight of the curable composition.

A moisture cure catalyst can also be included in an amount effective to cure the composition. For example, from about 0.1 to about 5% by weight, such as about 0.25 to about 2.5% by weight, of the moisture cure catalyst can be used in the invention to facilitate the cure process beyond that of photo-activated curing. Examples of such catalysts include organic compounds of titanium, tin, zirconium and combinations thereof. Tetraisopropoxytitanate and tetrabutoxytitanate are suitable as moisture cure catalyst. See also U.S. Pat. No. 4,111,890, the disclosure of which is expressly incorporated herein by reference.

Included in the conventional silicone composition (and other inorganic and organic adhesive polymers) suitable for the invention are various inorganic fillers. For example, hollow microspheres supplied by Kish under the trade name Q-CEL are free flowing powders, white in color. Generally, these borosilicate hollow microspheres are promoted as extenders in reactive resin systems, ordinarily to replace heavy fillers, such as calcium carbonate, thereby lowering the weight of composite materials formed therewith. Q-CEL 5019 hollow microspheres are constructed of a borosilicate, with a liquid displacement density of 0.19 g/cm$^2$, a mean particle size of 70 microns, and a particle size range of 10-150 um. Other Q-CEL products are shown below in tabular form. Another commercially available hollow glass microsphere is sold by Kish under the trade name SPHERICEL. SPHEREICEL 110P8 has a mean particle size of about 11.7 microns, and a crush strength of greater than 10,000 psi. Yet other commercially available hollow glass microsphere are sold by the Schundler Company, Metuchen, N.J. under the PERLITE tradename, Whitehouse Scientific Ltd., Chester, UK and 3M, Minneapolis, Minn. under the SCOTCHLITE trade name.

In general, these inorganic filler components (and others such as fumed silica) add structural properties to the cured composition, as well as confers flowability properties to the composition in the uncured state and increase the transmissivity for the UV cure radiation. When present, the fumed silica can be used at a level of up to about 50 weight percent, with a range of about 4 to at least about 10 weight percent, being desirable. While the precise level of silica may vary depending on the characteristics of the particular silica and the desired properties of the composition and the reaction product thereof, care should be exercised by those persons of ordinary skill in the art to allow for an appropriate level of transmissivity of the inventive compositions to permit a UV cure to occur.

Desirable hydrophobic silicas include hexamethyldisilazane-treated silicas, such as those commercially available from Wacker-Chemie, Adrian, Mich. under the trade designation HDK-2000. Others include polydimethylsiloxane-treated silicas, such as those commercially available from Cabot Corporation under the trade designation CAB-O-SIL N70-TS, or Degussa Corporation under the trade designation AEROSIL R202. Still other silicas include trialkoxyalkyl silane-treated silicas, such as the trimethoxyoctyl silane-treated silica commercially available from Degussa under the trade designation AEROSIL R805; and 3-dimethyl dichlorosilane-treated silicas commercially available from Degussa under the trade designation R972, R974 and R976.

While these inorganic fillers have extended the use of conventional UV cured silicone systems to permit the curing of materials beyond a skin depth of UV penetration, these inorganic fillers alone do not overcome shadowing effects and suffer from UV scattering which effectively makes for a smaller penetration depth. In the invention described herein, the inclusion of these inorganic fillers along with phosphor or scintillator particles provide a mechanism by which uniform light activated cures can occur deep inside of the body of adhesive-solidified assemblies in regions that would normally be shadowed or not with the reach of external UV or other light sources.

Accordingly, in this example of the invention described herein, conventional silicone and polymeric adhesive or release or coating compositions are prepared using conventional mixing, heating, and incubation techniques. Included in these conventional compositions are the upconverter structures of the invention. These compositions can then be applied to surfaces of objects to be fixed together or to surfaces where a hard coating is desired or cast in a curable form for the production of molded objects. These compositions upon activation will produce radiant light for photoactivated cure of the polymer composition. The density of the phosphors in these compositions will depend on the "light transparency" of the luminescing particle containing composition. Where these compositions contain a significant amount of the inorganic filler as discussed above, the concentration of the phosphors or scintillators can be reduced for example as compared to a composition with a black color pigment where the light transparency will be significantly reduced.

U.S. Pat. No. 7,294,656 to Bach et al., the entire disclosure of which is incorporated herein by reference, describes a non-aqueous composition curable by UV radiation broadly containing a mixture of two UV curable urethane acrylates that have several advantages over conventional radiation-curable compositions. The Bache et al. compositions can be cured in a relatively short time using UV-C (200-280 nm), UV-B (280-320 nm), UV-A (320-400 nm) and visible (400 nm and above) radiation. In particular, Bache et al. compositions can be cured using radiation having a wavelength of 320 nm or more. When fully cured (regardless of the type of radiation used), the Bach et al. compositions exhibit hardnesses and impact resistances at least comparable to conventional coatings.

In the invention described here, the phosphors or scintillator described above are added to these Bach et al. compositions. Due to the fact that the exterior energy source penetrates deeper into the entirety of the Bach et al. compositions, thicker surface coatings can be realized. Further, the coatings can be applied to intricate surfaces having for example been prepared with recesses or protrusions.

In one embodiment, the phosphors or scintillators described above are complexed with the other X-ray down converting particles or other energy modulation agents permitting for example X-ray irradiation to also assist in this process. In one embodiment, the X-ray down converting particles or other energy modulation agents or metallic structures described herein permit X-ray irradiation to be used alone or in combination with the up converting particles.

Hence, in one embodiment of the invention, there is provided a system for curing a medium. The system includes a reduced-voltage x-ray source configured to generate x-rays from a peak applied cathode voltage at or below 80 kVp, and a plurality of energy-emitting particles in the medium which, upon radiation from the x-ray source, radiate at a lower energy than the x-ray source to cure the medium by photoactivation of photoinitiators in the medium (as discussed above). The ranges of peak applied cathode voltage discussed above are applicable for photocuring. The use of energy-emitting particles radiate with an intensity at least 10 times greater than that of $Y_2O_3$, upon exposure of $Y_2O_3$ to the radiation from an initiation source (or with the other greater intensities described above) are applicable for photocuring. The use of first and second energy-emitting particles to produce a combination of emission from the first and second plurality of energy-emitting particles to produce a spectrum for illumination of the photoactivatable agents in the medium (as described above) are applicable for photocuring.

Drug Packaging

The reagents and chemicals useful for methods and systems of the present invention may be packaged in kits to facilitate application of the present invention. In one exemplary embodiment, a kit including a psoralen, and fractionating containers for easy fractionation and isolation of autovaccines is contemplated. A further embodiment of kit would comprise at least one activatable pharmaceutical agent capable of causing a predetermined cellular change, at least one energy modulation agent capable of activating the at least one activatable agent when energized, and containers suitable for storing the agents in stable form, and preferably further comprising instructions for administering the at least one activatable pharmaceutical agent and at least one energy modulation agent to a subject, and for applying an initiation energy from an initiation energy source to activate the activatable pharmaceutical agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation or initiation source.

Other Applications

The phosphors, scintillators, fluorescent materials, and combinations and agglomerations thereof with and without plasmonic agents described above can also be used in other applications as described in the related applications to produce desirable changes in the medium in which these energy modulation agents are present. For example, as described in related application U.S. Ser. No. 12/401,478, the phosphors, scintillators, fluorescent materials, and combinations and agglomerations thereof with and without plasmonic agents described above can be used for sterilization and cold pasteurization of fluids, can be used for sterilization of blood products, can be used for waste water detoxification, can be used for photostimulation to alter or change a physical property such as for example, surface modification of biopolymers photografting or photopolymerization or photooxidizing surfaces of the polymers, can be used for photodeactivation of processes such as in cultured food products, and can be used for photoactivated cross-linking and curing of polymers.

Numerous modifications and variations of the invention are possible in light of the above teachings. It is therefore to be understood that within the scope of the appended claims, the invention may be practiced otherwise than as specifically described herein.

The invention claimed is:

1. A method for light stimulation within a medium, comprising:
introducing a first plurality of energy-emitting particles into the medium;
radiating the first plurality of energy-emitting particles in the medium with x-rays generated from an x-ray source having a peak applied cathode voltage at or below 105 kVp;
emitting a first lower electromagnetic energy than the x-ray source which interacts with the medium or with at least one photoactivatable agent in the medium wherein either (a) the first lower electromagnetic energy interacts directly with a target structure in a subject in need of treatment, wherein the first lower electromagnetic energy interacts directly with the target structure and induces a predetermined change in said target structure in situ in the medium of the subject, and wherein said predetermined change modifies the target structure and modulates the biological activity of the target structure, or (b) the first lower electromagnetic energy interacts with and activates at least one photoactivatable agent in the medium, wherein upon activation, the activated at least one photoactivatable agent reacts with a target structure in the subject to crosslink DNA present in the target structure.

2. The method of claim 1, further comprising:
introducing a second plurality of energy-emitting particles which upon radiation from the x-rays radiate at a second lower energy than the first radiation source; and
radiating the first and second plurality of light-emitting particles to produce a combined emission from the first and second plurality of light-emitting particles having a spectrum for illumination of the at least one photoactivatable agent in the medium, said spectrum having a wavelength distribution simulating at least a part of an absorption spectrum of the at least one photoactivatable agent or a spectrum of an ultraviolet discharge lamp.

3. The method of claim 2, wherein the wavelength distribution has a peak position in common with a peak in the absorption spectrum of the at least one photoactivatable agent or simulates an absorption edge of the absorption spectrum of the at least one photoactivatable agent.

4. The method of claim 2, wherein the first and second plurality of light-emitting particles comprises a weighted composition of a plurality of different light-emitting particles, where light emitted from the weighted composition simulate said part of the absorption spectrum of the at least one photoactivatable agent or said spectrum of an ultraviolet discharge lamp.

5. The method of claim 2, wherein said energy distribution resembles the absorption spectrum of theat least one photoactivatable agent or the spectrum of the ultraviolet discharge lamp.

6. The method of claim 5, wherein said energy distribution overlaps with the absorption spectrum of the at least one photoactivatable agent or said spectrum of the ultraviolet discharge lamp.

7. The method of claim 1, further comprising:
forming a concentrated energy source from emissions of the first plurality of energy-emitting particles by concentrating the first plurality of energy emitting particles about a target site; and
treating the target site by activation of the at least one photoactivatable agent from the concentrated energy source.

8. The method of claim 7, wherein the concentrated light source comprises a distribution of the first plurality of energy-emitting particles concentrated by at least one of an externally applied electric field or a magnetic field.

9. The method of claim 1, wherein the first plurality of energy-emitting particles in the medium self-assemble to form geometrical patterns.

10. The method of claim 1, wherein the geometrical patterns include at least one of dendrites, spherical clusters, and rings.

11. The method of claim 1, wherein the first plurality of energy-emitting particles comprises at least one of:
phosphor particles;
ionic doped phosphor particles ;
single crystal or poly-crystalline powders;
single crystal or poly-crystalline monoliths;
fluorescent particles;
scintillator particles;
a metallic shell encapsulating at least a fraction of a surface of the particles;
a semiconductor shell encapsulating at least a fraction of a surface of the particles;
an insulator shell encapsulating at least a fraction of a surface of the particles; and
quantum dots of a distributed size.

12. The method of claim 11, wherein a radial dimension of the metallic shell is set to a value where a surface plasmon resonance in the metallic shell resonates at a frequency which provides spectral overlap with either an absorption band or an emission band of the particles.

13. The method of claim 11, wherein the metallic shell comprises a plasmonic shell configured to enhance at least one of said absorption or said emission.

14. The method of claim 1, wherein the first plurality of light-emitting particles comprises particles having a dielectric core.

15. The method of claim 14, wherein a metallic shell covers said dielectric core and comprises at least one of Au, Ag, Cu, Ni, Pt, Pd, Co, Ru, Rh, or a combination thereof.

16. The method of claim 1, wherein the first plurality of energy-emitting particles comprises at least one of $Y_2O_3$; ZnS; ZnSe;MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, Er3+; ZnS:$Mn^{2+}$; ZnS:Mn,$Er^{3+}$; $CaWO_4$, $YaTO_4$, $YaTO_4$: Nb, $BaSO_4$:Eu, $La_2O_2$S:Tb, $BaSi_2O_5$:Pb, NaI(Tl), CsI(Tl), CsI(Na), CsI(pure), CsF, KI(Tl ), LiI(Eu), $BaF_2$, CaF, $CaF_2$ (Eu), ZnS(Ag), $CaWO_4$, $CdWO_4$, YAG(Ce) ($Y_3Al_5O_{12}$ (Ce)), BGO bismuth germanate, GSO gadolinium oxyorthosilicate, LSO lutetium oxyorthosilicate, $LaCl_3$(Ce), and $LaBr_3$(Ce).

17. The method of claim 1, wherein the first plurality of energy-emitting particles comprise at least one of phosphors, scintillators, fluorescent materials, and combinations and agglomerations thereof with or without plasmonic inducing agents.

18. The method of claim 1, further comprising:
administering the photoactivatable agent to the medium, wherein the medium is a subject, wherein the photoactivatable agent is at least one activatable pharmaceutical agent which is capable of effecting a predetermined cellular change when activated, wherein
light from the first plurality of particles interacts with the at least one activatable pharmaceutical agent to activate the activatable pharmaceutical agent in situ,
thus causing the predetermined cellular change to occur in the subject, wherein said predetermined cellular change treats a cell proliferation related disorder.

19. The method of claim 18, wherein the cell proliferation disorder is at least one member selected from the group consisting of cancer, bacterial infection, viral infection, immune rejection response, autoimmune disorders, aplastic conditions, and combinations thereof.

20. The method of claim 18, wherein the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones.

21. The method of claim 18, wherein the at least one activatable pharmaceutical agent is a psoralen, a coumarin, a porphyrin or a derivative thereof.

22. The method of claim 18, wherein the at least one activatable pharmaceutical agent is 8-MOP, TMP, or AMT.

23. The method of claim 18, wherein the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematophorphyrin, and phthadocyanine.

24. The method of claim 18, wherein the at least one activatable pharmaceutical agent is coupled to a carrier that is capable of binding to a receptor site.

25. The method of claim 24, wherein the carrier is one selected from insulin, interleukin, thymopoietin or transferrin.

26. The method of claim 25, wherein the at least one activatable pharmaceutical agent is coupled to the carrier by a covalent bond.

27. The method of claim 24, wherein the at least one activatable pharmaceutical agent is coupled to the carrier by non-covalent bond.

28. The method of claim 24, wherein the receptor site is one selected from nucleic acids of nucleated cells, antigenic sites on nucleated cells, or epitopes.

29. The method of claim 19, wherein the at least one activatable pharmaceutical agent has affinity for a target cell.

30. The method of claim 29, wherein the at least one activatable pharmaceutical agent is capable of being preferentially absorbed by a target cell.

31. The method of claim 30, wherein the predetermined cellular change is apoptosis in a target cell.

32. The method of claim 18, wherein:
the at least one activatable pharmaceutical agent causes an auto-vaccine effect in the subject that reacts with a target cell, or
the at least one activatable pharmaceutical agent is a DNA intercalator or a halogenated derivative thereof.

33. The method of claim 32, wherein the auto-vaccine effect is generated in a joint or lymph node.

34. The method of claim 1, wherein light from the first plurality of particles interacts with a target structure in a subject in need of treatment,
wherein the light contacts the target structure and induces a predetermined change in said target structure in situ in the medium of the subject, and
wherein said predetermined change modifies the target structure and modulates the biological activity of the target structure.

35. The method of claim 34, in which said predetermined change results in
destruction, lysis or inactivation of the target structure.

36. The method of claim 34, in which said predetermined change does not result in destruction or inactivation of the target structure.

37. The method of claim 34, in which said predetermined change occurs complemented by at least one of visible light, infrared light, or microwave radiation to the target structure.

38. The method of claim 34, in which said predetermined change enhances an activity of the target structure and wherein the activity enhanced is energy emission from the target, which then mediates, initiates or enhances a biological activity of other target structures in the subject, or of a second target structure.

39. The method of claim 34, wherein the target structure comprises at least one of a eukaryotic cell, a prokaryotic cell, a subcellular structure, an extracellular structure, a virus or prion, or a cellular tissue.

40. The method of claim 39, wherein the subcellular structure is a cell membrane, a nuclear membrane, cell nucleus, nucleic acid, mitochondria, ribosome, or other cellular organelle or component.

41. The method of claim 34, wherein the predetermined change results in treatment of a condition, disorder or disease in said subject.

42. The method of claim 34, wherein said condition, disorder or disease comprises at least one of a cancer, a disease occurring in a soft tissue and/or cartilage, a disease occurring in bone tissue, a chronic pain, an autoimmune disease, a prion, viral, bacterial, fungal, or parasitic infection, a disease characterized by varicose veins, a disease characterized by an enlarged prostate, a disease characterized by retinal injuries and other ocular diseases, a disease characterized by a behavioral, perceptional and/or cognitive disorder, or Parkinson's disease.

43. The method of claim 34, wherein said predetermined change comprises a wound healing, an enhancement of tissue growth, nerve regeneration or sensory regeneration/restoration, reduction or removal of fat deposits (liposuction), nerve (brain) imaging and stimulation or direct control of brain cell activity with light, modulation of cell death (apoptosis), modulating cell growth and division, modulation of an activity, quantity, or number of intracellular components in a cell, ormodulation of an activity, quantity, or number of extracellular components produced by, excreted by, or associated with a cell.

44. The method of claim 34, wherein said predetermined change modifies the target structure and modulates the biological activity of the target structure.

45. The method of claim 44, wherein said predetermined change comprises enhancement of tissue growth, nerve regeneration or sensory regeneration/restoration.

46. The method of claim 44, wherein said condition, disease, or disorder is a prion, viral, bacterial, fungal, or parasitic infection.

47. The method of claim 44, wherein said predetermined change comprises reduction or removal of fat deposits.

48. The method of claim 44, wherein said predetermined change comprises nerve (brain) imaging and stimulation or direct control of brain cell activity with light.

49. The method of claim 44, wherein said predetermined change comprises at least one of tissue regeneration, inflammation relief, pain relief, immune system fortification, changes in cell membrane permeability, up-regulation and down-regulation of adenosine triphosphate and nitric oxide.

50. The method of claim 1, wherein the x-rays are generated from a peak applied cathode voltage at or below 80 kVp.

* * * * *

UNITED STATES PATENT AND TRADEMARK OFFICE
CERTIFICATE OF CORRECTION

PATENT NO. : 10,232,190 B2
APPLICATION NO. : 15/649917
DATED : March 19, 2019
INVENTOR(S) : Frederic A. Bourke et al.

It is certified that error appears in the above-identified patent and that said Letters Patent is hereby corrected as shown below:

In the Specification

Column 2, Line 66, "$Er3^+$;" should read --$Er^{3+}$;--

Column 5, Line 61, "UVAnd" should read --UVA and--

Column 6, Line 20, "UVAnd" should read --UVA and--

Column 6, Line 23, "UVAnd" should read --UVA and--

Column 6, Line 26, "UVAnd" should read --UVA and--

Column 6, Line 44, "including." should read --including--

Column 7, Line 40, "system" should read --system;--

Column 8, Line 40, "the the" should read --the--

Column 9, Line 49, "smeer" should read --smear--

Column 12, Line 52, "UVAnd" should read --UVA and--

Column 18, Line 47, "UVAnd" should read --UVA and--

Column 18, Line 52, "UVAnd" should read --UVA and--

Column 19, Line 42, "UVAnd" should read --UVA and--

Column 19, Line 44, "UVAnd" should read --UVA and--

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,232,190 B2

Column 23, Line 30, "mediafter" should read --media after--

Column 23, Line 51, "mediand" should read --media and--

Column 23, Line 61, "mediand" should read --media and--

Column 24, Line 32, "Datanalysis:" should read --Data analysis:--

Column 25, Line 2, "datanalysis" should read --data analysis--

Column 28, Line 8, "ytrrium" should read --yttrium--

Column 30, Line 14, "chalcoginides" should read --chalcogenides--

Column 30, Lines 15-16, "oxo-chalcoginides;" should read --oxo-chalcogenides;--

Column 30, Line 23, "Al," should read --AI,--

Column 32, Line 13 (approx.), "$\kappa_2$," should read --$\lambda_2$,--

Column 36, Lines 23-24, "mitochondriat" should read --mitochondria at--

Column 36, Line 47, "napththoquinones," should read --naphthoquinones,--

Column 36, Lines 51-52, "anthroquinones," should read --anthraquinones,--

Columns 37-38, structure 1A, "$\overset{\cdot\,\text{H}\,\cdot}{\text{N}}$" should read --$\overset{\text{N}}{\text{H}}$--

Columns 39-40, structure 2A, "$\overset{\cdot\,\text{H}\,\cdot}{\text{N}}$" should read --$\overset{\text{N}}{\text{H}}$--

Column 43, Line 40, "Hepalology," should read --Hepatology,--

Column 43, Line 48, "PAnd" should read --PA and--

Column 44, Line 62, "mediand" should read --media and--

Column 45, Line 6, "cyclodextran." should read --cyclodextrin.--

Column 45, Line 38, "bacteriand" should read --bacteria and--

Column 47, Line 63, "ablasion" should read --ablation--

Column 47, Line 64, "arrhythmiand" should read --arrhythmia and--

CERTIFICATE OF CORRECTION (continued)
U.S. Pat. No. 10,232,190 B2

Column 47, Line 65, "restinosis)," should read --restenosis),--

Column 48, Line 1, "arthrisis," should read --arthritis,--

Column 48, Line 31, "ablasion" should read --ablation--

Column 48, Lines 31-32, "arrhythmiand" should read --arrhythmia and--

Column 48, Line 33, "restinosis)," should read --restenosis),--

Column 48, Line 36, "arthrisis," should read --arthritis,--

Column 50, Lines 34-35, "mitochondriat" should read --mitochondria at--

Column 50, Line 61, "napththoquinones," should read --naphthoquinones,--

Column 50, Line 66, "anthroquinones," should read --anthraquinones,--

Column 53, Lines 65-66, "electrophysipologically" should read --electrophysiologically--

Column 55, Line 29, "texaphryin)" should read --texaphyrin)--

Column 55, Line 33, "texaphryin" should read --texaphyrin--

Column 55, Line 40, "texaphryin" should read --texaphyrin--

Column 55, Line 47, "photophoresis." should read --photopheresis.--

Column 55, Line 48, "photophoresis" should read --photopheresis--

Column 58, Line 35, "bacterias" should read --bacteria as--

Column 59, Line 33, "NADHdehydrogenase" should read --NADH dehydrogenase--

Column 59, Line 42, "phychiatric" should read --psychiatric--

Column 60, Line 15, "cardiomyocites)" should read --cardiomyocytes)--

Column 60, Line 23, "viaborption" should read --via absorption--

Column 62, Line 52, "uncageing" should read --uncaging--

Column 63, Line 17, "photostimulaiton" should read --photostimulation--

Column 63, Line 17, "aluminand" should read --alumina and--

CERTIFICATE OF CORRECTION (continued)
U.S. Pat. No. 10,232,190 B2

Column 63, Lines 27-28, "photostimulaiton" should read --photostimulation--

Column 67, Line 1, "camphoquinone," should read --camphorquinone,--

In the Claims

Column 71, Line 5, Claim 5, "theat" should read --the at--

Column 71, Line 61, Claim 16, "ZnSe;MgS;" should read --ZnSe; MgS;--

Column 71, Line 64, Claim 16, "ZnS:Mn,$Er^{3+}$;" should read --ZnS:Mn, $Er^{3+}$--

Column 74, Line 21, Claim 43, "ormodulation" should read --or modulation--